US006867027B1

(12) United States Patent
Hayashizaki et al.

(10) Patent No.: US 6,867,027 B1
(45) Date of Patent: Mar. 15, 2005

(54) RNA POLYMERASE

(75) Inventors: Yoshihide Hayashizaki, Ibaraki (JP); Masanori Watahiki, Toyama (JP)

(73) Assignees: The Institute of Physical and Chemical Research, Wako (JP); Nippon Gene Co., Ltd., Tokyo (JP); Nippon Genetech Co., Ltd., Tokyo (JP)

( * ) Notice: Subject to any disclaimer, the term of this patent is extended or adjusted under 35 U.S.C. 154(b) by 0 days.

(21) Appl. No.: 09/254,344

(22) PCT Filed: Jul. 6, 1998

(86) PCT No.: PCT/JP98/03037

§ 371 (c)(1),
(2), (4) Date: Sep. 3, 1999

(87) PCT Pub. No.: WO99/02698

PCT Pub. Date: Jan. 21, 1999

(30) Foreign Application Priority Data

Jul. 7, 1997 (JP) .............................................. 9-180883
Jun. 4, 1998 (JP) ........................................... 10-155759

(51) Int. Cl.[7] .............................................. C12N 9/12
(52) U.S. Cl. ...................... 435/194; 435/193; 435/91.1; 435/440; 530/350; 530/358; 536/23.1; 536/23.2
(58) Field of Search ................................. 435/194, 193, 435/440; 530/350, 358

(56) References Cited

U.S. PATENT DOCUMENTS 5,385,834 A    1/1995  Ikeda ...................... 435/172.3

FOREIGN PATENT DOCUMENTS

| EP | 0 727 496 A | | 8/1996 |
| JP | 11075898 A | * | 3/1999 |
| WO | 96/14434 | | 4/1996 |
| WO | 96/12042 | | 5/1996 |

OTHER PUBLICATIONS

Ngo et al., Computational Complexity, Protein Stucture Prediction, and the Levinthal Paradox, in The Protein Folding Problem and Tertiary Stucture Prediction, 1994, Merz et al. (ed.) Birkhauser, Boston, MA, pp. 433 and 492–495.*

Sousa et al., A mutant T7 RNA polymerase as a DNA polymerase, 1995, EMBO Journal vol. 14, No. 18, pp 4609–4621.*

Axelrod, V.D. et al., "Transcription from Bacteriophage T7 and SP6 RNA Polymerase Promoters in the Presence of . . . ", BIOCHEMISTRY 1985, 24, 5716–5723.

Bonner, Gary et al., "Mutations in T7 RNA Polymerase That Support the Proposal for a Common Polymerase Active Site Stucture", The Embro Journal 1992, vol. 11, No. 10, 3767–3775.

Bonner, Gary et al., "Characterization of a Set of T7 RNA Polymerase Active Site Mutants", Journal of Biological Chemistry 1994, vol. 269, No. 40, 1994, 25120–25128.

Klement, J.F. et al., "Sequencing of DNA Using T3 RNA Polymerase and Chain Terminating Ribonucleotide Analogs", Gene Analysis Techniques 1986, No. 4, 3:59–66.

Kostyuk, D.A. et al., "Mutants of T7 RNA Polymerase That are able to Synthesize Both RNA and DNA", FEBS LETTERS 369, 1995, 165–168.

Makarova, Olga V. et al., "Transcribing of *Escherichia coli* Genes with Mutant T7 RNA Polymerases: Stability of lacZ mRNA Inversely Correlates with Polymerase Speed", Proc. Natl. Acad. Sci., vol. 92, No. 26, 1995, 12250–12254.

Parvin, J.D. et al., "Rapid RNA Sequencing Using Double–Stranded Template DNA, SP6 Polymerase, and 3'–Deoxynucleotide Triphosphates", DNA, vol. 5, No. 2, 1986, 167–171.

* cited by examiner

*Primary Examiner*—Richard Hutson
(74) *Attorney, Agent, or Firm*—Burns, Doane, Swecker & Mathis, L.L.P.

(57) ABSTRACT

Disclosed are RNA polymerases consisting of a wild type RNA polymerase provided that at least one of amino acids in the wild type RNA polymerase has been modified to enhance its ability for incorporating 3'-deoxyribonucleotides and derivatives thereof in comparison with the corresponding wild type RNA polymerases. Specifically, disclosed are, for example, the RNA polymerases wherein at least one amino acid present in a nucleotide binding sites of the wild type RNA polymerases such as phenylalanine has been replaced with tyrosine. The RNA polymerases of the present invention are a RNA polymerase which exhibits little or no bias for incorporation between ribonucleotides and 3'-deoxyribonucleotide as well as among ribonucleotides having different base groups and among deoxyribonucleotides having. different base groups.

13 Claims, 23 Drawing Sheets

Fig. 1

```
AGGCACTAAATGAACACGATTAACACGCTAAGAACGACTTCTCTGACATCGAACTGGCTGCTATCCCGTTCAACACT:3239
            M  N  T  I  N  I  A  K  N  D  F  S  D  I  E  L  A  A  I  P  F  N  T  :23
CTGGCTGACCATTACGGTGAGCGCGTTTAGCTCGCGTTGGCCCTTGAGCAGTCTTACGAGATGGGTGAAGCA:3317
 L  A  D  H  Y  G  E  R  L  A  R  E  Q  L  A  L  E  H  E  S  Y  E  M  G  E  A  :49
CGCTTCCGCAAGATGTTTGAGCGTCAACTTAAAGCTGGTGAGGTTGCGGATAACGCTGCCGCCAAGCCTCTCATCACT:3395
 R  F  R  K  M  F  E  R  Q  L  K  A  G  E  V  A  D  N  A  A  A  K  P  L  I  T  :75
ACCCTACTCCCAGTTCCTGCAAGATGATTGCACGCATCAAGCGATTGTTGAGGAAGTGAAAGCGCGGCAAGCGCCCGACA:3473
 T  L  L  P  K  M  I  A  R  I  N  D  W  F  E  E  V  K  R  G  K  R  P  T  :101
GCCTTCCAGTTCCTGCAAGAAATCAAGCCGGAAGCCGTAGCGTACCACCATTAAGACCACTCTGGCTTGCCTAACC:3551
 A  F  Q  F  L  Q  E  I  K  P  E  A  V  A  Y  I  T  I  K  T  T  L  A  C  L  T  :127
AGTGCTGACAATACAACCGTTCAGGCTGTAGCAAGCGCAATCGGTCGGGCCATTGAGGACGAGGCTCGCTTCGGTCGT:3629
 S  A  D  N  T  T  V  Q  A  V  A  S  A  I  G  R  A  I  E  D  E  A  R  F  G  R  :153
ATCCGTGACCTTGAAGCTAAGCACTTCAAGAACAACTTGAGGAACAACTTCAACAAGCGCTAGGGCACGTCTACAAG:3707
 I  R  D  L  E  A  K  H  F  K  N  V  E  Q  L  N  K  R  V  G  H  V  Y  K  :179
AAAGCATTTATGCAAGTTGTCGAGGCTGACATGCTCTCTAAGGGTCTGACTGGCGAGGCGTGTCTTCGTGGCAT:3785
 K  A  F  M  Q  V  V  E  A  D  M  L  S  K  G  L  L  G  G  E  A  W  S  S  W  H  :205
AAGGAGACTCTATTCATGTAGGAGTAGTCTCATTGAGTCAACGGAATGGTTAGCTTACACCGC:3863
 K  E  D  S  I  H  V  G  V  R  C  I  E  M  L  I  E  S  T  G  M  V  S  L  H  R  :231
CAAAATGCTGGCGTAGTGCTCAAGACTCGAGACTGCGCACCTGAACTCGCTATCGAGGCTATCGCAACCCGT:3941
 Q  N  A  G  V  V  G  Q  D  S  E  T  I  E  L  A  P  E  Y  A  E  A  I  A  T  R  :257
GCAGGTGCGCTGGCCATTCTCTCCGATGTTCCAACCTTGCTAGTTCCTAAGCCGTGGACTGGCATTACTGGT:4019
 A  G  A  L  A  G  I  S  P  M  F  Q  P  C  V  V  P  K  P  W  T  G  I  T  G  :283
GGTTGGCTATTGGGCTAACGGCTAAACGGCTGTCGTTCGTGCCTGTGCCTACTCACAGTAAGAAGCACTGATGCGCTACGAA:4097
 G  G  Y  W  A  N  G  R  R  P  L  A  L  V  R  T  H  S  K  K  A  L  M  R  Y  E  :309
GACGTTTACATGCCTGAGGTGTACAAGGCGATTAACATTGCGCAAAACACCGCCATGGAAAATCAACAAGAAAGTCCTA:4175
 D  V  Y  M  P  E  V  Y  K  A  I  N  I  A  Q  N  T  A  W  I  N  K  K  V  L  :335
GCCGTCGCCAACGTAATCACCAAGTGGAAGCATTGTCCGAGGACATCCCGGCGATTGAGCGTGAAGAACTCCCG:4253
 A  V  A  N  V  I  T  K  W  K  H  C  P  V  E  D  I  P  A  I  E  R  E  E  L  P  :361
ATGAAACCGGAAGACATGAATCCGGAAGCTCTCACCGCGTGAGTTCATGCTTGAGCAAGCAATAAGTTTGCTAACCATAAGGCC:4331
 M  K  P  E  D  I  D  M  N  P  E  A  L  T  A  W  K  R  A  A  A  V  Y  R  K  :387
GACAAGGCTCGCAAGTCTCGCCGTATCAGCCTTGAGTTCATGCTTGAGCAAGCAAATAAGTTTGCTAACCATAAGGCC:4409
 D  K  A  R  K  S  R  I  S  L  E  F  M  L  E  Q  A  N  K  F  A  N  H  K  A  :413
ATCTGGTTCCCTTACAACATGGACTGGCGCGGTCGCGTGTTACGCTGTGTCAATGTTCAACCCGCAAGGTAACGATATG:4487
 I  W  F  P  Y  N  M  D  W  R  G  R  V  Y  A  V  S  M  F  N  P  Q  G  N  D  M  :439
ACCAAAGGACTGCTTACGCTTGGCGAAGGTAAACCAATCGGTAAGGTTACTACTGGCTGAAAATCCACGGTGCA:4565
 T  K  G  L  L  T  L  A  K  G  K  P  I  G  K  E  G  Y  Y  W  L  K  I  H  G  A  :465
```

```
T7    1:MNTI-NIAKNDFSDIELAAIPFNTLADHYGERLAREQLALEHESYEMGEARFRKMFERQLKAGEVADNAAAKPLITT
T3    1:...I.E..E.....E.............SA..K........L..R..L..L...A....I........LA.
K11   1:...AL...GR...E......Y.I.SE..DQA.........A..L.RQ..L..L...V....F.........VL.
SP6   1:------------------------------MQDLH.I--.Q..E.MFNG.IR..EADQQ..IA..SES.T.WNRR.LSE
                                        *        *    *             **     **

T7   80:KMIARINDWFEEVKAKRGKRPTAFQFL-QEIKPE-A---VAYI-TIK--------TTLA----CLTSADNT-TVQ--A
T3   81:.LTT..VE.L..YAS.K.RK.S.YAP.-.LL....-S.F--.L..---VI.-----S...TNM...I...-.
K11  80:QLTK..D..K..QANA...K.R.YYPIKHGVAS.L.VSMG.EVLKE.RGVSSEAIAL.TIKVV.GN.HRPLKGHNP.
SP6  52:P.AEG.QAYK..YEG.K.RA.R.LA..Q-CVEN.---VA--.YI.M.--V----M--DM---NT.A.L---Q--
               *                    *                              *

T7  140:AIGRAIEDEARFGRIRDLEAKHFKNVEEQLNKRVGHVYKKAFMQVVEADMLSKGLLGG-EAWSSWHKEDSIHVGVR
T3  141:ML.K......................H......H.Q..............IGR........D..TTM...I.
K11 160:QL.K.L......EQ..AY....D......I..M....DN.A..KTDEQM...TK
SP6 110:SVAER...QV..SKLEGHA..Y.E.-.KKS.KASRTKS.RH.HNVA.V.EKSVAEKDADFDR.EA.P..TQLQI.TT
                **                                                              *

T7  219:MLIESTGMVSLHRQN-A-GVVG-QDSETIELAPEYAEAIATR-AGALAGISPMFQPCVVPPKPWTGITGGGYW-ANG
T3  220:.....L.E.Q.H..-.NA.-S.H.ALQ..Q..VDVL.K..........VA..........
K11 239:L...G..L.EMTKNKM.D.SDDVTSMQMVQ...AFV.LLSK.-.........H........VETV......-SV.
SP6 189:I--.GSVFYNGEPVFMRAMRTYGGKTIYYLQTS.SVGQWISAFKEHV.QL.AYA...I..R..RTPFN..FHTEKV
                                                                    ***   ****

T7  294:LALVRTHSKKALMRYEBDVYMPEVYKAINIAQNTAWKINKKVLAVANVITKWK-HCPVED-IPAIEREELP--MKPED
T3  295:..........G..............V.L.........V.E.VN..-N...A.-.SL..Q.-.--P..D.
K11 317:......R..A..H.......R......V.L......P.V.....V.E.VN.-..-..G..V.----PR.D.
SP6 268:IR..KGN-REHVRKLTQKQ..K......AL....Q.Q...D...IEEVIRLDLGYG.PSFK.L.DK.NK.ANPV.VE
                                     **                  ***  *****

T7  367:I----D-MNPEALTAW-----KRAA--AAVYRKDKARKSRRISLEFMLEQANKFANHKAIWFPYNMDWRGRVY-AVSMF
T3  368:..----.T.EA..KE.-----.K..--.GI..L...V......SK............
K11 390:..----..T.EV.RK....-----RKE.-.......Q..CRC...VA...........
SP6 347:LRGRELKEMLSPEQ.QQFINWKGEC.RL.TAETK.G.KSAAVVR.VG..R.YSAFES.Y.V.A..S.S...VQS.TL
              *                                        *  ***  *****
```

Fig. 4

```
T7   436:GNDMTKGLLTLAKGKPI-GKEGYYWLKIHGANCAGVDKVPFPERI-KFIEENHENI-MACAKSPLENTWAEQDSPF
T3   437:.................-.....E..F........-....-A...KHVDD..L...D.IN........:
K11  459:.................-.......S........-...LD.F.............EG..L.S.AD..N...TQ....:
SP6  427:S..LG.A..RFTE.R.V.VN..V.ALK.PC.N...LW.W..KT.DV.VSNVLD.EFQDMCRDI.AD..TF.Q..KA.A.Y
              **                      *            ***           **       **    *      *  *

T7   513:AFCFEYA----GVQHHG-L-SYNCSLPLAFDGSCSGIQHFSAMLRDEVGGRAVNLLPSETVQDIYGIVAKKVNEILQA
T3   514:.......----.....-T-...............................................Q......RQ
K11  536:.......----......-.-.....K....N............SI..............D....K....D...V.HQ
SP6  507:W......QYLDLVDE.RADEFRTH..VHQ...............Y......AK....K..DAP.....A..-Q.--V-I
           * *****              **        *********  *******  *  *      *    **  **    *  *

T7   588:NGTDNEVVTVTDENTGEISEKVKLGTKALAGWMLAYGVTRSVTKRSVMTLAYGSKEFGFRQQVLEDTIQ-PAIDSGK
T3   589:....P..MI....KD......L....ST..Q.................................D...-.....
K11  611:...SQTV.EQIA.KE...FH...T..ESV..A....Q.....K.....................SLV..-....N.E
SP6  581:.ALYMDADDA.TFTS.SVTLSGT-ELR.M.SA.DSI.I...L..KP....P...TRLTC.ES.IDYIVDLEEKEAQ..
                   *             **         *  **              **

T7   667:FT-QPNQAAGYMAKLIWESVSVTVVAAVEAMNWLKSAAKLLAAEVKDKKTGEILR---KRC-AVHWVTPDGFPVWQE
T3   668:..-........................DA.......................K...---..-H......T......
K11  690:.-H.........................DA.T....................K.V.---...-I........ .. .
SP6  660:EGRTA.KVHPFEDDRQDYLTPGAAYNYMT.LI.PSISEVVK.PI.AM.MIRQLA.FAA..NEGLMYTL.T..ILE.K
                                *                            *          **    *       *

T7   742:PIQTRLNLMFLGQFRLQPTINTNKDSEIDAHKQESGIAPNFVHSQDGSHLRKTVVWAHEKYGIESFALIHDSFGTIP
T3   743:..L.K..DMI.............L....G................M...Y............D.......:
K11  765:QN.A..K.V.....ANVKM.Y..G......................M..H.N.V....D.......S....:
SP6  740:TEML.VRTCLM.DIKMSLQVE.---.IV.EAAMGAA.......GH.A...IL..CELVD.-.VT.I.V......HA
              *    *    *          * *      ******    *  ***           **    ****  **  *.

T7   822:ANLFKAVRETMVDTYESCDVLADFYDQFADQLHESQLDKMPALPAKGNLNLRDILESDFAFA
T3   823:GK......................I...NN......S......T.......P.K.....Q...K....:
K11  845:G..............K...DN..I................V...D...K....:
SP6  816:LT.RV.LKGQ..AM.IDGNA.QKL-LE-EHEVR-WMV.TGIEV.EQ.EFD.NE.MD.EYV..
         *  *   *       *             *                    *      ****  **.
```

Fig. 6

```
T7RNApol    1:MNTI-NIAKNDFSDIELAAIPFNTLADHYGERLAREQLALEHESYEMGEARFRKMFERQL
T3RNApol    1:...I.E..E.....B......................SA..K..........L..R..L...A
              ** * ** ***** **********************  ** ****** ** ** *** *

T7RNApol   60:KAGEVADNAAAKPLITTLLPKMIARINDWFEEVKAKRGKRPTAFQFLQEIKPEAVAYITI
T3RNApol   61:....I........LA......LTT..VE.L..YAS.K.RK.S.YAP..LL....S.F..L
              **** ********  ****** *** ****  *** * **   ***  **   * *  *

T7RNApol  120:KTTLACLTSADNTTVQAVASAIGRAIEDEARFGRIRDLEAKHFKKNVEEQLNKRVGHVYK
T3RNApol  121:..VI..S....TNM..I..A.GML.K....................H.......H.Q...
                ** **    ***  *  * *** *********************** ******* * ***

T7RNApol  180:KAFMQVVEADMLSKGLLGGEAWSSWHKEDSIHVGVRCIEMLIESTGMVSLHRQNAGVVGQ
T3RNApol  181:..........IGR.............D..TTM...I.L.......L.E.Q.H...NA.S
              **********   ************ **  **   * * ******* * * * *** *

T7RNApol  240:DSETIELAPEYAEAIATRAGALAGISPMFQPCVVPPKPWTGITGGGYWANGRRPLALVRT
T3RNApol  241:..H.ALQ..Q..VDVL.K.............VA...........................
                * ** *  *  * ** * ***************  ************************

T7RNApol  300:HSKKALMRYEDVYMPEVYKAINIAQNTAWKINKKVLAVANVITKWKHCPVEDIPAIEREE
T3RNApol  301:.....G..............V.L.............V.E.VN..N...A...SL..Q..
              ***** ************** * ************* * * **  *   *   ** * **

T7RNApol  360:LPMKPEDIDMNPEALTAWKRAAAVYRKDKARKSRRISLEFMLEQANKFANHKAIWFPYN
T3RNApol  361:..P..D...T.EA..KE..K...GI...L....V.................SK......
                ** *** ** ** ** ** *** ****** ******************  ********
```

Fig. 7

```
T7RNApol 420:MDWRGRVYAVSMFNPQGNDMTKGLLTLAKGKPIGKEGYYWLKIHGANCAGVDKVPFPERI
T3RNApol 421:............P.................................E..F........
             ************ ********************************** ** *********

T7RNApol 480:KFIEENHENIMACAKSPLENTWWAEQDSPFCFLAFCFEYAGVQHHGLSYNCSLPLAFDGS
T3RNApol 481:A....KHVDD.L...D.IN.....................T...................
              *   *    * *** *  **********************.******************

T7RNApol 540:CSGIQHFSAMLRDEVGGRAVNLLPSETVQDIYGIVAKKVNEILQADAINGTDNEVVTVTD
T3RNApol 541:..........................................Q......KQ.....P..MI....
             ******************************************.******  *****  **.****

T7RNApol 600:ENTGEISEKVKLGTKALAGQWLAYGVTRSVTKRSVMTLAYGSKEFGFRQQVLEDTIQPAI
T3RNApol 601:KD......L....ST..Q.......................D.................
               **   ***** **  * ************************.****************

T7RNApol 660:DSGKGLMFTQPNQAAGYMAKLIWESVSVTVVAAVEAMNWLKSAAKLLAAEVKDKKTGEIL
T3RNApol 661:........................DA................................K....
             ************************  ***********************************. ***

T7RNApol 720:RKRCAVHWVTPDGFPVWQEYKKPIQTRLNLMFLGQFRLQPTINTNKDSEIDAHKQESGIA
T3RNApol 721:..H.....T..............R..L..K..DMI..........L...G.........
             ** *****.************** ** ** *  *  **********.***.*********

T7RNApol 780:PNFVHSQDGSHLRKTVVWAHEKYGIESFALIHDSFGTIPADAANLFKAVRETMVDTYESC
T3RNApol 781:........................M...Y..............................GK........I...NN
             ************************ *** ******************************  ******** *** ***

T7RNApol 840:DVLADFYDQFADQLHESQLDKMPALPAKGNLNLRDILESDFAFA
T3RNApol 841:......S.......T.......P..K.....Q...K.......
             ****** ******* ******* ** ***** *** ********
```

Fig. 8

| | | | | |
|---|---|---|---|---|
| T7 | 617:AGQWLAYGVTRSVMTLAYGSKEFGFRQQVLEDTIQ-PAIDSGKGLMFT-QPNQAAGYMAKLIWESVSVTV |
| T7 F644Y | 617:AGQWLAYGVTRSVMTLAYGSKEYGFRQQVLEDTIQ-PAIDSGKGLMFT-QPNQAAGYMAKLIWESVSVTV |
| T7 L665P/F667Y | 617:AGQWLAYGVTRSVMTLAYGSKEFGFRQQVLEDTIQ-PAIDSGKGPMYT-QPNQAAGYMAKLIWESVSVTV |
| T3 | 618:..Q.............................D...............DA....... |
| K11 | 640:..A...Q......K..........SLV.........N.E......H...DA.T..... |
| SP6 | 609:..SA.DSI.I...L..KP....P..TRLTC.ES.IDYIVDLEEKEAQ.AVAEGRTA.KVHPEDDRQDYLTPGAA |
| |  .* * * * * |
| | Motif B |

Arrows at positions 644 and 667.

SEQUENCE LISTING

<160> NUMBER OF SEQ ID NOS: 39

<210> SEQ ID NO 1
<211> LENGTH: 2659
<212> TYPE: DNA
<213> ORGANISM: Bacteriophage T7
<220> FEATURE:
<221> NAME/KEY: CDS
<222> LOCATION: (10)..(2658)

<400> SEQUENCE: 1

```
aggcactaa atg aac acg att aac atc gct aag aac gac ttc tct gac atc    51
          Met Asn Thr Ile Asn Ile Ala Lys Asn Asp Phe Ser Asp Ile
            1               5                  10 gaa ctg gct gct atc ccg ttc aac act ctg gct gac cat tac ggt gag      99
Glu Leu Ala Ala Ile Pro Phe Asn Thr Leu Ala Asp His Tyr Gly Glu
 15                  20                  25                  30 cgt tta gct cgc gaa cag ttg gcc ctt gag cat gag tct tac gag atg     147
Arg Leu Ala Arg Glu Gln Leu Ala Leu Glu His Glu Ser Tyr Glu Met
                 35                  40                  45 ggt gaa gca cgc ttc cgc aag atg ttt gag cgt caa ctt aaa gct ggt     195
Gly Glu Ala Arg Phe Arg Lys Met Phe Glu Arg Gln Leu Lys Ala Gly
             50                  55                  60 gag gtt gcg gat aac gct gcc gcc aag cct ctc atc act acc cta ctc     243
Glu Val Ala Asp Asn Ala Ala Ala Lys Pro Leu Ile Thr Thr Leu Leu
         65                  70                  75 cct aag atg att gca cgc atc aac gac tgg ttt gag gaa gtg aaa gct     291
Pro Lys Met Ile Ala Arg Ile Asn Asp Trp Phe Glu Glu Val Lys Ala
     80                  85                  90 aag cgc ggc aag cgc ccg aca gcc ttc cag ttc ctg caa gaa atc aag     339
Lys Arg Gly Lys Arg Pro Thr Ala Phe Gln Phe Leu Gln Glu Ile Lys
 95                 100                 105                 110 ccg gaa gcc gta gcg tac atc acc att aag acc act ctg gct tgc cta     387
Pro Glu Ala Val Ala Tyr Ile Thr Ile Lys Thr Thr Leu Ala Cys Leu
                115                 120                 125 acc agt gct gac aat aca acc gtt cag gct gta gca agc gca atc ggt     435
Thr Ser Ala Asp Asn Thr Thr Val Gln Ala Val Ala Ser Ala Ile Gly
            130                 135                 140 cgg gcc att gag gac gag gct cgc ttc ggt cgt atc cgt gac ctt gaa     483
Arg Ala Ile Glu Asp Glu Ala Arg Phe Gly Arg Ile Arg Asp Leu Glu
        145                 150                 155 gct aag cac ttc aag aaa aac gtt gag gaa caa ctc aac aag cgc gta     531
Ala Lys His Phe Lys Lys Asn Val Glu Glu Gln Leu Asn Lys Arg Val
    160                 165                 170 ggg cac gtc tac aag aaa gca ttt atg caa gtt gtc gag gct gac atg     579
Gly His Val Tyr Lys Lys Ala Phe Met Gln Val Val Glu Ala Asp Met
175                 180                 185                 190 ctc tct aag ggt cta ctc ggt ggc gag gcg tgg tct tcg tgg cat aag     627
Leu Ser Lys Gly Leu Leu Gly Gly Glu Ala Trp Ser Ser Trp His Lys
                195                 200                 205 gaa gac tct att cat gta gga gta cgc tgc atc gag atg ctc att gag     675
Glu Asp Ser Ile His Val Gly Val Arg Cys Ile Glu Met Leu Ile Glu
            210                 215                 220 tca acc gga atg gtt agc tta cac cgc caa aat gct ggc gta gta ggt     723
Ser Thr Gly Met Val Ser Leu His Arg Gln Asn Ala Gly Val Val Gly
        225                 230                 235 caa gac tct gag act atc gaa ctc gca cct gaa tac gct gag gct atc     771
Gln Asp Ser Glu Thr Ile Glu Leu Ala Pro Glu Tyr Ala Glu Ala Ile
    240                 245                 250
```

```
gca acc cgt gca ggt gcg ctg gct ggc atc tct ccg atg ttc caa cct    819
Ala Thr Arg Ala Gly Ala Leu Ala Gly Ile Ser Pro Met Phe Gln Pro
255                 260                 265                 270 tgc gta gtt cct cct aag ccg tgg act ggc att act ggt ggt ggc tat    867
Cys Val Val Pro Pro Lys Pro Trp Thr Gly Ile Thr Gly Gly Gly Tyr
                275                 280                 285 tgg gct aac ggt cgt cgt cct ctg gcg ctg gtg cgt act cac agt aag    915
Trp Ala Asn Gly Arg Arg Pro Leu Ala Leu Val Arg Thr His Ser Lys
            290                 295                 300 aaa gca ctg atg cgc tac gaa gac gtt tac atg cct gag gtg tac aaa    963
Lys Ala Leu Met Arg Tyr Glu Asp Val Tyr Met Pro Glu Val Tyr Lys
        305                 310                 315 gcg att aac att gcg caa aac acc gca tgg aaa atc aac aag aaa gtc   1011
Ala Ile Asn Ile Ala Gln Asn Thr Ala Trp Lys Ile Asn Lys Lys Val
    320                 325                 330 cta gcg gtc gcc aac gta atc acc aag tgg aag cat tgt ccg gtc gag   1059
Leu Ala Val Ala Asn Val Ile Thr Lys Trp Lys His Cys Pro Val Glu
335                 340                 345                 350 gac atc cct gcg att gag cgt gaa gaa ctc ccg atg aaa ccg gaa gac   1107
Asp Ile Pro Ala Ile Glu Arg Glu Glu Leu Pro Met Lys Pro Glu Asp
                355                 360                 365 atc gac atg aat cct gag gct ctc acc gcg tgg aaa cgt gct gcc gct   1155
Ile Asp Met Asn Pro Glu Ala Leu Thr Ala Trp Lys Arg Ala Ala Ala
            370                 375                 380 gct gtg tac cgc aag gac aag gct cgc aag tct cgc cgt atc agc ctt   1203
Ala Val Tyr Arg Lys Asp Lys Ala Arg Lys Ser Arg Arg Ile Ser Leu
        385                 390                 395 gag ttc atg ctt gag caa gcc aat aag ttt gct aac cat aag gcc atc   1251
Glu Phe Met Leu Glu Gln Ala Asn Lys Phe Ala Asn His Lys Ala Ile
    400                 405                 410 tgg ttc cct tac aac atg gac tgg cgc ggt cgt gtt tac gct gtg tca   1299
Trp Phe Pro Tyr Asn Met Asp Trp Arg Gly Arg Val Tyr Ala Val Ser
415                 420                 425                 430 atg ttc aac ccg caa ggt aac gat atg acc aaa gga ctg ctt acg ctg   1347
Met Phe Asn Pro Gln Gly Asn Asp Met Thr Lys Gly Leu Leu Thr Leu
                435                 440                 445 gcg aaa ggt aaa cca atc ggt aag gaa ggt tac tac tgg ctg aaa atc   1395
Ala Lys Gly Lys Pro Ile Gly Lys Glu Gly Tyr Tyr Trp Leu Lys Ile
            450                 455                 460 cac ggt gca aac tgt gcg ggt gtc gat aag gtt ccg ttc cct gag cgc   1443
His Gly Ala Asn Cys Ala Gly Val Asp Lys Val Pro Phe Pro Glu Arg
        465                 470                 475 atc aag ttc att gag gaa aac cac gag aac atc atg gct tgc gct aag   1491
Ile Lys Phe Ile Glu Glu Asn His Glu Asn Ile Met Ala Cys Ala Lys
    480                 485                 490 tct cca ctg gag aac act tgg tgg gct gag caa gat tct ccg ttc tgc   1539
Ser Pro Leu Glu Asn Thr Trp Trp Ala Glu Gln Asp Ser Pro Phe Cys
495                 500                 505                 510 ttc ctt gcg ttc tgc ttt gag tac gct ggg gta cag cac cac ggc ctg   1587
Phe Leu Ala Phe Cys Phe Glu Tyr Ala Gly Val Gln His His Gly Leu
                515                 520                 525 agc tat aac tgc tcc ctt ccg ctg gcg ttt gac ggg tct tgc tct ggc   1635
Ser Tyr Asn Cys Ser Leu Pro Leu Ala Phe Asp Gly Ser Cys Ser Gly
            530                 535                 540 atc cag cac ttc tcc gcg atg ctc cga gat gag gta ggt ggt cgc gcg   1683
Ile Gln His Phe Ser Ala Met Leu Arg Asp Glu Val Gly Gly Arg Ala
        545                 550                 555 gtt aac ttg ctt cct agt gaa acc gtt cag gac atc tac ggg att gtt   1731
Val Asn Leu Leu Pro Ser Glu Thr Val Gln Asp Ile Tyr Gly Ile Val
    560                 565                 570
```

```
gct aag aaa gtc aac gag att cta caa gca gac gca atc aat ggg acc      1779
Ala Lys Lys Val Asn Glu Ile Leu Gln Ala Asp Ala Ile Asn Gly Thr
575                 580                 585                 590 gat aac gaa gta gtt acc gtg acc gat gag aac act ggt gaa atc tct      1827
Asp Asn Glu Val Val Thr Val Thr Asp Glu Asn Thr Gly Glu Ile Ser
                595                 600                 605 gag aaa gtc aag ctg ggc act aag gca ctg gct ggt caa tgg ctg gct      1875
Glu Lys Val Lys Leu Gly Thr Lys Ala Leu Ala Gly Gln Trp Leu Ala
        610                 615                 620 tac ggt gtt act cgc agt gtg act aag cgt tca gtc atg acg ctg gct      1923
Tyr Gly Val Thr Arg Ser Val Thr Lys Arg Ser Val Met Thr Leu Ala
            625                 630                 635 tac ggg tcc aaa gag ttc ggc ttc cgt caa caa gtg ctg gaa gat acc      1971
Tyr Gly Ser Lys Glu Phe Gly Phe Arg Gln Gln Val Leu Glu Asp Thr
640                 645                 650 att cag cca gct att gat tcc ggc aag ggt ctg atg ttc act cag ccg      2019
Ile Gln Pro Ala Ile Asp Ser Gly Lys Gly Leu Met Phe Thr Gln Pro
655                 660                 665                 670 aat cag gct gct gga tac atg gct aag ctg att tgg gaa tct gtg agc      2067
Asn Gln Ala Ala Gly Tyr Met Ala Lys Leu Ile Trp Glu Ser Val Ser
                675                 680                 685 gtg acg gtg gta gct gcg gtt gaa gca atg aac tgg ctt aag tct gct      2115
Val Thr Val Val Ala Ala Val Glu Ala Met Asn Trp Leu Lys Ser Ala
        690                 695                 700 gct aag ctg ctg gct gct gag gtc aaa gat aag aag act gga gag att      2163
Ala Lys Leu Leu Ala Ala Glu Val Lys Asp Lys Lys Thr Gly Glu Ile
            705                 710                 715 ctt cgc aag cgt tgc gct gtg cat tgg gta act cct gat ggt ttc cct      2211
Leu Arg Lys Arg Cys Ala Val His Trp Val Thr Pro Asp Gly Phe Pro
720                 725                 730 gtg tgg cag gaa tac aag aag cct att cag acg cgc ttg aac ctg atg      2259
Val Trp Gln Glu Tyr Lys Lys Pro Ile Gln Thr Arg Leu Asn Leu Met
735                 740                 745                 750 ttc ctc ggt cag ttc cgc tta cag cct acc att aac acc aac aaa gat      2307
Phe Leu Gly Gln Phe Arg Leu Gln Pro Thr Ile Asn Thr Asn Lys Asp
                755                 760                 765 agc gag att gat gca cac aaa cag gag tct ggt atc gct cct aac ttt      2355
Ser Glu Ile Asp Ala His Lys Gln Glu Ser Gly Ile Ala Pro Asn Phe
        770                 775                 780 gta cac agc caa gac ggt agc cac ctt cgt aag act gta gtg tgg gca      2403
Val His Ser Gln Asp Gly Ser His Leu Arg Lys Thr Val Val Trp Ala
            785                 790                 795 cac gag aag tac gga atc gaa tct ttt gca ctg att cac gac tcc ttc      2451
His Glu Lys Tyr Gly Ile Glu Ser Phe Ala Leu Ile His Asp Ser Phe
800                 805                 810 ggt acc att ccg gct gac gct gcg aac ctg ttc aaa gca gtg cgc gaa      2499
Gly Thr Ile Pro Ala Asp Ala Ala Asn Leu Phe Lys Ala Val Arg Glu
815                 820                 825                 830 act atg gtt gac aca tat gag tct tgt gat gta ctg gct gat ttc tac      2547
Thr Met Val Asp Thr Tyr Glu Ser Cys Asp Val Leu Ala Asp Phe Tyr
                835                 840                 845 gac cag ttc gct gac cag ttg cac gag tct caa ttg gac aaa atg cca      2595
Asp Gln Phe Ala Asp Gln Leu His Glu Ser Gln Leu Asp Lys Met Pro
        850                 855                 860 gca ctt ccg gct aaa ggt aac ttg aac ctc cgt gac atc tta gag tcg      2643
Ala Leu Pro Ala Lys Gly Asn Leu Asn Leu Arg Asp Ile Leu Glu Ser
            865                 870                 875 gac ttc gcg ttc gcg t                                                2659
Asp Phe Ala Phe Ala
```

<210> SEQ ID NO 2
<211> LENGTH: 883
<212> TYPE: PRT
<213> ORGANISM: Bacteriophage T7

<400> SEQUENCE: 2

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
        355                 360                 365
```

-continued

```
Met Asn Pro Glu Ala Leu Thr Ala Trp Lys Arg Ala Ala Ala Val
    370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
                435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His Gly Leu Ser Tyr
        515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
```

-continued

```
                785                 790                 795                 800
Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
                820                 825                 830

Val Asp Thr Tyr Glu Ser Cys Asp Val Leu Ala Asp Phe Tyr Asp Gln
                835                 840                 845

Phe Ala Asp Gln Leu His Glu Ser Gln Leu Asp Lys Met Pro Ala Leu
                850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 3
<211> LENGTH: 853
<212> TYPE: PRT
<213> ORGANISM: Bacteriophage T7

<400> SEQUENCE: 3

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
                20                  25                  30

Ala Arg Glu Gln Leu Ala Leu Glu His Glu Ser Tyr Glu Met Gly Glu
            35                  40                  45

Ala Arg Phe Arg Lys Met Phe Glu Arg Gln Leu Lys Ala Gly Glu Val
        50                  55                  60

Ala Asp Asn Ala Ala Ala Lys Pro Leu Ile Thr Thr Lys Met Ile Ala
65                  70                  75                  80

Arg Ile Asn Asp Trp Phe Glu Glu Val Lys Ala Lys Arg Gly Lys Arg
                85                  90                  95

Pro Thr Ala Phe Gln Phe Leu Gln Glu Ile Lys Pro Glu Ala Val Ala
                100                 105                 110

Tyr Ile Thr Ile Lys Thr Thr Leu Ala Cys Leu Thr Ser Ala Asp Asn
            115                 120                 125

Thr Thr Val Gln Ala Ala Ile Gly Arg Ala Ile Glu Asp Glu Ala Arg
        130                 135                 140

Phe Gly Arg Ile Arg Asp Leu Glu Ala Lys His Phe Lys Lys Asn Val
145                 150                 155                 160

Glu Glu Gln Leu Asn Lys Arg Val Gly His Val Tyr Lys Lys Ala Phe
                165                 170                 175

Met Gln Val Val Glu Ala Asp Met Leu Ser Lys Gly Leu Leu Gly Gly
                180                 185                 190

Glu Ala Trp Ser Ser Trp His Lys Glu Asp Ser Ile His Val Gly Val
            195                 200                 205

Arg Met Leu Ile Glu Ser Thr Gly Met Val Ser Leu His Arg Gln Asn
        210                 215                 220

Ala Gly Val Val Gly Gln Asp Ser Glu Thr Ile Glu Leu Ala Pro Glu
225                 230                 235                 240

Tyr Ala Glu Ala Ile Ala Thr Arg Ala Gly Ala Leu Ala Gly Ile Ser
                245                 250                 255

Pro Met Phe Gln Pro Cys Val Val Pro Pro Lys Pro Trp Thr Gly Ile
                260                 265                 270

Thr Gly Gly Gly Tyr Trp Ala Asn Gly Leu Ala Leu Val Arg Thr His
```

-continued

```
                275                 280                 285
Ser Lys Lys Ala Leu Met Arg Tyr Glu Asp Val Tyr Met Pro Glu Val
    290                 295                 300
Tyr Lys Ala Ile Asn Ile Ala Gln Asn Thr Ala Trp Lys Ile Asn Lys
305                 310                 315                 320
Lys Val Leu Ala Val Ala Asn Val Ile Thr Lys Trp Lys His Cys Pro
                325                 330                 335
Val Glu Asp Ile Pro Ala Ile Glu Arg Glu Leu Pro Met Lys Pro
                340                 345                 350
Glu Asp Ile Asp Met Asn Pro Glu Ala Leu Thr Ala Trp Lys Arg Ala
                355                 360                 365
Ala Ala Ala Val Tyr Arg Lys Asp Lys Ala Arg Lys Ser Arg Arg Ile
    370                 375                 380
Ser Leu Glu Phe Met Leu Glu Gln Ala Asn Lys Phe Ala Asn His Lys
385                 390                 395                 400
Ala Ile Trp Phe Pro Tyr Asn Met Asp Trp Arg Gly Arg Val Tyr Ala
                405                 410                 415
Val Ser Met Phe Gly Asn Asp Met Thr Lys Gly Leu Leu Thr Leu Ala
                420                 425                 430
Lys Gly Lys Pro Ile Gly Lys Glu Gly Tyr Tyr Trp Leu Lys Ile His
                435                 440                 445
Gly Ala Asn Cys Ala Gly Val Asp Lys Val Pro Phe Pro Glu Arg Ile
    450                 455                 460
Lys Phe Ile Glu Glu Asn His Glu Asn Ile Met Ala Cys Ala Lys Ser
465                 470                 475                 480
Pro Leu Glu Asn Thr Trp Trp Ala Glu Gln Asp Ser Pro Phe Ala Phe
                485                 490                 495
Cys Phe Glu Tyr Ala Gly Val Gln His His Gly Leu Ser Tyr Asn Cys
                500                 505                 510
Ser Leu Pro Leu Ala Phe Asp Gly Ser Cys Ser Gly Ile Gln His Phe
                515                 520                 525
Ser Ala Met Leu Arg Asp Glu Val Gly Gly Arg Ala Val Asn Leu Leu
    530                 535                 540
Pro Ser Glu Thr Val Gln Asp Ile Tyr Gly Ile Val Ala Lys Lys Val
545                 550                 555                 560
Asn Glu Ile Leu Gln Ala Asn Gly Thr Asp Asn Glu Val Val Thr Val
                565                 570                 575
Thr Asp Glu Asn Thr Gly Glu Ile Ser Glu Lys Val Lys Leu Gly Thr
                580                 585                 590
Lys Ala Leu Ala Gly Gln Trp Leu Ala Tyr Gly Val Thr Arg Ser Val
                595                 600                 605
Thr Lys Arg Ser Val Met Thr Leu Ala Tyr Gly Ser Lys Glu Phe Gly
    610                 615                 620
Phe Arg Gln Gln Val Leu Glu Asp Thr Ile Gln Pro Ala Ile Asp Ser
625                 630                 635                 640
Gly Lys Phe Thr Gln Pro Asn Gln Ala Ala Gly Tyr Met Ala Lys Leu
                645                 650                 655
Ile Trp Glu Ser Val Ser Val Thr Val Val Ala Ala Val Glu Ala Met
                660                 665                 670
Asn Trp Leu Lys Ser Ala Ala Lys Leu Leu Ala Ala Glu Val Lys Asp
                675                 680                 685
Lys Lys Thr Gly Glu Ile Leu Arg Lys Arg Cys Ala Val His Trp Val
                690                 695                 700
```

```
Thr Pro Asp Gly Phe Pro Val Trp Gln Glu Pro Ile Gln Thr Arg Leu
705                 710                 715                 720

Asn Leu Met Phe Leu Gly Gln Phe Arg Leu Gln Pro Thr Ile Asn Thr
                725                 730                 735

Asn Lys Asp Ser Glu Ile Asp Ala His Lys Gln Glu Ser Gly Ile Ala
            740                 745                 750

Pro Asn Phe Val His Ser Gln Asp Gly Ser His Leu Arg Lys Thr Val
                755                 760                 765

Val Trp Ala His Glu Lys Tyr Gly Ile Glu Ser Phe Ala Leu Ile His
    770                 775                 780

Asp Ser Phe Gly Thr Ile Pro Ala Asn Leu Phe Lys Ala Val Arg Glu
785                 790                 795                 800

Thr Met Val Asp Thr Tyr Glu Ser Cys Asp Val Leu Ala Asp Phe Tyr
                805                 810                 815

Asp Gln Phe Ala Asp Gln Leu His Glu Ser Gln Leu Asp Lys Met Pro
            820                 825                 830

Ala Leu Pro Ala Lys Gly Asn Leu Asn Leu Arg Asp Ile Leu Glu Ser
            835                 840                 845

Asp Phe Ala Phe Ala
            850
```

<210> SEQ ID NO 4
<211> LENGTH: 884
<212> TYPE: PRT
<213> ORGANISM: Bacteriophage T3

<400> SEQUENCE: 4

```
Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
                20                  25                  30

Leu Ala Lys Glu Gln Leu Ala Leu Glu His Glu Ser Tyr Glu Leu Gly
            35                  40                  45

Glu Arg Arg Phe Leu Lys Met Leu Glu Arg Gln Ala Lys Ala Gly Glu
    50                  55                  60

Ile Ala Asp Asn Ala Ala Ala Lys Pro Leu Leu Ala Thr Leu Leu Pro
65                  70                  75                  80

Lys Leu Thr Thr Arg Ile Val Glu Trp Leu Glu Glu Tyr Ala Ser Lys
                85                  90                  95

Lys Gly Arg Lys Pro Ser Ala Tyr Ala Pro Leu Gln Leu Leu Lys Pro
            100                 105                 110

Glu Ala Ser Ala Phe Ile Thr Leu Lys Val Ile Leu Ala Ser Leu Thr
        115                 120                 125

Ser Thr Asn Met Thr Thr Ile Gln Ala Ala Gly Met Leu Gly Lys
130                 135                 140

Ala Ile Glu Asp Glu Ala Arg Phe Gly Arg Ile Arg Asp Leu Glu Ala
145                 150                 155                 160

Lys His Phe Lys Lys His Val Glu Glu Gln Leu Asn Lys Arg His Gly
                165                 170                 175

Gln Val Tyr Lys Lys Ala Phe Met Gln Val Val Glu Ala Asp Met Ile
            180                 185                 190

Gly Arg Gly Leu Leu Gly Gly Glu Ala Trp Ser Ser Trp Asp Lys Glu
        195                 200                 205

Thr Thr Met His Val Gly Ile Arg Leu Ile Glu Met Leu Ile Glu Ser
```

-continued

```
            210                 215                 220
Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
                245                 250                 255

Lys Arg Ala Gly Ala Leu Ala Gly Ile Ser Pro Met Phe Gln Pro Cys
                260                 265                 270

Val Val Pro Pro Lys Pro Trp Val Ala Ile Thr Gly Gly Gly Tyr Trp
            275                 280                 285

Ala Asn Gly Arg Arg Pro Leu Ala Leu Val Arg Thr His Ser Lys Lys
290                 295                 300

Gly Leu Met Arg Tyr Glu Asp Val Tyr Met Pro Glu Val Tyr Lys Ala
305                 310                 315                 320

Val Asn Leu Ala Gln Asn Thr Ala Trp Lys Ile Asn Lys Lys Val Leu
                325                 330                 335

Ala Val Val Asn Glu Ile Val Asn Trp Lys Asn Cys Pro Val Ala Asp
                340                 345                 350

Ile Pro Ser Leu Glu Arg Gln Glu Leu Pro Pro Lys Pro Asp Asp Ile
                355                 360                 365

Asp Thr Asn Glu Ala Ala Leu Lys Glu Trp Lys Lys Ala Ala Ala Gly
370                 375                 380

Ile Tyr Arg Leu Asp Lys Ala Arg Val Ser Arg Ile Ser Leu Glu
385                 390                 395                 400

Phe Met Leu Glu Gln Ala Asn Lys Phe Ala Ser Lys Lys Ala Ile Trp
                405                 410                 415

Phe Pro Tyr Asn Met Asp Trp Arg Gly Arg Val Tyr Ala Val Pro Met
                420                 425                 430

Phe Asn Pro Gln Gly Asn Asp Met Thr Lys Gly Leu Leu Thr Leu Ala
                435                 440                 445

Lys Gly Lys Pro Ile Gly Glu Gly Phe Tyr Trp Leu Lys Ile His
                450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
                485                 490                 495

Pro Ile Asn Asn Thr Trp Trp Ala Glu Gln Asp Ser Pro Phe Cys Phe
                500                 505                 510

Leu Ala Phe Cys Phe Glu Tyr Ala Gly Val Thr His His Gly Leu Ser
                515                 520                 525

Tyr Asn Cys Ser Leu Pro Leu Ala Phe Asp Gly Ser Cys Ser Gly Ile
                530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
                565                 570                 575

Gln Lys Val Asn Glu Ile Leu Lys Gln Asp Ala Ile Asn Gly Thr Pro
                580                 585                 590

Asn Glu Met Ile Thr Val Thr Asp Lys Asp Thr Gly Glu Ile Ser Glu
                595                 600                 605

Lys Leu Lys Leu Gly Thr Ser Thr Leu Ala Gln Gln Trp Leu Ala Tyr
                610                 615                 620

Gly Val Thr Arg Ser Val Thr Lys Arg Ser Val Met Thr Leu Ala Tyr
625                 630                 635                 640
```

-continued

```
Gly Ser Lys Glu Phe Gly Phe Arg Gln Gln Val Leu Asp Asp Thr Ile
                645                 650                 655
Gln Pro Ala Ile Asp Ser Gly Lys Gly Leu Met Phe Thr Gln Pro Asn
            660                 665                 670
Gln Ala Ala Gly Tyr Met Ala Lys Leu Ile Trp Asp Ala Val Ser Val
        675                 680                 685
Thr Val Ala Ala Val Glu Ala Met Asn Trp Leu Lys Ser Ala Ala
    690                 695                 700
Lys Leu Leu Ala Ala Glu Val Lys Asp Lys Lys Thr Lys Glu Ile Leu
705                 710                 715                 720
Arg His Arg Cys Ala Val His Trp Thr Thr Pro Asp Gly Phe Pro Val
                725                 730                 735
Trp Gln Glu Tyr Arg Lys Pro Leu Gln Lys Arg Leu Asp Met Ile Phe
            740                 745                 750
Leu Gly Gln Phe Arg Leu Gln Pro Thr Ile Asn Thr Leu Lys Asp Ser
        755                 760                 765
Gly Ile Asp Ala His Lys Gln Glu Ser Gly Ile Ala Pro Asn Phe Val
    770                 775                 780
His Ser Gln Asp Gly Ser His Leu Arg Met Thr Val Val Tyr Ala His
785                 790                 795                 800
Glu Lys Tyr Gly Ile Glu Ser Phe Ala Leu Ile His Asp Ser Phe Gly
                805                 810                 815
Thr Ile Pro Ala Asp Ala Gly Lys Leu Phe Lys Ala Val Arg Glu Thr
            820                 825                 830
Met Val Ile Thr Tyr Glu Asn Asn Asp Val Leu Ala Asp Phe Tyr Ser
        835                 840                 845
Gln Phe Ala Asp Gln Leu His Glu Thr Gln Leu Asp Lys Met Pro Pro
    850                 855                 860
Leu Pro Lys Lys Gly Asn Leu Asn Leu Gln Asp Ile Leu Lys Ser Asp
865                 870                 875                 880
Phe Ala Phe Ala
```

<210> SEQ ID NO 5
<211> LENGTH: 906
<212> TYPE: PRT
<213> ORGANISM: Bacteriophage K11
<220> FEATURE:
<221> NAME/KEY: VARIANT
<222> LOCATION: 77, 78, 79, 157, 158, 159, 236, 237, 238, 456, 457, 458,
      533, 534, 535, 608, 609, 610, 687, 688, 689, 762, 763, 764,
      842, 843, 844
<223> OTHER INFORMATION: Xaa = Any Amino Acid

<400> SEQUENCE: 5

```
Met Asn Ala Leu Asn Ile Gly Arg Asn Asp Phe Ser Glu Ile Glu Leu
1               5                   10                  15
Ala Ala Ile Pro Tyr Asn Ile Leu Ser Glu His Tyr Gly Asp Gln Ala
            20                  25                  30
Ala Arg Glu Gln Leu Ala Leu Glu His Glu Ala Tyr Glu Leu Gly Arg
        35                  40                  45
Gln Arg Phe Leu Lys Met Leu Glu Arg Gln Val Lys Ala Gly Glu Phe
    50                  55                  60
Ala Asp Asn Ala Ala Ala Lys Pro Leu Val Leu Thr Xaa Xaa Xaa Gln
65                  70                  75                  80
Leu Thr Lys Arg Ile Asp Asp Trp Lys Glu Gln Ala Asn Ala Arg
                85                  90                  95
```

```
Gly Lys Lys Pro Arg Ala Tyr Tyr Pro Ile Lys His Gly Val Ala Ser
            100                 105                 110

Glu Leu Ala Val Ser Met Gly Ala Glu Val Leu Lys Glu Lys Arg Gly
            115                 120                 125

Val Ser Ser Glu Ala Ile Ala Leu Leu Thr Ile Lys Val Val Leu Gly
            130                 135                 140

Asn Ala His Arg Pro Leu Lys Gly His Asn Pro Ala Xaa Xaa Xaa Gln
145                 150                 155                 160

Leu Gly Lys Ala Leu Glu Asp Glu Ala Arg Phe Gly Arg Ile Arg Glu
                165                 170                 175

Gln Glu Ala Ala Tyr Phe Lys Lys Asn Val Ala Asp Gln Leu Asp Lys
            180                 185                 190

Arg Val Gly His Val Tyr Lys Lys Ala Phe Met Gln Val Glu Ala
            195                 200                 205

Asp Met Ile Ser Lys Gly Met Leu Gly Gly Asp Asn Trp Ala Ser Trp
    210                 215                 220

Lys Thr Asp Glu Gln Met His Val Gly Thr Lys Xaa Xaa Xaa Leu Leu
225                 230                 235                 240

Ile Glu Gly Thr Gly Leu Val Glu Met Thr Lys Asn Lys Met Ala Asp
                245                 250                 255

Gly Ser Asp Asp Val Thr Ser Met Gln Met Val Gln Leu Ala Pro Ala
            260                 265                 270

Phe Val Glu Leu Leu Ser Lys Arg Ala Gly Ala Leu Ala Gly Ile Ser
            275                 280                 285

Pro Met His Gln Pro Cys Val Val Pro Pro Lys Pro Trp Val Glu Thr
    290                 295                 300

Val Gly Gly Gly Tyr Trp Ser Val Gly Arg Arg Pro Leu Ala Leu Val
305                 310                 315                 320

Arg Thr His Ser Lys Lys Ala Leu Arg Arg Tyr Ala Asp Val His Met
                325                 330                 335

Pro Glu Val Tyr Lys Ala Val Asn Leu Ala Gln Asn Thr Pro Trp Lys
            340                 345                 350

Val Asn Lys Lys Val Leu Ala Val Asn Glu Ile Val Asn Trp Lys
            355                 360                 365

His Cys Pro Val Gly Asp Val Pro Ala Ile Glu Arg Glu Glu Leu Pro
    370                 375                 380

Pro Arg Pro Asp Asp Ile Asp Thr Asn Glu Val Ala Arg Lys Ala Trp
385                 390                 395                 400

Arg Lys Glu Ala Ala Ala Val Tyr Arg Lys Asp Lys Ala Arg Gln Ser
                405                 410                 415

Arg Arg Cys Arg Cys Glu Phe Met Val Ala Gln Ala Asn Lys Phe Ala
            420                 425                 430

Asn His Lys Ala Ile Trp Phe Pro Tyr Asn Met Asp Trp Arg Gly Arg
    435                 440                 445

Val Tyr Ala Val Ser Met Phe Xaa Xaa Xaa Gly Asn Asp Met Thr Lys
    450                 455                 460

Gly Ser Leu Thr Leu Ala Lys Gly Lys Pro Ile Gly Leu Asp Gly Phe
465                 470                 475                 480

Tyr Trp Leu Lys Ile His Gly Ala Asn Cys Ala Gly Val Asp Lys Val
                485                 490                 495

Pro Phe Pro Glu Arg Ile Lys Phe Ile Glu Glu Asn Glu Gly Asn Ile
            500                 505                 510
```

```
Leu Ala Ser Ala Ala Asp Pro Leu Asn Asn Thr Trp Trp Thr Gln Gln
            515                 520                 525

Asp Ser Pro Phe Xaa Xaa Xaa Ala Phe Cys Phe Glu Tyr Ala Gly Val
            530                 535                 540

Lys His His Gly Leu Asn Tyr Asn Cys Ser Leu Pro Leu Ala Phe Asp
545                 550                 555                 560

Gly Ser Cys Ser Gly Ile Gln His Phe Ser Ala Met Leu Arg Asp Ser
                565                 570                 575

Ile Gly Gly Arg Ala Val Asn Leu Leu Pro Ser Asp Thr Val Gln Asp
            580                 585                 590

Ile Tyr Lys Ile Val Ala Asp Lys Val Asn Glu Val Leu His Gln Xaa
            595                 600                 605

Xaa Xaa Asn Gly Ser Gln Thr Val Val Glu Gln Ile Ala Asp Lys Glu
    610                 615                 620

Thr Gly Glu Phe His Glu Lys Val Thr Leu Gly Glu Ser Val Leu Ala
625                 630                 635                 640

Ala Gln Trp Leu Gln Tyr Gly Val Thr Arg Lys Val Thr Lys Arg Ser
                645                 650                 655

Val Met Thr Leu Ala Tyr Gly Ser Lys Glu Ser Leu Val Arg Gln Gln
            660                 665                 670

Val Leu Glu Asp Thr Ile Gln Pro Ala Ile Asp Asn Gly Glu Xaa Xaa
            675                 680                 685

Xaa Phe Thr His Pro Asn Gln Ala Ala Gly Tyr Met Ala Lys Leu Ile
    690                 695                 700

Trp Asp Ala Val Thr Val Thr Val Val Ala Ala Val Glu Ala Met Asn
705                 710                 715                 720

Trp Leu Lys Ser Ala Ala Lys Leu Leu Ala Ala Glu Val Lys Asp Lys
                725                 730                 735

Lys Thr Lys Glu Val Leu Arg Lys Arg Cys Ala Ile His Trp Val Thr
            740                 745                 750

Pro Asp Gly Phe Pro Val Trp Gln Glu Xaa Xaa Xaa Gln Asn Gln Ala
            755                 760                 765

Arg Leu Lys Leu Val Phe Leu Gly Gln Ala Asn Val Lys Met Thr Tyr
            770                 775                 780

Asn Thr Gly Lys Asp Ser Glu Ile Asp Ala His Lys Gln Glu Ser Gly
785                 790                 795                 800

Ile Ala Pro Asn Phe Val His Ser Gln Asp Gly Ser His Leu Arg Met
                805                 810                 815

Thr Val Val His Ala Asn Glu Val Tyr Gly Ile Asp Ser Phe Ala Leu
            820                 825                 830

Ile His Asp Ser Ser Gly Thr Ile Pro Xaa Xaa Xaa Gly Asn Leu Phe
            835                 840                 845

Lys Ala Val Arg Glu Thr Met Val Lys Thr Tyr Glu Asp Asn Asp Val
850                 855                 860

Ile Ala Asp Phe Tyr Asp Gln Phe Ala Asp Gln Leu His Glu Ser Gln
865                 870                 875                 880

Leu Asp Lys Met Pro Ala Val Pro Ala Lys Gly Asp Leu Asn Leu Arg
                885                 890                 895

Asp Ile Leu Glu Ser Asp Phe Ala Phe Ala
            900                 905

<210> SEQ ID NO 6
<211> LENGTH: 874
<212> TYPE: PRT
```

-continued

```
<213> ORGANISM: Bacteriophage SP6
<220> FEATURE:
<221> NAME/KEY: VARIANT
<222> LOCATION: 49, 50, 51, 107, 108, 109, 186, 187, 188, 265, 266, 267,
      344, 345, 346, 424, 425, 426, 504, 505, 506, 579, 580, 657,
      658, 659, 737, 738, 739, 813, 814, 815
<223> OTHER INFORMATION: Xaa = Any Amino Acid

<400> SEQUENCE: 6
```

| Met | Gln | Asp | Leu | His | Ala | Ile | Gln | Leu | Gln | Leu | Glu | Glu | Glu | Met | Phe |
|---|---|---|---|---|---|---|---|---|---|---|---|---|---|---|---|
| 1 | | | | 5 | | | | | 10 | | | | | 15 | |

| Asn | Gly | Gly | Ile | Arg | Arg | Phe | Glu | Ala | Asp | Gln | Gln | Arg | Gln | Ile | Ala |
|---|---|---|---|---|---|---|---|---|---|---|---|---|---|---|---|
| | | | 20 | | | | | 25 | | | | | 30 | | |

| Ala | Gly | Ser | Glu | Ser | Asp | Thr | Ala | Trp | Asn | Arg | Arg | Leu | Leu | Ser | Glu |
|---|---|---|---|---|---|---|---|---|---|---|---|---|---|---|---|
| | | 35 | | | | | 40 | | | | | 45 | | | |

| Xaa | Xaa | Xaa | Pro | Met | Ala | Glu | Gly | Ile | Gln | Ala | Tyr | Lys | Glu | Glu | Tyr |
|---|---|---|---|---|---|---|---|---|---|---|---|---|---|---|---|
| 50 | | | | | 55 | | | | | 60 | | | | | |

| Glu | Gly | Lys | Lys | Gly | Arg | Ala | Pro | Arg | Ala | Leu | Ala | Phe | Leu | Gln | Cys |
|---|---|---|---|---|---|---|---|---|---|---|---|---|---|---|---|
| 65 | | | | 70 | | | | | 75 | | | | | 80 | |

| Val | Glu | Asn | Glu | Val | Ala | Ala | Tyr | Ile | Thr | Met | Lys | Val | Val | Met | Asp |
|---|---|---|---|---|---|---|---|---|---|---|---|---|---|---|---|
| | | | 85 | | | | | 90 | | | | | 95 | | |

| Met | Leu | Asn | Thr | Asp | Ala | Thr | Leu | Gln | Ala | Xaa | Xaa | Xaa | Ser | Val | Ala |
|---|---|---|---|---|---|---|---|---|---|---|---|---|---|---|---|
| | | | 100 | | | | | 105 | | | | | 110 | | |

| Glu | Arg | Ile | Glu | Asp | Gln | Val | Arg | Phe | Ser | Lys | Leu | Glu | Gly | His | Ala |
|---|---|---|---|---|---|---|---|---|---|---|---|---|---|---|---|
| | | 115 | | | | | 120 | | | | | 125 | | | |

| Ala | Lys | Tyr | Phe | Glu | Lys | Val | Lys | Lys | Ser | Leu | Lys | Ala | Ser | Arg | Thr |
|---|---|---|---|---|---|---|---|---|---|---|---|---|---|---|---|
| | 130 | | | | | 135 | | | | | 140 | | | | |

| Lys | Ser | Tyr | Arg | His | Ala | His | Asn | Val | Ala | Val | Val | Ala | Glu | Lys | Ser |
|---|---|---|---|---|---|---|---|---|---|---|---|---|---|---|---|
| 145 | | | | | 150 | | | | | 155 | | | | | 160 |

| Val | Ala | Glu | Lys | Asp | Ala | Asp | Phe | Asp | Arg | Trp | Glu | Ala | Trp | Pro | Lys |
|---|---|---|---|---|---|---|---|---|---|---|---|---|---|---|---|
| | | | 165 | | | | | 170 | | | | | 175 | | |

| Glu | Thr | Gln | Leu | Gln | Ile | Gly | Thr | Thr | Xaa | Xaa | Xaa | Ile | Leu | Glu | Gly |
|---|---|---|---|---|---|---|---|---|---|---|---|---|---|---|---|
| | | | 180 | | | | | 185 | | | | | 190 | | |

| Ser | Val | Phe | Tyr | Asn | Gly | Glu | Pro | Val | Phe | Met | Arg | Ala | Met | Arg | Thr |
|---|---|---|---|---|---|---|---|---|---|---|---|---|---|---|---|
| | 195 | | | | | 200 | | | | | 205 | | | | |

| Tyr | Gly | Gly | Lys | Thr | Ile | Tyr | Tyr | Leu | Gln | Thr | Ser | Glu | Ser | Val | Gly |
|---|---|---|---|---|---|---|---|---|---|---|---|---|---|---|---|
| 210 | | | | | 215 | | | | | 220 | | | | | |

| Gln | Trp | Ile | Ser | Ala | Phe | Lys | Glu | His | Val | Ala | Gln | Leu | Ser | Pro | Ala |
|---|---|---|---|---|---|---|---|---|---|---|---|---|---|---|---|
| 225 | | | | | 230 | | | | | 235 | | | | | 240 |

| Tyr | Ala | Pro | Cys | Val | Ile | Pro | Pro | Arg | Pro | Trp | Arg | Thr | Pro | Phe | Asn |
|---|---|---|---|---|---|---|---|---|---|---|---|---|---|---|---|
| | | | 245 | | | | | 250 | | | | | 255 | | |

| Gly | Gly | Phe | His | Thr | Glu | Lys | Val | Xaa | Xaa | Xaa | Ile | Arg | Leu | Val | Lys |
|---|---|---|---|---|---|---|---|---|---|---|---|---|---|---|---|
| | | | 260 | | | | | 265 | | | | | 270 | | |

| Gly | Asn | Arg | Glu | His | Val | Arg | Lys | Leu | Thr | Gln | Lys | Gln | Met | Pro | Lys |
|---|---|---|---|---|---|---|---|---|---|---|---|---|---|---|---|
| | | 275 | | | | | 280 | | | | | 285 | | | |

| Val | Tyr | Lys | Ala | Ile | Asn | Ala | Leu | Gln | Asn | Thr | Gln | Trp | Gln | Ile | Asn |
|---|---|---|---|---|---|---|---|---|---|---|---|---|---|---|---|
| | 290 | | | | | 295 | | | | | 300 | | | | |

| Lys | Asp | Val | Leu | Ala | Val | Ile | Glu | Glu | Val | Ile | Arg | Leu | Asp | Leu | Gly |
|---|---|---|---|---|---|---|---|---|---|---|---|---|---|---|---|
| 305 | | | | | 310 | | | | | 315 | | | | | 320 |

| Tyr | Gly | Val | Pro | Ser | Phe | Lys | Pro | Leu | Ile | Asp | Lys | Glu | Asn | Lys | Pro |
|---|---|---|---|---|---|---|---|---|---|---|---|---|---|---|---|
| | | | 325 | | | | | 330 | | | | | 335 | | |

| Ala | Asn | Pro | Val | Pro | Val | Glu | Xaa | Xaa | Xaa | Leu | Arg | Gly | Arg | Glu | Leu |
|---|---|---|---|---|---|---|---|---|---|---|---|---|---|---|---|
| | | | 340 | | | | | 345 | | | | | 350 | | |

| Lys | Glu | Met | Leu | Ser | Pro | Glu | Gln | Trp | Gln | Gln | Phe | Ile | Asn | Trp | Lys |
|---|---|---|---|---|---|---|---|---|---|---|---|---|---|---|---|
| | | 355 | | | | | 360 | | | | | 365 | | | |

```
Gly Glu Cys Ala Arg Leu Tyr Thr Ala Glu Thr Lys Arg Gly Ser Lys
        370                 375                 380

Ser Ala Ala Val Val Arg Met Val Gly Gln Ala Arg Lys Tyr Ser Ala
385                 390                 395                 400

Phe Glu Ser Ile Tyr Phe Val Tyr Ala Met Asp Ser Arg Ser Arg Val
                405                 410                 415

Tyr Val Gln Ser Ser Thr Leu Xaa Xaa Xaa Ser Asn Asp Leu Gly Lys
            420                 425                 430

Ala Leu Leu Arg Phe Thr Glu Gly Arg Pro Val Asn Gly Val Glu Ala
            435                 440                 445

Leu Lys Trp Phe Cys Ile Asn Gly Ala Asn Leu Trp Gly Trp Asp Lys
        450                 455                 460

Lys Thr Phe Asp Val Arg Val Ser Asn Val Leu Asp Glu Glu Phe Gln
465                 470                 475                 480

Asp Met Cys Arg Asp Ile Ala Ala Asp Pro Leu Thr Phe Thr Gln Trp
                485                 490                 495

Ala Lys Ala Asp Ala Pro Tyr Xaa Xaa Xaa Ala Trp Cys Phe Glu Tyr
            500                 505                 510

Ala Gln Tyr Leu Asp Leu Val Asp Glu Gly Arg Ala Asp Glu Phe Arg
            515                 520                 525

Thr His Leu Pro Val His Gln Asp Gly Ser Cys Ser Gly Ile Gln His
        530                 535                 540

Tyr Ser Ala Met Leu Arg Asp Glu Val Gly Ala Lys Ala Val Asn Leu
545                 550                 555                 560

Lys Pro Ser Asp Ala Pro Gln Asp Ile Tyr Gly Ala Val Ala Gln Val
                565                 570                 575

Val Ile Xaa Xaa Asn Ala Leu Tyr Met Asp Ala Asp Asp Ala Thr Thr
            580                 585                 590

Phe Thr Ser Gly Ser Val Thr Leu Ser Gly Thr Glu Leu Arg Ala Met
        595                 600                 605

Ala Ser Ala Trp Asp Ser Ile Gly Ile Thr Arg Ser Leu Thr Lys Lys
        610                 615                 620

Pro Val Met Thr Leu Pro Tyr Gly Ser Thr Arg Leu Thr Cys Arg Glu
625                 630                 635                 640

Ser Val Ile Asp Tyr Ile Val Asp Leu Glu Glu Lys Glu Ala Gln Lys
                645                 650                 655

Xaa Xaa Xaa Glu Gly Arg Thr Ala Asn Lys Val His Pro Phe Glu Asp
            660                 665                 670

Asp Arg Gln Asp Tyr Leu Thr Pro Gly Ala Ala Tyr Asn Tyr Met Thr
        675                 680                 685

Ala Leu Ile Trp Pro Ser Ile Ser Glu Val Val Lys Ala Pro Ile Val
        690                 695                 700

Ala Met Lys Met Ile Arg Gln Leu Ala Arg Phe Ala Ala Lys Arg Asn
705                 710                 715                 720

Glu Gly Leu Met Tyr Thr Leu Pro Thr Gly Phe Ile Leu Glu Gln Lys
                725                 730                 735

Xaa Xaa Xaa Thr Glu Met Leu Arg Val Arg Thr Cys Leu Met Gly Asp
            740                 745                 750

Ile Lys Met Ser Leu Gln Val Glu Thr Asp Ile Val Asp Glu Ala Ala
            755                 760                 765

Met Met Gly Ala Ala Ala Pro Asn Phe Val His Gly His Asp Ala Ser
        770                 775                 780

His Leu Ile Leu Thr Val Cys Glu Leu Val Asp Lys Gly Val Thr Ser
```

-continued

```
                785                 790                 795                 800
Ile Ala Val Ile His Asp Ser Phe Gly Thr His Ala Xaa Xaa Xaa Leu
                    805                 810                 815
Thr Leu Arg Val Ala Leu Lys Gly Gln Met Val Ala Met Tyr Ile Asp
                820                 825                 830
Gly Asn Ala Leu Gln Lys Leu Leu Glu Glu His Glu Val Arg Trp Met
                835                 840                 845
Val Asp Thr Gly Ile Glu Val Pro Glu Gln Gly Glu Phe Asp Leu Asn
            850                 855                 860
Glu Ile Met Asp Ser Glu Tyr Val Phe Ala
865                 870

<210> SEQ ID NO 7
<211> LENGTH: 78
<212> TYPE: PRT
<213> ORGANISM: Bacteriophage T7

<400> SEQUENCE: 7

Tyr Gly Val Thr Arg Ser Val Thr Lys Arg Ser Val Met Thr Leu Ala
1               5                   10                  15
Tyr Gly Ser Lys Glu Phe Gly Phe Arg Gln Gln Val Leu Glu Asp Thr
                20                  25                  30
Ile Gln Pro Ala Ile Asp Ser Gly Lys Gly Leu Met Phe Thr Gln Pro
            35                  40                  45
Asn Gln Ala Ala Gly Tyr Met Ala Lys Leu Ile Trp Glu Ser Val Ser
        50                  55                  60
Val Thr Val Val Ala Ala Val Glu Ala Met Asn Trp Leu Lys
65                  70                  75

<210> SEQ ID NO 8
<211> LENGTH: 78
<212> TYPE: PRT
<213> ORGANISM: Bacteriophage T7
<220> FEATURE:
<221> NAME/KEY: PEPTIDE
<222> LOCATION: (1)..(78)
<223> OTHER INFORMATION: Mutant T7 RNA polymerase F644Y.

<400> SEQUENCE: 8

Tyr Gly Val Thr Arg Ser Val Thr Lys Arg Ser Val Met Thr Leu Ala
1               5                   10                  15
Tyr Gly Ser Lys Glu Tyr Gly Phe Arg Gln Gln Val Leu Glu Asp Thr
                20                  25                  30
Ile Gln Pro Ala Ile Asp Ser Gly Lys Gly Leu Met Phe Thr Gln Pro
            35                  40                  45
Asn Gln Ala Ala Gly Tyr Met Ala Lys Leu Thr Trp Glu Ser Val Ser
        50                  55                  60
Val Thr Val Val Ala Ala Val Glu Ala Met Asn Trp Leu Lys
65                  70                  75

<210> SEQ ID NO 9
<211> LENGTH: 78
<212> TYPE: PRT
<213> ORGANISM: Bacteriophage T7
<220> FEATURE:
<221> NAME/KEY: PEPTIDE
<222> LOCATION: (1)..(78)
<223> OTHER INFORMATION: Mutant T7 RNA polymerase F646Y.

<400> SEQUENCE: 9
```

-continued

Tyr Gly Val Thr Arg Ser Val Thr Lys Arg Ser Val Met Thr Leu Ala
1               5                   10                  15

Tyr Gly Ser Lys Glu Phe Gly Tyr Arg Gln Gln Val Leu Glu Asp Thr
            20                  25                  30

Ile Gln Pro Ala Ile Asp Ser Gly Lys Gly Leu Met Phe Thr Gln Pro
        35                  40                  45

Asn Gln Ala Ala Gly Tyr Met Ala Lys Leu Ile Trp Glu Ser Val Ser
    50                  55                  60

Val Thr Val Val Ala Ala Val Glu Ala Met Asn Trp Leu Lys
65                  70                  75

<210> SEQ ID NO 10
<211> LENGTH: 78
<212> TYPE: PRT
<213> ORGANISM: Bacteriophage T7
<220> FEATURE:
<221> NAME/KEY: PEPTIDE
<222> LOCATION: (1)..(78)
<223> OTHER INFORMATION: Mutant T7 RNA polymerase L665P/F667Y.

<400> SEQUENCE: 10

Tyr Gly Val Thr Arg Ser Val Thr Lys Arg Ser Val Met Thr Leu Ala
1               5                   10                  15

Tyr Gly Ser Lys Glu Phe Gly Phe Arg Gln Gln Val Leu Glu Asp Thr
            20                  25                  30

Ile Gln Pro Ala Ile Asp Ser Gly Lys Gly Pro Met Tyr Thr Gln Pro
        35                  40                  45

Asn Gln Ala Ala Gly Tyr Met Ala Lys Leu Ile Trp Glu Ser Val Ser
    50                  55                  60

Val Thr Val Val Ala Ala Val Glu Ala Met Asn Trp Leu Lys
65                  70                  75

<210> SEQ ID NO 11
<211> LENGTH: 73
<212> TYPE: PRT
<213> ORGANISM: Bacteriophage T7

<400> SEQUENCE: 11

Ala Gly Gln Trp Leu Ala Tyr Gly Val Thr Arg Ser Val Thr Lys Arg
1               5                   10                  15

Ser Val Met Thr Leu Ala Tyr Gly Ser Lys Glu Phe Gly Phe Arg Gln
            20                  25                  30

Gln Val Leu Glu Asp Thr Ile Gln Pro Ala Ile Asp Ser Gly Lys Gly
        35                  40                  45

Leu Met Phe Thr Gln Pro Asn Gln Ala Ala Gly Tyr Met Ala Lys Leu
    50                  55                  60

Ile Trp Glu Ser Val Ser Val Thr Val
65                  70

<210> SEQ ID NO 12
<211> LENGTH: 73
<212> TYPE: PRT
<213> ORGANISM: Bacteriophage T7
<220> FEATURE:
<221> NAME/KEY: PEPTIDE
<222> LOCATION: (1)..(73)
<223> OTHER INFORMATION: Mutant T7 RNA polymerase F644Y.

<400> SEQUENCE: 12

Ala Gly Gln Trp Leu Ala Tyr Gly Val Thr Arg Ser Val Thr Lys Arg
1               5                   10                  15

-continued

Ser Val Met Thr Leu Ala Tyr Gly Ser Lys Glu Tyr Gly Phe Arg Gln
             20                  25                  30

Gln Val Leu Glu Asp Thr Ile Gln Pro Ala Ile Asp Ser Gly Lys Gly
         35                  40                  45

Leu Met Phe Thr Gln Pro Asn Gln Ala Ala Gly Tyr Met Ala Lys Leu
     50                  55                  60

Ile Trp Glu Ser Val Ser Val Thr Val
65                  70

<210> SEQ ID NO 13
<211> LENGTH: 73
<212> TYPE: PRT
<213> ORGANISM: Bacteriophage T7
<220> FEATURE:
<221> NAME/KEY: PEPTIDE
<222> LOCATION: (1)..(73)
<223> OTHER INFORMATION: Mutant T7 RNA polymerase L665P/F667Y.

<400> SEQUENCE: 13

Ala Gly Gln Trp Leu Ala Tyr Gly Val Thr Arg Ser Val Thr Lys Arg
1               5                   10                  15

Ser Val Met Thr Leu Ala Tyr Gly Ser Lys Glu Phe Gly Phe Arg Gln
             20                  25                  30

Gln Val Leu Glu Asp Thr Ile Gln Pro Ala Ile Asp Ser Gly Lys Gly
         35                  40                  45

Pro Met Tyr Thr Gln Pro Asn Gln Ala Ala Gly Tyr Met Ala Lys Leu
     50                  55                  60

Ile Trp Glu Ser Val Ser Val Thr Val
65                  70

<210> SEQ ID NO 14
<211> LENGTH: 73
<212> TYPE: PRT
<213> ORGANISM: Bacteriophage T3

<400> SEQUENCE: 14

Ala Gln Gln Trp Leu Ala Tyr Gly Val Thr Arg Ser Val Thr Lys Arg
1               5                   10                  15

Ser Val Met Thr Leu Ala Tyr Gly Ser Lys Glu Phe Gly Phe Arg Gln
             20                  25                  30

Gln Val Leu Asp Asp Thr Ile Gln Pro Ala Ile Asp Ser Gly Lys Gly
         35                  40                  45

Leu Met Phe Thr Gln Pro Asn Gln Ala Ala Gly Tyr Met Ala Lys Leu
     50                  55                  60

Ile Trp Asp Ala Val Ser Val Thr Val
65                  70

<210> SEQ ID NO 15
<211> LENGTH: 73
<212> TYPE: PRT
<213> ORGANISM: Bacteriophage K11

<400> SEQUENCE: 15

Ala Ala Gln Trp Leu Gln Tyr Gly Val Thr Arg Lys Val Thr Lys Arg
1               5                   10                  15

Ser Val Met Thr Leu Ala Tyr Gly Ser Lys Glu Ser Leu Val Arg Gln
             20                  25                  30

Gln Val Leu Glu Asp Thr Ile Gln Pro Ala Ile Asp Asn Gly Glu Gly
         35                  40                  45

```
Leu Met Phe Thr His Pro Asn Gln Ala Ala Gly Tyr Met Ala Lys Leu
      50                  55                  60

Ile Trp Asp Ala Val Thr Val Thr Val
 65                  70
```

<210> SEQ ID NO 16
<211> LENGTH: 75
<212> TYPE: PRT <
<213> ORGANISM: Bacteriophage SP6

<400> SEQUENCE: 16

```
Ala Ser Ala Trp Asp Ser Ile Gly Ile Thr Arg Ser Leu Thr Lys Lys
 1               5                  10                  15

Pro Val Met Thr Leu Pro Tyr Gly Ser Thr Arg Leu Thr Cys Arg Glu
              20                  25                  30

Ser Val Ile Asp Tyr Ile Val Asp Leu Glu Glu Lys Glu Ala Gln Lys
          35                  40                  45

Ala Val Ala Glu Gly Arg Thr Ala Asn Lys Val His Pro Phe Glu Asp
      50                  55                  60

Asp Arg Gln Asp Tyr Leu Thr Pro Gly Ala Ala
 65                  70                  75
```

<210> SEQ ID NO 17
<211> LENGTH: 31
<212> TYPE: DNA
<213> ORGANISM: Bacteriophage T7
<220> FEATURE:
<221> NAME/KEY: misc_feature
<222> LOCATION: (1)..(31)
<223> OTHER INFORMATION: Mutant T7 RNA polymerase wild type.
<220> FEATURE:
<221> NAME/KEY: misc_feature
<222> LOCATION: (25)..(25)
<223> OTHER INFORMATION: Nucleotide 25 is "n" wherein "n" = any
      nucleotide.

<400> SEQUENCE: 17 gggaggggggg gggggggggcc ccccngggcg t                               31

<210> SEQ ID NO 18
<211> LENGTH: 32
<212> TYPE: DNA
<213> ORGANISM: Bacteriophage T7
<220> FEATURE:
<221> NAME/KEY: misc_feature
<222> LOCATION: (1)..(32)
<223> OTHER INFORMATION: Mutant T7 RNA polymerase wild type.
<220> FEATURE:
<221> NAME/KEY: misc_feature
<222> LOCATION: (1)..(32)
<223> OTHER INFORMATION: Nucleotides 6-8, 18, 25-30 are "n" wherein "n"
      = any nucleotide.

<400> SEQUENCE: 18
gcgtcnnnaa aacgcacntt ttctntcgtn gg                                32

<210> SEQ ID NO 19
<211> LENGTH: 19
<212> TYPE: DNA
<213> ORGANISM: Bacteriophage T7
<220> FEATURE:
<221> NAME/KEY: misc_feature
<222> LOCATION: (1)..(19)
<223> OTHER INFORMATION: Mutant T7 RNA polymerase F644Y.

<400> SEQUENCE: 19 cgagggggggg ccggtaccc                                                    19

<210> SEQ ID NO 20
<211> LENGTH: 25
<212> TYPE: DNA
<213> ORGANISM: Bacteriophage T7
<220> FEATURE:
<221> NAME/KEY: misc_feature
<222> LOCATION: (1)..(25)
<223> OTHER INFORMATION: Mutant T7 RNA polymerase F644Y.
<220> FEATURE:
<221> NAME/KEY: misc_feature
<222> LOCATION: (6)..(6)
<223> OTHER INFORMATION: Nucleotide 6 is "n" wherein "n" = any
      nucleotide.

<400> SEQUENCE: 20
cccctntttg ttcctttagt gaggt                                              25

<210> SEQ ID NO 21
<211> LENGTH: 18
<212> TYPE: DNA
<213> ORGANISM: Bacteriophage T7
<220> FEATURE:
<221> NAME/KEY: misc_feature
<222> LOCATION: (1)..(18)
<223> OTHER INFORMATION: Mutant T7 RNA polymerase F667Y.

<400> SEQUENCE: 21
gaggggggcc ggtaacgc                                                      18

<210> SEQ ID NO 22
<211> LENGTH: 22
<212> TYPE: DNA
<213> ORGANISM: Bacteriophage T7
<220> FEATURE:
<221> NAME/KEY: misc_feature
<222> LOCATION: (1)..(22)
<223> OTHER INFORMATION: Mutant T7 RNA polymerase F667Y.

<400> SEQUENCE: 22
acgccttttg ttccctttag tg                                                 22

<210> SEQ ID NO 23
<211> LENGTH: 569
<212> TYPE: DNA
<213> ORGANISM: Bacteriophage T7
<220> FEATURE:
<221> NAME/KEY: misc_feature
<222> LOCATION: (1)..(569)
<223> OTHER INFORMATION: Mutant T7 RNA polymerase F644Y/L665P/F667Y.
<220> FEATURE:
<221> NAME/KEY: misc_feature
<222> LOCATION: (1)..(472)
<223> OTHER INFORMATION: Nucleotides 1-14, 17-18, 21, 26, 29, 34, 38, 4
      0, 50-51, 53, 58, 75-76, 85, 110, 117, 132, 142, 150, 157, 399,
      440 and 472 are "n"wherein "n" = any nucleotide

<400> SEQUENCE: 23
nnnnnnnnnn nnnnggnnnn ngnnngt nggttncgna tccnaaangn aacagggggn nantgtgnaa   60
acatgaatat ttttnntaag ctttnattcc aggcaagac attttaaccn aaattgncaa          120
attatatcac tnattagaca gnaaaatctn acccagntaa gacttctgga ggtttggtac         180
agtagtttgt cttggatgct tcatgtatgc agtcacttat agtcagtatt gcacttggca        240
cacttcagct taaaccaaca ggataggaaa aataggggagc aacatggagt ggcatcctgg       300
tatttctaca gtcctgtaga tgaagtctct atatgtgcaa catcctggga cagagcatat        360

```
ttgggaagaa acagtttgcc attgaatccc gtgtcatana atatccagca cagatggtgg      420
tgttgatggt tagcaataan cacactctct cctttcgatg tgcattgtat antcaggtgg      480
atacaaaaag acatcgcttg gcccacatgc aaggccaaaa agcagacatc agaaagagag      540
cagtcatgtg ggggaattgg tccgactgc                                        569
```

<210> SEQ ID NO 24
<211> LENGTH: 50
<212> TYPE: DNA
<213> ORGANISM: Artificial Sequence
<220> FEATURE:
<223> OTHER INFORMATION: T7Rpol-N primer

<400> SEQUENCE: 24

```
atattttagc catggaggat tgatatatga acacgattaa catcgctaag              50
```

<210> SEQ ID NO 25
<211> LENGTH: 40
<212> TYPE: DNA
<213> ORGANISM: Artificial Sequence
<220> FEATURE:
<223> OTHER INFORMATION: T7Rpol-C primer

<400> SEQUENCE: 25

```
atattttagc catggtatag tgagtcgtat tgatttggcg                          40
```

<210> SEQ ID NO 26
<211> LENGTH: 26
<212> TYPE: DNA
<213> ORGANISM: Artificial Sequence
<220> FEATURE:
<223> OTHER INFORMATION: F646Y(+) primer

<400> SEQUENCE: 26

```
gttgacggaa gccgtactct ttggac                                         26
```

<210> SEQ ID NO 27
<211> LENGTH: 26
<212> TYPE: DNA
<213> ORGANISM: Artificial Sequence
<220> FEATURE:
<223> OTHER INFORMATION: F646Y(-) primer

<400> SEQUENCE: 27

```
gtccaaagag tacggcttcc gtcaac                                         26
```

<210> SEQ ID NO 28
<211> LENGTH: 23
<212> TYPE: DNA
<213> ORGANISM: Artificial Sequence
<220> FEATURE:
<223> OTHER INFORMATION: T7RNAP-HpaI-N primer

<400> SEQUENCE: 28

```
cgcgcggtta acttgcttcc tag                                            23
```

<210> SEQ ID NO 29
<211> LENGTH: 23
<212> TYPE: DNA
<213> ORGANISM: Artificial Sequence
<220> FEATURE:
<223> OTHER INFORMATION: pTrc99a-PstI-C primer

<400> SEQUENCE: 29

```
gcatgcctgc aggtcgactc tag                                              23

<210> SEQ ID NO 30
<211> LENGTH: 21
<212> TYPE: DNA
<213> ORGANISM: Artificial Sequence
<220> FEATURE:
<223> OTHER INFORMATION: ApaF1 primer

<400> SEQUENCE: 30
catctggtcg cattgggtca c                                                21

<210> SEQ ID NO 31
<211> LENGTH: 21
<212> TYPE: DNA
<213> ORGANISM: Artificial Sequence
<220> FEATURE:
<223> OTHER INFORMATION: Xho-R primer

<400> SEQUENCE: 31
ccaagtgttc tcgagtggag a                                                21

<210> SEQ ID NO 32
<211> LENGTH: 26
<212> TYPE: DNA
<213> ORGANISM: Artificial Sequence
<220> FEATURE:
<223> OTHER INFORMATION: Xho-F primer

<400> SEQUENCE: 32
ctaagtctcc actcgagaac acttgg                                           26

<210> SEQ ID NO 33
<211> LENGTH: 21
<212> TYPE: DNA
<213> ORGANISM: Artificial Sequence
<220> FEATURE:
<223> OTHER INFORMATION: AflII-R primer

<400> SEQUENCE: 33
cagccagcag cttagcagca g                                                21

<210> SEQ ID NO 34
<211> LENGTH: 21
<212> TYPE: DNA
<213> ORGANISM: Artificial Sequence
<220> FEATURE:
<223> OTHER INFORMATION: 667R primer

<400> SEQUENCE: 34
gctgagtgta catcggaccc t                                                21

<210> SEQ ID NO 35
<211> LENGTH: 21
<212> TYPE: DNA
<213> ORGANISM: Artificial Sequence
<220> FEATURE:
<223> OTHER INFORMATION: 667F primer

<400> SEQUENCE: 35
gctgagtgta catcggaccc t                                                21

<210> SEQ ID NO 36
<211> LENGTH: 21
<212> TYPE: DNA
<213> ORGANISM: Artificial Sequence
```

```
<220> FEATURE:
<223> OTHER INFORMATION: T7-DOUBLE-R primer

<400> SEQUENCE: 36
ctctttggac ccgtaagcca g                                    21

<210> SEQ ID NO 37
<211> LENGTH: 29
<212> TYPE: DNA
<213> ORGANISM: Artificial Sequence
<220> FEATURE:
<223> OTHER INFORMATION: T7-DOUBLE-F primer

<400> SEQUENCE: 37
ttacgggtcc aaagagtacg gcttccgtc                            29

<210> SEQ ID NO 38
<211> LENGTH: 19
<212> TYPE: DNA
<213> ORGANISM: Artificial Sequence
<220> FEATURE:
<223> OTHER INFORMATION: L220 primer

<400> SEQUENCE: 38
caatttcaca caggaaaca                                       19

<210> SEQ ID NO 39
<211> LENGTH: 22
<212> TYPE: DNA
<213> ORGANISM: Artificial Sequence
<220> FEATURE:
<223> OTHER INFORMATION: 1211 primer

<400> SEQUENCE: 39
acgttgtaaa acgacggcca gt                                   22
```

US 6,867,027 B1

RNA POLYMERASE

TECHNICAL FIELD

The present invention relates to mutant RNA polymerases useful for methods for determining nucleotide sequence of DNA and the like.

BACKGROUND ART

The polymerase chain reaction (PCR) method is an excellent method, and its utilization has expanded year by year [Randall K. Saiki et al. (1988) Science 239, 487–4911. In the PCR method, even one molecule of DNA fragment can be amplified. The method for sequencing PCR amplified products without cloning them (the direct sequencing method) is also a useful method [Corinne Wong et al. (1988) Nature, 330, 384–386. This technique does not require construction of libraries and screening of such libraries, and is a quick method capable of simultaneously obtaining sequence information of many samples.

However, the above direct sequencing method suffers from two major problems.

One is that primers and 2'-deoxyribonucleoside 5'-triphosphates (2'-dNTPs) not incorporated remain in a reaction system, and the remaining substances inhibit sequencing reactions. Therefore, in conventional methods, such primers and 2'-dNTPs must be removed from PCR products before sequencing. There are many methods for purification of PCR products and examples include purification by electrophoresis, ethanol precipitation, gel filtration and HPLC purification [see, for example, Dorit R. L. et al. (1991) Current Protocols in Molecular Biology, Vol. 11, John Wiley and Sons, New York, 15.2.1–15.2.11. However, these methods are complicated without exception.

The second problem is quick renaturation of PCR products. When the PCR products are renatured into a double-stranded DNA, they are no longer single-stranded templates, and annealing between primers and single-stranded templates is inhibited. As methods for minimizing the renaturation, quenching after denaturation, biotinylation of one primer and absorption of PCR products onto streptavidin-coated articles, use of exonuclease, asymmetric PCR and the like have been reported. See, for example, Barbara Bachmann et al., 1990, Nucleic Acid Res., 18, 1309-. However, most of these methods are time—consuming and very laborious.

Therefore, the present inventors proposed an absolutely novel method for determining nucleotide sequence of DNA for solving these problems. This method does not require removal of unreacted primers and 2'-deoxyribonucleoside 5' triphosphates (2'-dNTPs) remaining in the PCR reaction system, and does not require denaturation at all. This method eliminates the problem of quick renaturation of PCR reaction products [WO96/14434]. This method is a direct transcriptional sequencing method utilizing an RNA polymerase such as T7 RNA polymerase and a terminator for RNA transcription reaction (for example, 3'-deoxyribonucleoside 5'-triphosphates, 3'-dNTPs). According to this method, nucleotide sequences of DNA products amplified by the polymerase chain reaction can be used as they are for sequencing without removing primers and 2'-deoxyribonucleoside 5'-triphosphates (2'-dNTPs). In addition, because it does not require denaturation itself at all, it can avoid the problem of quick renaturation of PCR products, and hence is an extremely excellent method.

However, the present inventors further studied the above method, and found that it has a problem to be solved in order to obtain more accurate nucleotide sequence data.

In the above nucleotide sequence determination method, an RNA polymerase such as T7 RNA polymerase is used for the reaction in a mixture comprising ribonucleoside 5'-triphosphates including ATP, GTP, CTP, UTP and derivatives thereof, and at least one 3'-deoxyribonucleotide such as 3'-dATP, 3'-dGTP, 3'-dCTP, 3'-dUTP and derivatives thereof. In this reaction, polyribonucleotides are synthesized by sequential incorporation of ribonucleotides and deoxyribonucleotides into a ribonucleotide sequence in a manner corresponding to the sequence of templates.

However, it was found that 3'-deoxyribonucleotides and derivatives thereof are unlikely to be incorporated into the sequence rather than corresponding ribonucleotides, and the occurrence of the incorporation may also vary among the ribonucleotides and the 3'-deoxyribonucleotides depending on a base group each nucleotide has. Such biased incorporation between ribonucleotides and 3'-deoxyribonucleotides, as well as among ribonucleotides having different base groups and among deoxyribonucleotides having different base groups may result in short transcription products and fluctuation of signals from labeled ribonucleotides. Therefore, it is difficult to obtain accurate sequence data even though transcription products can be obtained.

Therefore, an object of the present invention is to provide an RNA polymerase exhibiting incorporation ability with no or little bias resulting from differences in nucleotides.

In the description of the present invention, amino acid residues are represented by the conventionally used one-letter codes. For clarification, they are specifically mentioned for only those amino acids appearing in this text as follows: phenylalanine (F), tyrosine (Y), proline (P), leucine (L), and histidine (H). A numeral accompanied by the codes is a number counted from the N-terminus of the polymerase. For example, "F667" means that the 667th amino acid residue of this polymerase is F, and "F667Y" means that Y was substituted for F of the 667th residue.

By the way, DNA polymerases are also known to show biased incorporation resulting from difference in a base group each nucleotide has, and mutant DNA polymerases free from such biased incorporation is also known [Japanese Patent Unexamined Publication (KOKAI) No. (Hei) 8–205874/1996; and Tabor et al., Proc. Natl. Acad. Sci. USA, 92:6339–6343, (1995)].

In the aforementioned literature, it is described as follows. In the sequencing reaction utilizing T7 DNA polymerase, the 526th amino acid in the polymerase contributes to equalize nucleotide incorporation. And due to homology between T7 DNA polymerase and other DNA polymerases, the bias of incorporation of the other DNA polymerases may be reduced by replacing an amino acid residue present in their region homologous to the 526th amino acid including region in the T7 DNA polymerase. That is, Y (tyrosine) 526 of T7 DNA polymerase results in the reduced bias of efficiency for incorporation of 2'-dNTPs and 2',3'-ddNTPs. F (phenylalanine) 762 of E. coli DNA polymerase I and F (phenylalanine) 667 of Thermus aquaticus DNA polymerase (generally called Taq DNA polymerase) are the amino acid residues corresponding to Y526 of T7 DNA polymerase and the bias of these polymerases may be reduced by substituting F762Y (tyrosine) and F667Y (tyrosine) respectively for these residues.

Further, it is also described that it was suggested that modification of a region of T7 RNA polymerase corresponding to the region discussed for DNA polymerases, i.e., the residues 631–640, may change its specificity for dNTPs.

However, RNA polymerases have not been used for sequencing methods so far, and therefore the different efficiency of ribonucleotide incorporation itself has not become a problem. Under such circumstances, any mutant RNA polymerases free from the biased incorporation have of course not been known. In fact, the aforementioned Japanese Patent Unexamined Publication (KOKAI) No. (Hei) 8-205874/1996 does not mention any specific examples of modification of T7 RNA polymerase.

The region of T7 RNA polymerase mentioned above is considered to correspond to the region consisting of 9–10 amino acid residues between amino acids K and YG in the motif B mentioned in Protein Engineering, 3:461–467, 1990, which region is particularly conserved in DNA polymerase α and I, and DNA-dependent RNA polymerases (T7 RNA polymerase is classified in these polymerases). F (phenylalanine) of the amino acid residue 762 in E. coli DNA polymerase and the amino acid residue 667 in Taq DNA polymerase, previously discussed for DNA polymerases, are observed in many of DNA polymerases classified in the type I. However, it was surprisingly found that T7 RNA polymerase does not have F (phenylalanine) in the residues 631–640 corresponding to the aforementioned region, though T7 RNA polymerase is highly homologous to DNA polymerases. Therefore, the teachings of the aforementioned literatures could not be realized as described.

Further, the present inventors attempted modification of amino acids of T7 RNA polymerase in the region corresponding to the helix O of the finger subdomain of E. coli DNA polymerase 1, in which F762 of E. coli DNA polymerase I presents. However, F (phenylalanine) was not found also in the helix Z in T7 RNA polymerase, which is indicated in the steric structure reported in the literature of Sousa et al. (Nature, 364:593–599, 1993) and corresponds to the helix O of E. coli DNA polymerase I.

Under the circumstances, the present inventors originally searched for a novel RNA polymerase in order to provide an RNA polymerase which exhibits little or no bias for the incorporating ability valuable due to the kind of ribonucleotides and 3'-deoxyribonucleotides. As a result, the present invention was completed based on the findings that an RNA polymerase having an increased ability of incorporating 3'-deoxyribonucleotides and derivatives thereof can be obtained by partially modifying amino acids in a wild type RNA polymerase.

While it will be apparent from the descriptions hereinafter, the RNA polymerase of the present invention, or in particular the location of the amino acid modification thereof is not suggested nor taught at all in Japanese Patent Unexamined Publication (KOKAI) No. (Hei) 8-205874/1996, and it was absolutely originally found by the present inventors.

SUMMARY OF THE INVENTION

The present invention relates to an RNA polymerase consisting of a wild type RNA polymerase provided that at least one of the amino acids in the wild type RNA polymerase was modified so as to enhance its ability for incorporating 3'-deoxyribonucleotides and derivatives thereof in comparison with the corresponding wild type RNA polymerase.

BRIEF DESCRIPTION OF THE DRAWINGS

FIG. 1 shows T7 RNA polymerase gene on the T7 phage genome and the amino acid sequence of the encoded T7 RNA polymerase (first half). The nucleotide sequence (SEQ ID NO:1) is shown in the upper sections, and the corresponding amino acid sequence (SEQ ID NO:2) is in the lower sections. The numerals for the nucleotide sequence at the right end indicate numbers of T7 phage genome registered at the DNA sequence database GeneBank (Locus T7CG, 39,937 base pairs), and the numerals of amino acids are appended from the first M (methionine) of T7 RNA polymerase starting with 1, and indicate that the full length is composed of 883 amino acid residues.

FIG. 2 shows T7 RNA polymerase gene on the T7 phage genome and the amino acid sequence of the encoded T7 RNA polymerase (latter half). The nucleotide sequence (SEQ ID NO:1) is shown in the upper sections, and the corresponding amino acid sequence (SEQ ID NO:2) is in the lower sections. The numerals for the nucleotide sequence at the right end indicate numbers of T7 phage genome registered at the DNA sequence database GeneBank (Locus T7CG, 39,937 base pairs), and the numerals of amino acids are appended from the first M (methionine) of T7 RNA polymerase starting with 1, and indicate that the full length is composed of 883 amino acid residues.

FIG. 3 (SEQ ID NOs:3–6) shows alignment of amino acid sequences of the currently reported phage-derived RNA polymerases (first half). The T7 RNA polymerase at the top is used as a standard, and the symbols•(dot) indicate the same amino acid residues as the T7 RNA polymerase,— indicates absence, and * at the bottom indicates an amino acid residue common to all of the polymerases.

FIG. 4 (SEQ ID NOs:3–6) shows alignment of amino acid sequences of the currently reported phage-derived RNA polymerases (latter half). The T7 RNA polymerase at the top is used as a standard, and the symbols•(dot) indicate the same amino acid residues as the T7 RNA polymerase,— indicates absence, and * at the bottom indicates an amino acid residue common to all of the polymerases.

FIG. 6 (SEQ ID NOs:3–4) shows alignment of amino acid sequences of T7 RNA polymerase and T3 RNA polymerase (first half). The T7 RNA polymerase at the top is used as a standard, and the symbols * (dot) indicate the same amino acid residues as the T7 RNA polymerase,—indicates absence, and * at the bottom indicates amino acid residues common to the both polymerases.

FIG. 7 (SEQ ID NOs:34) shows alignment of amino acid sequences of T7 RNA polymerase and T3 RNA polymerase (latter half). The T7 RNA polymerase at the top is used as a standard, and the symbols (dot) indicate the same amino acid residues as the T7 RNA polymerase,—indicates absence, and * at the bottom indicates amino acid residues common to the both polymerases.

FIG. 8 shows the sequences (SEQ ID NOs:11–13) around the residues 641–667 of T7 RNA polymerase, and amino acid sequences of the corresponding regions of T3 RNA polymerase (SEQ ID NOs:14), K11 RNA polymerase (SEQ ID NO:15) and SP6 RNA polymerase (SEQ ID NO:16). While all of the residues are shown for T7RNA polymerase, the corresponding residues are indicated with•(dot) for T3, K11, and SP6 when they are the same as those of T7.

EMBODIMENTS FOR CARRYING OUT THE INVENTION

Figure 5:
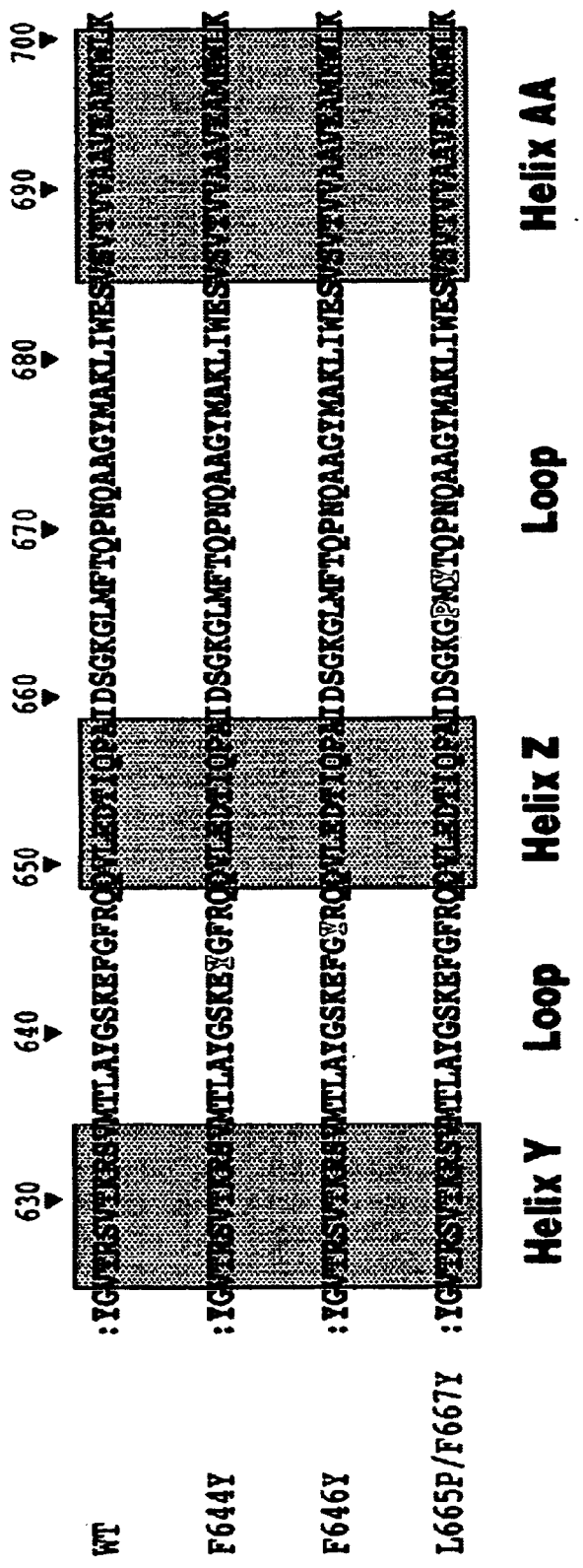
FIG. 5 (SEQ ID NOs:7–10) shows details of mutated sites of T7 RNA polymerase. The outline characters indicate mutated amino acids.

According to the present invention, the "wild type RNA polymerase" includes any naturally occurring RNA polymerases. In addition, the "wild type RNA polymerase" may be a wild type RNA polymerase having substitution, insertion and/or deletion of amino acids which are not the modification for obtaining increased ability for incorporating 3'-deoxyribonucleotide and derivatives thereof in comparison with the corresponding wild type RNA polymerase. That is, wild type RNA polymerases artificially modified with a purpose other than that described above are included in the above "wild type RNA polymerase". However, it is suitable to make such substitution, insertion and/or deletion of amino acids to the extent that the activity of RNA polymerase is maintained.

Examples of the "wild type RNA polymerase" include RNA polymerases derived from T7 phage, T3 phage, SP6 phage, K11 phage and the like. However, it is not limited to these RNA polymerases.

The "wild type RNA polymerase" according to the present invention include naturally occurring thermostable RNA polymerase in order to impart thermostability. However, it is suitable to make the modification for imparting thermostability to the extent that the activity of RNA polymerase is maintained. The mutant RNA polymerase of the present invention prepared by using a thermostable RNA polymerase at the "wild type RNA polymerase" shall be thermostable. As a result, for example, it can be used in PCR to synthesize RNA fragments for sequencing in situ, i.e., during PCR, by using the PCR product as a template.

T7 RNA polymerase is known to be a promoter specific RNA polymerase with an extremely high specificity. The nucleotide sequence and production method of T7 RNA polymerase are reported in Davanloo et al., Proc. Natl. Acad. Sci. USA, 81:2035–2039 (1984). Its large scale production has been already described in Zawadzki et al., Nucl. Acids Res., 19:1948 (1991). This phage-derived RNA polymerase can pursue the transcription reaction with a single polypeptide, unlike RNA polymerases of *E. coli* and higher organisms. (Chamberlin et al., Nature, 228:227–231,1970). Therefore, it is a particularly excellent material for analyzing the mechanism of transcription, and many mutants have been isolated and reported. Further, the results of its crystallographic analysis are mentioned in Sousa et al., Nature, 364:593–599, 1993.

As other promoter specific RNA polymerases of high specificity, 3 kinds of RNA polymerases derived from T3 phage which infects *E. coli*, SP6 phage which infects *Salmonella*, and K11 phage which infects *Klebsiella pneumoniae* have been well known.

The 4 kinds of RNA polymerases mentioned above quite resemble to one another in their primary structure of amino acids, sequence of promoter and the like as described hereinafter.

The RNA polymerase of the present invention has an increased ability of incorporating 3'-deoxyribonucleotides and derivatives thereof in comparison with the ability of a corresponding wild type RNA polymerase. As described above, wild type RNA polymerases poorly incorporate 3'-deoxyribonucleotides in comparison with ribonucleotides, which has obstructed their use in nucleotide sequencing. In contrast, the RNA polymerase of the present invention is modified so as to have the ability of incorporating 3'-deoxyribonucleotides and derivatives thereof at least twice higher than that of the wild type. The incorporation of 3'-deoxyribonucleotides tends to be decreased especially when 3'-deoxyribonucleotide derivatives are labeled with a fluorescent tag. The RNA polymerase of the present invention can also improve incorporation of such 3'-deoxyribonucleotide derivatives.

The term ribonucleotide herein used means ribonucleoside 5'-triphosphates including ATP, GTP, CTP, UTP and derivatives thereof, and 3'-deoxyribonucleotide means 3'-dATP, 3'-dGTP, 3'-dCTP and 3'-dUTP, and the derivatives thereof means, for example, compounds composed of these 3'-deoxyribonucleotides which have a fluorescent label.

The RNA polymerase of the present invention is that at least one of the amino acids in a corresponding wild type RNA polymerase is modified. This will be explained in detail hereinafter.

On the basis of the aforementioned various reports about T7 RNA polymerase, the present inventors tried to construct a mutant RNA polymerase which has little or no bias for incorporation efficiency valuable depending on the kind of ribonucleotides observed for T7 RNA polymerase. Various mutants were actually prepared to determine, in particular, which amino acids on wild type RNA polymerases should be mutated, and what kind of amino acids should be used for substitution when substitution is used as mutation. Then, it was found that the ability of incorporating 3'-deoxyribonucleotides and derivatives thereof can be improved by modifying at least one amino acid of wild type RNA polymerases, and completed the mutant RNA polymerase of the present invention.

The present inventors first constructed an expression plasmid pT7R inserted with the T7 RNA polymerase gene, and then mutants of T7 RNA polymerase were constructed based on the expression plasmid pT7R. That is, mutant T7 RNA polymerases, F644Y, F646Y, F667Y, F733Y, F782Y, and F882Y were constructed in which F (phenylalanine) residue of T7 RNA polymerase was replaced with Y (tyrosine) residue, and the ability of incorporation of these mutants was compared. Properties of Y639F mutant of the T7 RNA polymerase, which is a mutant at a location corresponding to Y526 of T7 DNA polymerase, are described in the literature (Sousa., EMBO J., 14:4609–4621 (1995)). Y639F mutant was also constructed, which has a mutation within the residue 631–640, those suggested to change their specificity for dNTP in Japanese Patent Unexamined Publication (KOKAI) No. (Hei) 8-205874/1996.

Figure 2:
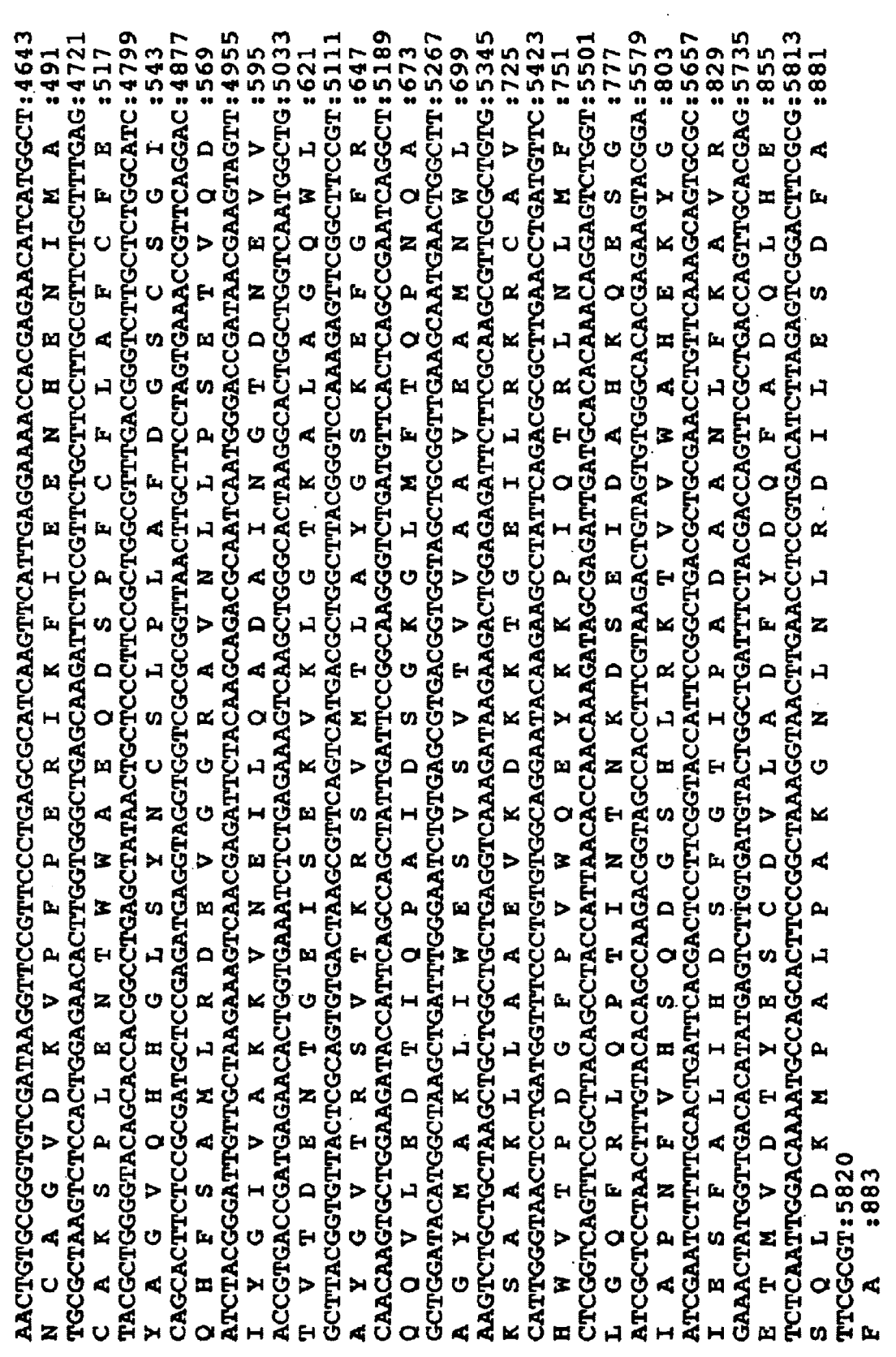

The amino acid sequence of wild type T7 RNA polymerase mentioned in this specification is based on the sequence encoded by nucleotides 3171–5822 of the T7 phage RNA sequence from the gene sequence database GeneBank, accession No. V01148 J02518 X00411 (39,937 base pairs) (cf. FIGS. 1 and 2). The upper sequences represented in FIGS. 1 and 2 are nucleotide sequences, and the lower sequences are amino acid sequences corresponding to the nucleotide sequences. For the nucleotide sequences, the numerals at the right ends are numbers of T7 phage genome registered at GeneBank (Locus T7CG, 39,937 base pairs), and the numerals at the right ends for the amino acids are appended from the first M (methionine) of T7 RNA polymerase starting with 1 and indicate that the full length consists of 883 amino acid residues.

This amino acid sequence is identical to the amino acid sequence reported in Moffatt et al., J. Mol. Biol., 173(2) :265–269, 1984 mentioned above.

Accordingly, the amino acid sequence and the numerals appended to each of the amino acids of wild type T7 RNA polymerase gene in this specification are basically the sequence and numbers represented in FIGS. 1 and 2. However, as described above, the aforementioned wild type T7 RNA polymerase may contain a substitution, insertion and/or deletion which is not the modification intended by the present invention. Therefore, in the case that the wild type RNA polymerase, to which mutation should be introduced for the purpose of the present invention, is a wild type T7 RNA polymerase with other mutation, especially that such mutation is insertion or deletion of amino acids, numbers appended to amino acids are changed due to such insertion and deletion. A wild type T7 RNA polymerase having such insertion and deletion is a member of the wild type T7 RNA polymerase, to which a mutation intended by the present invention should be introduced, so long as it maintains T7 RNA polymerase activity even though its amino acid numbers are different from the numbers represented in FIGS. 1 and 2.

The amino acid numbers in sequences of RNA polymerases other than T7 RNA polymerase are decided as shown in the sequences listed in FIGS. 3 and 4. Those may also have substitution, insertion and/or deletion other than the modification intended by the present invention. Accordingly, like the amino acid sequence and the numbers appended to T7 RNA polymerase, when they have such a mutation by insertion or deletion of amino acids, the amino acid numbers are changed due to such insertion and deletion, and a wild type T7 RNA polymerase having such insertion and deletion is a member of the wild type T7 RNA polymerase to which a mutation intended by the present invention should be introduced.

The T7 RNA polymerase gene is prepared as follows: T7 phage DNA is purified. Separately, a primer specific for upstream of N-terminus amino acid region of the T7 RNA polymerase gene (T7Rpol-N: 5'-ATA TTT TAG CCA TGG AGG ATT GAT ATA TGA ACA CGA TTA ACA TCG CTA AG-3' (SEQ ID NO:24)) and a primer specific for downstream of C-terminus amino acid region of the same (T7Rpol-C: 5'-ATA TTT TAG CCA TGG TAT AGT GAG TCG TAT TGA TTT GGC G-3' (SEQ ID NO:25)) are synthesized. The phage DNA is used as a template for PCR, and thus an expression vector pT7R can be constructed (cf. Example 1). This expression vector can be transformed into E. coli DH5α, and the transformed cells express a large amount of T7 RNA polymerase protein when isopropyl-β-Dthiogalactopyranoside (IPTG) is added.

When the sequence of this T7 RNA polymerase gene prepared as described above was compared with the amino acid sequence shown in FIGS. 1 and 2, the both sequences completely confirmed each other. The amino acid sequence shown in FIGS. 1 and 2 and the amino acid sequence reported in Grachev et al., Bioorg. Kim., 10:824–843, 1984 are different in that the 623rd Y and the 665th L in the amino acid sequence represented in FIGS. 1 and 2 are replaced with H (623rd) and P (665th) respectively in the amino acid sequence reported by Grachev et al. As described above, wild type RNA polymerases, which are the basis of the mutant RNA polymerase of the present invention, may contain substitution, insertion, and/or deletion of amino acids with respect to the sequence shown in FIGS. 1 and 2, which is not the modification intended by the present invention, and the amino acid sequence reported by Grachev et al. where the 623rd and the 665th residues are H and P respectively is included in a member of the wild type RNA polymerases to be a basis of the mutant RNA polymerase of the present invention.

The T7 RNA polymerase purified from E. coli harboring the expression vector pT7R exhibited sufficient RNA synthesis activity in vitro in the presence of DNA containing T7 promoter. Based on this expression plasmid pT7R, the above-mentioned Y639F, F644Y, F646Y, F667Y, F733Y, F782Y, and F882Y were constructed as mutant T7 RNA polymerases, and incorporation ability of these mutants was compared.

For the mutant T7 RNA polymerase having F644Y mutation, another mutation for replacing L665, which is adjacent to F664, with P was introduced in addition to the mutation of F644 according to the report of Grachev et al. mentioned above. That is, mutations of F644Y/L665P were introduced to examine the influence of L665P. Also for the mutant T7 RNA polymerase having F667Y mutation, another mutation for replacing L665, which is adjacent to F667, with P was introduced in addition to the mutation of F667 according to the report of Grachev et al. mentioned above. That is, mutations of F665P/F667Y were introduced.

A mutant T7 RNA polymerase which is introduced with F644Y/L665P/F667Y mutations was also constructed. Comparison of incorporation ability of these mutants was also performed.

The T7 RNA polymerases introduced with mutations were purified, and their abilities of promoter sequence specific RNA synthesis and incorporation of ribonucleoside 5'-triphosphates including ATP, GTP, CTP, UTP and derivatives thereof, as well as 3'-dATP, 3'-dGTP, 3'-dCTP, 3'-dUTP and derivatives thereof were compared with those of wild type T7 RNA polymerase. The results are shown in Table 1 hereinafter.

As a result, as shown in Table 1, F644Y, F644Y/L665P, L665P/F667Y and F644Y/L665P/F667Y maintained sufficient RNA synthesis activity, and showed marked improvement of incorporation of 3'-dATP, 3'-dGTP, 3'-dCTP, 3'-dUTP and derivatives thereof. The incorporation ability of the F644Y/L665P mutant was comparable to that of the F644Y mutant. From these results, it can be seen that the substitution of proline for leucine at 665 do not affect on the incorporation of 3'-dATP, 3'-dGTP, 3'-dCTP, 3'-dUTP and derivatives thereof. While the results are shown only for the L665P/F667Y mutant in Table 1, the F667Y mutant also showed the incorporation ability comparable to that of the L665P/F667Y mutant. The incorporation ability of the F644Y/L665P/F667Y mutant was the highest. While not shown in Table 1, the incorporation ability of the F644Y/F667Y mutant was almost equal to that of the F644Y/L665P/F667Y mutant.

The F782Y mutant maintained RNA synthesis activity, and showed slightly improved ability for incorporating 3'-dATP, 3'-dGTP, 3'-dCTP, 3'-dUTP and derivatives thereof. The F733Y mutant showed slightly decreased RNA synthesis activity, but showed slightly improved ability for incorporating 3'-dATP, 3'-dGTP, 3'-dCTP, 3'-dUTP and derivatives thereof. The F646Y mutant maintained RNA synthesis activity, but showed no improvement of ability for incorporating 3'-dATP, 3'-dGTP, 3'-dCTP, 3'-dUTP and derivatives thereof. The F882Y mutant is not mentioned in Table 1, because it showed markedly decreased RNA synthesis activity.

The Y639F mutant of the T7 RNA polymerase, which has the mutation at a location corresponding to Y526 of T7 DNA polymerase, maintained RNA synthesis activity, but showed no improvement of ability for incorporating 3'-dATP, 3'-dGTP, 3'-dCTP, 3'-dUTP and derivatives thereof.

The results mentioned above suggest that the RNA polymerase of the present invention is particularly an RNA polymerase having modification of at least one of amino acids present in the "nucleotide binding site" of the polymerase and that such a modification can enhance the ability for incorporating 3' deoxyribonucleotides and other ribonucleotide analogues in comparison with the ability for corresponding ribonucleotides.

The amino acids present in the above "nucleotide binding site" can be, for example, amino acids in a loop between the helix Y and the helix Z and/or amino acids in a loop between the helix Z and the helix AA of wild type RNA polymerase.

From the steric structure shown in the literature of Sousa et al. (Nature, 364:593–599, 1993), the loop (corresponding to amino acid residues 635 to 647 of T7 RNA polymerase) between the helix Y (corresponding to amino acid residues 625 to 634 of the same) and the helix Z (corresponding to amino acid residues 649 to 658 of the same) and/or the loop (corresponding to amino acid residues 659 to 684 of the same) between the helix Z and the helix AA (corresponding to amino acid residues 685 to 699 of the same), which face the inside of the clefts in the polymerase molecule enclosing template DNA, are considered to constitute a part of the ribonucleotide binding site, which is located quite near the nucleotides. In the present invention, the F residues present at 644, 646 and 667 in a region corresponding to the loops were actually replaced with Y residues (see FIG. 5).

The F residues of 733, 782 and 882 are present in a region other than that corresponding to the loop, and considered to face the inside of the clefts in the polymerase molecule. These F residues were also actually replaced with Y residues.

The present invention further relates to an RNA polymerase which has modification at an amino acid selected from those in a region corresponding to the amino acid residues 641–667 of the RNA polymerase derived from T7 phage. The region corresponding to the amino acid residues 641–667 of the RNA polymerase derived from T7 phage corresponds to the abovementioned "nucleotide binding site".

The above-mentioned four RNA polymerases extremely resemble one another in their primary structures of amino acids, sequence of promoter and the like. In FIGS. 3 and 4, alignment of amino acid sequences of the aforementioned four RNA polymerases derived from the phages is represented. From this alignment, it can be seen that the RNA polymerases derived from T7, T3, and K11 highly resemble one another. In particular, the amino acid sequences of RNA polymerases derived from T7 and T3 phages show extremely high similarity as shown in FIGS. 6 and 7. It is conformable to the fact that both of T7 and T3 phages are those infecting E. coli, and they are also resemble each other in their properties. Further, the promoter sequences recognizing these two RNA polymerases also resemble each other, and they have known to have extremely high recognition specificity. Thus, the results obtained in T7 RNA polymerase are relatively readily applied to other RNA polymerases having similar amino acid sequences.

From these high homologies, it can be concluded that a region corresponding to the amino acid residues 644–667 of the RNA polymerase derived from T7 phage in RNA polymerases other than the RNA polymerase derived from T7 phage is the amino acid residues 642–668 for the RNA polymerase derived from T3 phage, the amino acid residues 664–690 for the RNA polymerase derived from K11 phage, and the amino acid residues 633–670 for the RNA polymerase derived from SP6 phage. The RNA polymerases derived from T7, T3, and K11 phages extremely resemble one another as described above, and the results obtained for T7 RNA polymerase can be applied for other RNA polymerases having a similar amino acid sequence (see FIG. 8).

As an example of such other RNA polymerases, RNA polymerase derived from K11 phage having tyrosine at the amino acid residue 644 or 667 can be mentioned. RNA polymerase derived from T3 phage having tyrosine at the amino acid residue 645 or 668 can also be exemplified. RNA polymerase derived from K11 phage having tyrosine at one or more of the amino acid residues 664–669 and 690 can further be exemplified. RNA polymerase derived from SP6 phage having tyrosine at one or more of the amino acid residues 633–638 and 670 can still further be exemplified.

The modification of such an amino acid may be not only a substitution of amino acid but also an insertion or deletion of amino acid. The mutation of amino acid is, for example, substitution of tyrosine for at least one amino acid residue in a naturally occurring amino acid sequence. The amino acid to be replaced may be, for example, phenylalanine. However, the amino acid to be replaced is not limited to phenylalanine, and any amino acid may be replaced so long as it can enhance the ability for incorporating 3'-deoxyribonucleotides and other ribonucleotide analogues relative to ability for the corresponding ribonucleotides.

Among the mutant RNA polymerases of the present invention, the mutant T7 RNA polymerases F644Y, L665P/F667Y and F644Y/L665P/F667Y maintained sufficient RNA synthesis activity, and showed markedly improved ability for incorporating 3'-dNTPs, and the strong bias observed in the wild type is markedly reduced in these polymerases. Use of T7 RNA polymerase F644Y, L665P/F667Y or F644Y/L665P/F667Y having such characteristics enables a nucleotide sequence determination method utilizing transcription products, which is of more excellent practical applicability in comparison with a nucleotide sequence determination method utilizing a DNA polymerase.

E. coli strains pT7RF644Y (DH5α) and pT7RL665P/F667Y (DH5α), which produce the mutant T7 RNA polymerases F644Y and L665P/F667Y respectively, were already deposited at the National Institute of Bioscience and Human-Technology with international deposition numbers of 5998 (FERM-BP-5998) and 5999 (FERM-BP-5999)

respectively on Jul. 2, 1997. *E. coli* strains pT7RF644Y/L665P/F667Y (DH5∝), which produces the mutant T7 RNA polymerase F644Y/L665P/F667Y, was already deposited at the National Institute of Bioscience and Human-Technology with an international deposition number of 6364 (FERM-BP6364) on May 20, 1998.

The present invention includes a method for producing the aforementioned RNA polymerases of the present invention, which comprises preparing a nucleic acid molecule encoding an RNA polymerase, introducing a mutation into the nucleic acid molecule so that one or more nucleotides in one or more regions should be mutated, and collecting a modified RNA polymerase expressed by the mutated nucleic acid molecule. The preparation of the nucleic acid molecule encoding RNA polymerase, introduction of mutation into the nucleic acid molecule, and collection of the modified RNA polymerase can be performed by using conventional methods.

For example, a mutant T7 RNA polymerase can be constructed by the following method. By using an expression vector inserted with a T7 RNA polymerase gene as template, an expression plasmid comprising a region between the Hpa and NcoI restriction sites in the C-terminus side of T7 RNA polymerase gene which is introduced with a mutation by PCR is constructed. Subsequently, this expression plasmid can be transformed into *E. coli* DH5α, which can then produce a large amount of a mutant T7 RNA polymerase protein upon addition of isopropyl-β-D-thiogalactopyranoside (IPTG).

According to the present invention, RNA polymerases can be provided which show little or no bias of the ability for incorporating ribonucleotides and the like, i.e., solve the problems that incorporation of 3'-deoxyribonucleotide and derivatives thereof are difficult in comparison with corresponding ribonucleotides, and that incorporation of ribonucleotides and 3'-deoxyribonucleotides into a sequence is difference between the nucleotides due to a base group accompanied by the nucleotides.

Further, the use of the RNA polymerase of the present invention enables a method for determining nucleotide sequence more excellent than a method for determining nucleotide sequence utilizing a DNA polymerase without complicated operation. In addition, quicker sequencing of DNA can be realized by using an RNA polymerase of the present invention having thermostability in PCR, for example, in the method for determining nucleotide sequence of DNA disclosed in WO96/14434.

EXAMPLES

The present invention will be explained more in detail with reference to the following examples.

Example 1

Cloning of Wild Type T7 RNA Polymerase Gene and Construction of Expression Plasmid T7 phage harbored in *E. coli* was prepared as follows. *E. coli* strain C600 was inoculated in 200 ml of LB culture medium (culture medium prepared by dissolving Bacto tryptone 10 g, Bacto yeast extract 5 g, and NaCl 5 g in 1 liter of water, which was adjusted to pH 7.5, and sterilized in an autoclave). When the cell density reached OD (600 nm)=1.0, the cells were infected with the phage at a multiplicity of infection of about 2. The OD was determined periodically, and when the OD was sharply decreased, the cell residue was removed by centrifugation. The medium was added with NaCl and polyethylene glycol 6000 to final concentrations of 0.5 M and 10% respectively, stirred sufficiently, and left to stand overnight to form precipitates. The precipitates were collected by centrifugation, and suspended in SM buffer (10 mM Tris-HCl, pH 7.5, 10 mM MgSO$_4$, 50 mM NaCl, 0.01% gelatin). This T7 phage concentrate was overlaid on CsCl solution layers carefully overlaid in a centrifugation tube (CsCl solutions having concentrations of 1.267 g/ml, 0.817 g/ml, and 0.705 g/ml from the bottom layer), and centrifuged at 22,000 rpm for 2 hours to form a phage layer. A white band of the phage was carefully separated, and dialyzed against TE buffer (10 mM Tris-HCl, pH 7.5, 1 mM EDTA) to remove the CsCl. This phage solution was treated with phenol to denature phage protein to purify genomic DNA of T7 phage.

Figure 9:
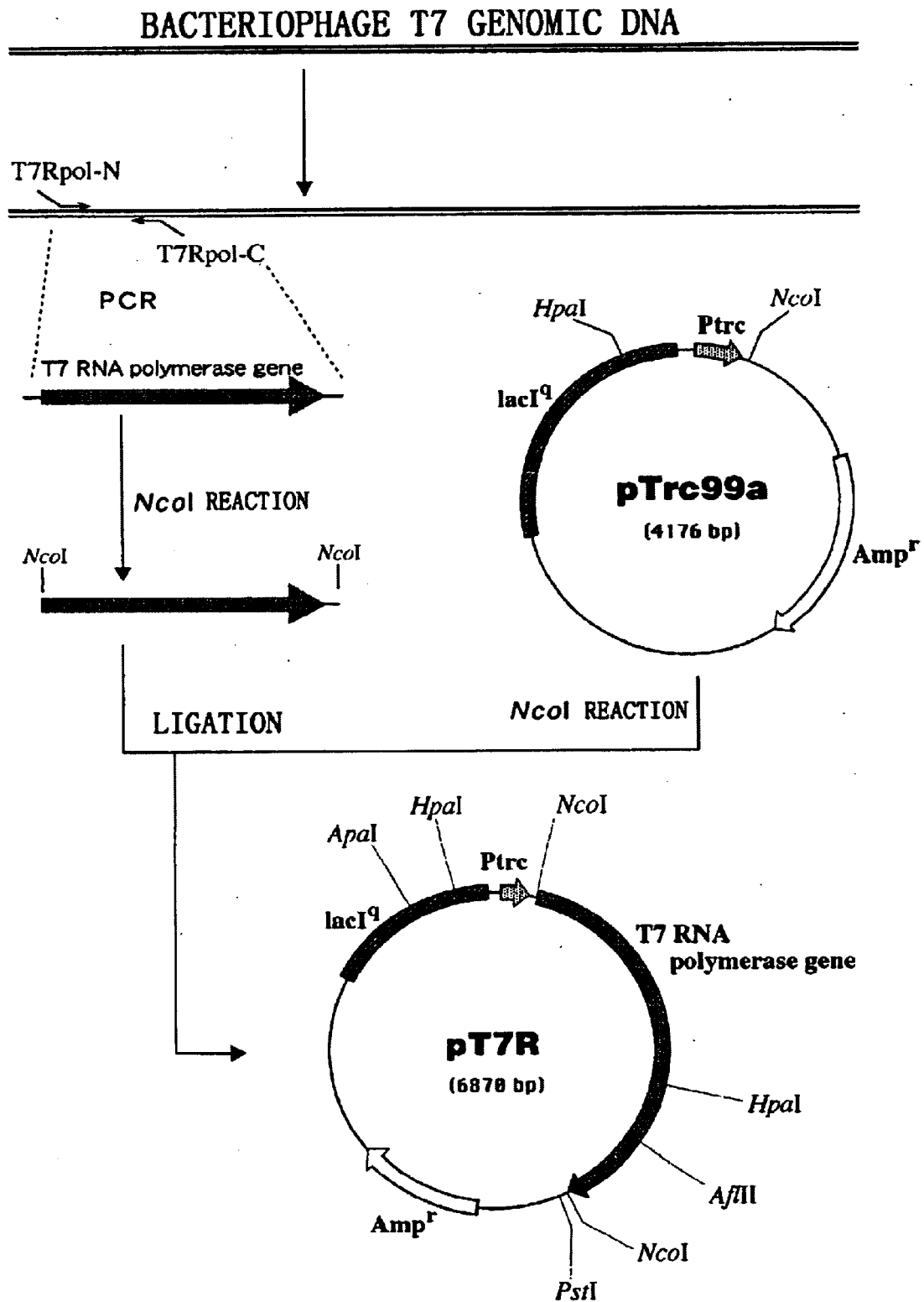
FIG. 9 shows a construction map of pT7R, a plasmid expressing wild type T7 RNA polymerase.

The T7 RNA polymerase gene corresponds to the 3171st–5822nd base pairs in the 39,937 base pairs of the genome DNA [the total nucleotide sequence of T7 genomic gene had already been reported by Dunn et al. (1983, J. Mol. Biol., 166(4):477–535), but it was slightly corrected (see T7 phage DNA sequence of GeneBank, accession No. V01148 J02518X00411)]. This genomic DNA was used for PCR as a template, and cloned into an expression vector as follows (see FIG. 9). That is, the gene encoding the enzyme was amplified by PCR by using a primer specific for upstream of the N-terminus amino acid region of T7 RNA polymerase gene (T7Rpol-N 5'-ATA TTT TAG CCA TGG AGG ATT GAT ATA TGA ACA CGA TTA ACA TCG CTA AG-3') and a primer specific for downstream of the C-terminus amino acid region of T7 RNA polymerase gene (T7Rpol-C 5'-ATA TTT TAG CCA TGG TAT AGT GAG TCG TAT TGA TTT GCG-3'), each containing NcoI restriction site at the 5'-end. This DNA fragment was digested with NcoI, and separated by electrophoresis on 1% agarose gel, and the band of the objective DNA fragment was cut out from the agarose, and purified by using Gene Pure Kit (Nippon Gene). The DNA fragment was ligated to an expression vector pTrc99a (Pharmacia Biotec) which had been digested with NcoI and dephosphorylated to construct pT7R which expressed T7 RNA polymerase at high levels. The plasmid pT7R expressing wild type T7 RNA polymerase was transformed into *E. coli* DH5α, and the cells resistant to antibiotic ampicillin was cultured. The Trc promoter contained in the expression vector pT7R was driven by adding IPTG to the culture medium. Two hours after the addition of IPTG, the *E. coli* cells were collected, and the total protein was analyzed by SDS-polyacrylamide gel electrophoresis. As a result, a protein band was detected at a location corresponding to about 99 kDa, which is the molecular weight of T7 RNA polymerase, only when IPTG was added. This protein was further purified by a partially modified version of the previously described method of Zawadzki, V, et al. 1991, Nucl. Acids Res., 19:1948 (details may be substantially the same as those of the method for purifying mutant T7 RNA polymerase exemplified in Example 3), and found to have RNA polymerase activity which was exerted in a T7 promoter specific manner.

Example 2

Figure 10:
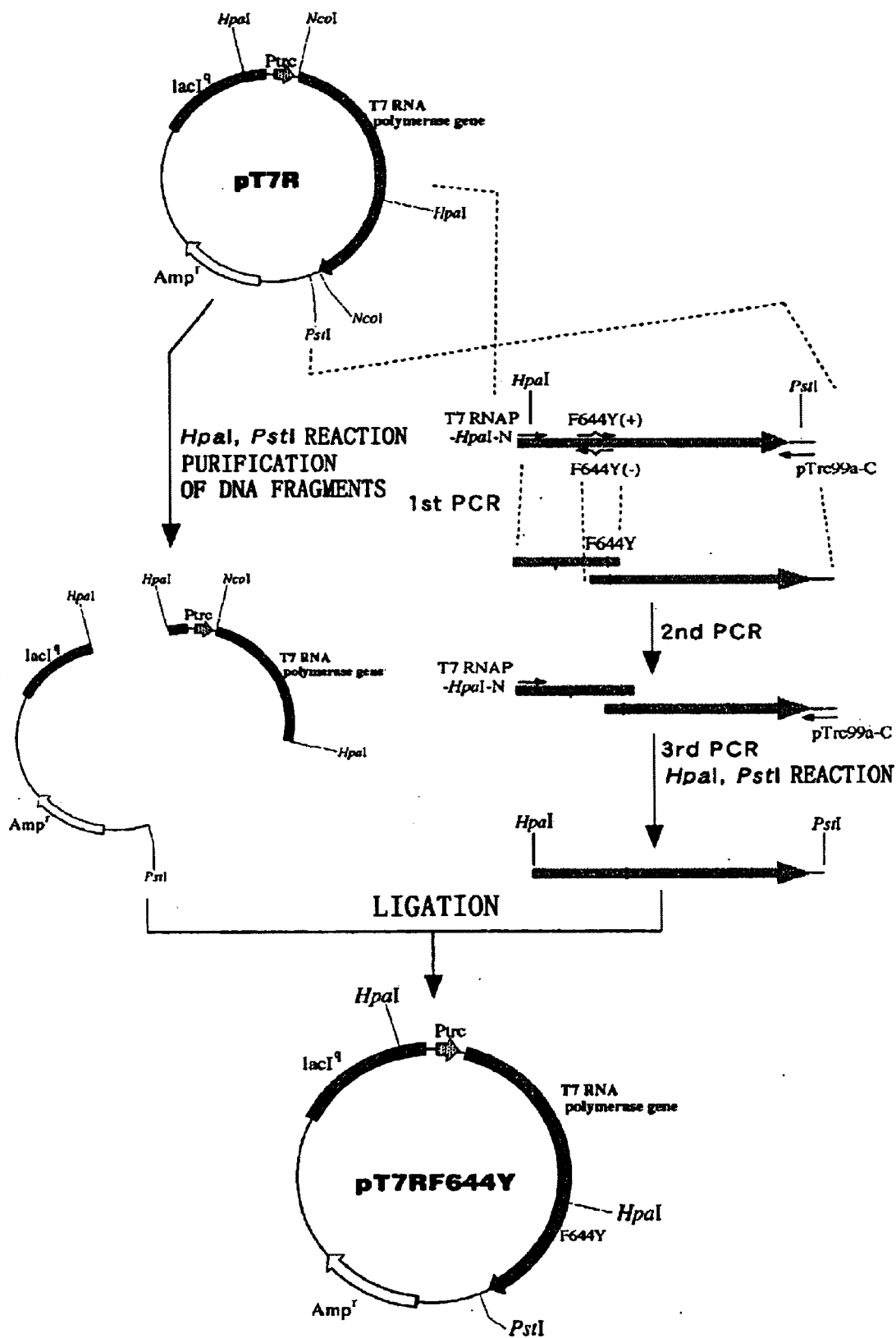
FIG. 10 shows a construction map of pT7RF644Y, a plasmid expressing a mutant T7 RNA polymerase F644Y.

Construction of Expression Plasmid for Producing Mutant T7 RNA Polymerases (1) Construction of Expression Plasmid for Producing Mutant T7 RNA Polymerase F644Y (see FIG. 10)

By using pT7R inserted with the wild type T7 RNA polymerase gene as a template, mutation was introduced by PCR into the region between the HpaI and NcoI restriction sites corresponding to the C-terminus side of the T7 RNA polymerase gene. More precisely, the region was divided into two fragments on the left side and right side of the nucleotide to be mutated, and these DNA fragments were amplified by PCR using primers F646Y(+) (5'-GTT GAC GGA AGC CGT ACT CTT TGG AC-3' (SEQ ID NO:26)) introduced with a mutation and F646Y(−) (5'-GTC CAA AGA GTA CGG CTT CCG TCA AC-3' (SEQ ID NO:27)), and primers T7RNAP-HpaI-N (5'-CGC GCG GTT AAC TTG CTT CCT AG-3' (SEQ ID NO:28)) and pTrc99a-PstI-C (5'-GCA TGC CTG CAG GTC GAC TCT AG-3' (SEQ ID NO:29)), each containing a restriction cleavage site at the 5'-end. These DNA fragments had complementary regions, and denaturation, annealing and extension reactions of the regions were repeated to prepare a DNA fragment introduced with the desired mutation. This DNA fragment was purified by collecting only a DNA fragment of a desired size through agarose gel electrophoresis, and this was re-amplified by using it as a template together with the primers T7RNAP-HpaI-N and pTrc99a-PstI-C, and cleaved with restriction endonuclease HpaI and PstI. This DNA fragment was separated by 1% agarose gel electrophoresis, and the band of the desired DNA fragment was cut out, and purified. The HpaI-PstI DNA fragment of pT7R was replaced with this DNA fragment to introduce a mutation. The resulting pT7R was transformed into *E. coli* DH5α, and cells harboring the plasmid introduced with the mutation were selected. Finally, the nucleotide sequence was determined to confirm whether the mutation was introduced into the desired site. Thus, the expression plasmid pT7RF644Y for producing mutant T7 RNA polymerase F644Y was obtained. For the production of the mutant T7 RNA polymerase F644Y from this plasmid, expression could be induced by adding IPTG to the cultured *E. coli* cells harboring the plasmid, like the production of wild type T7 RNA polymerase.

Figure 11:
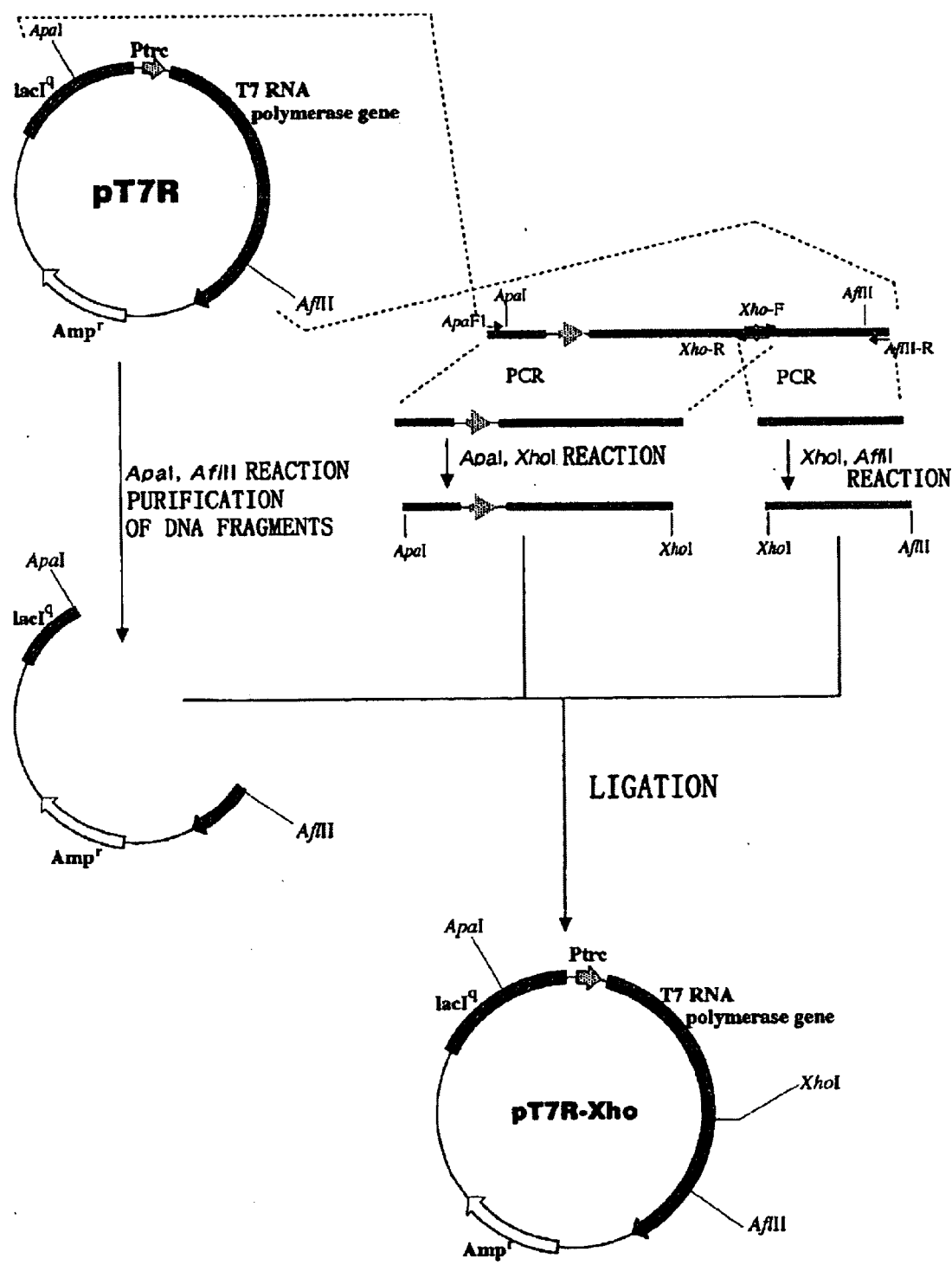
FIG. 11 shows a construction map of an improved version of plasmid pT7R, pT7R-Xho, having a restriction endonuclease XhoI site in the T7 RNA polymerase gene.
Figure 12:
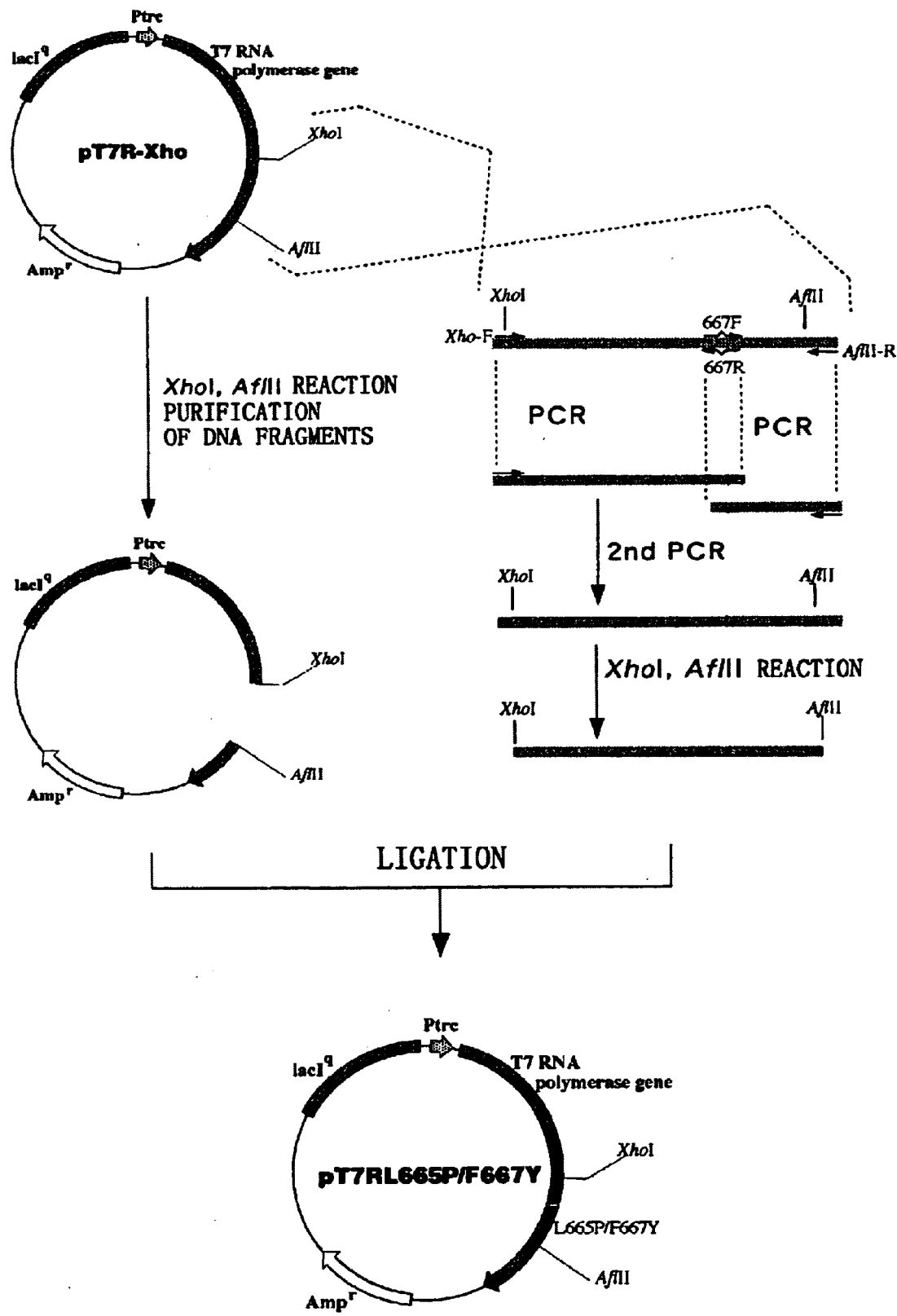
FIG. 12 shows a construction map of pT7RL66SP/F667Y, a plasmid expressing a mutant T7RNA polymerase L665P/F667Y.

(2) Construction of Expression Plasmid for Producing Mutant T7 RNA Polymerase L665P/F677Y (see FIGS. 11 and 12)

The construction of mutant T7 RNA polymerase L665P/F667Y was performed as follows based on PCR technique as in the construction of the F644Y mentioned above.

First, a XhoI restriction site (CTCGAG) was introduced into the T7 RNA polymerase gene region of the expression vector pT7R having the wild type T7 RNA polymerase gene to facilitate the introduction of mutation. More specifically, the expression vector pT7R used as template was amplified by using a primer pair of primer ApaF1 (5'-CAT CTG GTC GCA TTG GGT CAC-3' (SEQ ID NO:30)) and primer Xho-R (5'-CCA AGT GTT CTC GAG TGG AGA-3' (SEQ ID NO:31)), and a primer pair of a primer Xho-F (5'-CTA AGT CTC CAC TCG AGA ACA CTT GG-3' (SEQ ID NO:32)) and a primer AflII-R (5'-CAG CCA GCA GCT TAG CAG CAG-3' (SEQ ID NO:33)), respectively. The former amplified DNA fragment was digested with restriction endonucleases ApaI and XhoI, and the latter amplified DNA fragment with restriction endonucleases AflII and XhoI, and they were ligated to the expression vector pT7R preliminarily treated with ApaI and AflII by using T4 DNA ligase. This reaction product was transformed into *E. coli* DH5α, and several colonies grown on an agar plate containing antibiotic ampicillin were obtained. Some of these colonies were selected and cultured, and plasmid DNA was extracted from the cultured cells to obtain plasmid pT7R-Xho in which a XhoI restriction site was introduced in the T7 RNA polymerase gene region (see FIG. 10). Presence of this XhoI site can be confirmed by cleavage by a treatment with the restriction endonuclease XhoI, and nucleotide sequencing of the DNA. Using this plasmid pT7R-Xho as a template, PCR was performed with a primer pair of primer Xho-R and primer 667R (5'-GCT GAG TGT ACA TCG GAC CCT-3' (SEQ ID NO:34)), and a primer pair of a primer 667F (5'-of-GCT GAG TGT ACA TCG GAC CCT-3' (SEQ ID NO:35)) and a primer AflIIR. The PCR products were directly used as templates for the nucleotide sequencing of the DNA to determine the sequences of the primers 667R and 667F. Then, they were subjected to electrophoresis on 2% agarose gel (Agarose X from Nippon Gene was used as the agarose) respectively, and bands corresponding to DNA fragments of the desired sizes were cut out to purify the DNA fragments by using Gene Pure Kit. The purified two kinds of DNA fragments were mixed, and used as templates for PCR using the primers XhoF and AflIIR. After confirming that the amplified DNA fragment was the desired fragment by restriction mapping and DNA sequencing, the fragment was digested with restriction endonucleases XhoI and AflII, and the resulting fragment was ligated to the plasmid pT7R-Xho preliminarily treated with restriction endonucleases XhoI and AflII by using T4 DNA ligase. This reaction product was transformed into *E. coli* DH5α, and several colonies of the cells grown on an agar plate containing antibiotic ampicillin were obtained. Some of these colonies were selected and cultured, and plasmid DNA was extracted from the cultured cells. The plasmid DNA was confirmed if it was introduced with the desired mutation by DNA sequencing to finally construct an expression plasmid pT7RL665P/F667Y for producing the mutant T7 RNA polymerase L665P/F667Y (see FIG. 12). For the production of the mutant T7 RNA polymerase L665P/F667Y from this plasmid, expression could be induced by adding IPTG to the cultured *E. coli* cells harboring the plasmid, like the production of wild type T7 RNA polymerase.

Example 3

Purification of Mutant T7 RNA Polymerases

Mutant T7 RNA polymerase proteins introduced into *E. coli* were purified.

Wild types of this protein have already been described in Chamberlin, M. et al. Nature, 228:227–231(1970), Davanloo et al., Proc. Natl. Acad. Sci. USA., 81:2035–2039 (1984). Its large scale production has also been reported by Zawadzki, V. et al., Nucl. Acids Res., 19:1948 (1991).

All of the mutant T7 RNA polymerases can be purified by principally the same method. The difference of mutation site may cause some difference in the expression level, and behavior in column chromatography. The purification method of mutant T7 RNA polymerase F644Y is exemplified hereinafter. The expression vector pT7RF644Y for F644Y was introduced into *E. coli* DH5α, and the cells were cultured in a test tube containing LB culture medium containing antibiotic ampicillin. When the OD (600 nm) of the medium reached 0.4–0.6, isopropyl-β-thiogalactopyranoside (IPTG) was added to the culture to a final concentration of 0.4 mM, and the cultivation was further continued for additional 8 hours. Then, the *E. coli* cells were collected by centrifugation. Typically, 2 liters of culture medium affords 10 g of *E. coli* cells in wet weight. If the *E. coli* cells are not used immediately, they can be stored in a refrigerator at −20° C. Subsequent steps for purification of enzyme should be performed at a temperature lower than room temperature, preferably 0–5° C. unless otherwise indicated. The *E. coli* cells were washed with 10 times relative to the cell weight of a washing buffer (20 mM Tris-HCl, pH 8.1, 130 mM NaCl, 2 mM EDTANa$_2$ at 25° C.), centrifuged again [5,000×g, 4° C., 10 minutes), suspended in 10 times in volume of a sonication buffer (50 mM Tris-HCl, pH 8.1, 100 mM NaCl, 0.1 mM EDTANa$_2$, 5 mM dithiothreitol (DTT), 0.1 mM benzamidine, 30 μg/ml phenylmethylsulfonyl fluoride (PMSF), 10 μg/ml bacitracin], and sonicated by using Sonifier 450 (Branson) at 80W for more than 15 minutes to destroy the cells and reduce the viscosity of the cells. Then, the cell suspension is centrifuged at 12,000×g and 4° C. for ten minutes to remove the cell debris. 10% streptomycin sulfate was slowly added dropwise to the resulting supernatant to a final concentration of 2.0% with stirring, and stirring was further continued for 30 minutes. The supernatant was centrifuged at 12,000×g and 4° C. for ten minutes to remove precipitates, and slowly added with ammonium sulfate powder with stirring to form precipitates. In this case, precipitates were first collected by 30% saturation of ammonium sulfate (30% ammonium sulfate precipitation), and the resulting supernatant was further added with ammonium sulfate to 60% saturation with stirring to form precipitates again (30–60% ammonium sulfate precipitation) The supernatant was added again with ammonium sulfate powder to 90% ammonium sulfate saturation, and stirred at 4° C. for 1 hour, and the precipitates were collected by centrifugation. Aliquots of these three ammonium sulfate fractions were analyzed for proteins by SDS-acrylamide gel electrophoresis, and it was found that most of the objective mutant T7 RNA polymerase was present in the 30–60% ammonium sulfate fraction. Therefore, purification was performed hereafter by using this fraction. The 30–60% ammonium sulfate fraction was suspended in a small amount of column buffer (20 mM $KPO_4$, pH 7.7, 100 mM NaCl, 1 mM DTT, 30 μg/ml PMSF), and desalted by dialysis against 500 ml of the same buffer for 16 hours. The dialysate was applied on a heparin-Sepharose column of 5 ml volume (Pharmacia Biotec). Subsequently, the column was washed with the same buffer until any material absorbing ultraviolet ray at 280 nm disappeared, and eluted with a linear gradient of 0.1 M to 0.64 M NaCl in the same buffer of about 40 times volume of the column volume. The eluent was collected in test tubes as fractions of a suitable volume, and immediately subjected to SDS-acrylamide gel electrophoresis for protein analysis to identify fractions containing proteins around a molecular weight considered to be of the objective T7 RNA polymerase. In typical examples, it should be found around 0.4 M NaCl. The fractions containing the protein were collected, and desalted by dialysis against about 1 liter of the column buffer (20 mM $KPO_4$, pH 7.7, 100 mM NaCl, 1 mM DTT, 30 μg/ml PMSF) for 16 hours. The fractions desalted by dialysis were applied to a Q-Sepharose column (Pharmacia Biotec) of 5 ml volume that preliminarily equilibrated with the same buffer, and the column was washed with the same buffer until any material absorbing ultraviolet ray at 280 nm disappeared, and eluted with a linear gradient of 0.1 M to 0.64 M NaCl in the same buffer of about 40 times volume of the column volume. The eluent was collected in test tubes as fractions of a suitable volume, and immediately subjected to SDS-acrylamide gel electrophoresis for protein analysis to identify fractions containing proteins around a molecular weight considered to be of the objective T7 RNA polymerase. In typical examples, it should be found around 0.24 M NaCl. The fractions containing the protein were collected, dialyzed against 500 ml of storage buffer (50% glycerol, 20 mM $KPO_4$, pH 7.7, 100 mM NaCl, 1 mM DTT, 30 μg/ml PMSF) for 16 hours, and stored at −20° C. until use. In vitro RNA synthesis activity and activity of the contaminated ribonuclease of this sample were examined. The in vitro RNA synthesis activity was examined by, for example, performing RNA synthesis reaction according to the enzyme dilution method by using the plasmid containing T7 promoter as a template and a commercially available wild type T7 RNA polymerase (BRL, Gibco) as a standard, and subjecting the synthesized RNA to agarose gel electrophoresis to estimate approximate titer. In this case, because the degree of decomposition of RNA is also determined, simple assay for contaminated ribonuclease can simultaneously be performed. As a typical example, 2,500,000 units of the mutant T7 RNA polymerase F644Y protein was purified from 1 liter of culture medium using the above-described steps, and this preparation was substantially free from RNase contamination.

Example 4

Improvement of Incorporation Ratio of 3'-dNTP Derivatives

3'-DNTP incorporation efficiency of the purified mutant T7 RNA polymerases F644Y and L665P/F667Y was compared with that of wild type T7 RNA polymerase as follows. In vitro transcription reaction was performed by, for example, a partially modified version of the method of Melton, D. A, [Nucleic Acids Res., 12:7035–7056 (1984)]. More specifically, the reaction was performed in a total volume of 10 μl containing a plasmid vector pBluescriptKS (+) having T7 promoter (Stratagene) linearized by the reaction with a restriction endonuclease PvuII or ScaI as a template, 150 μM of 5-carboxy-X-rhodamine-labeled 3'-deoxycytidine-5'-triphosphate which was a dye terminator prepared according to the method described in WO96/14434 as a derivative of 3'-dNTP, 500 μM of GTP and UTP, 250 μM of ATP and CTP, 8 mM Of $MgCl_2$, 2 mM of spermidine-$(HCl)_3$, 5 mM of DTT, 40 mM of Tris/HCl pH 8.0 (BRL, Gibco) and 25 units of wild type T7 RNA polymerase (BRL, Gibco or Nippon Gene) or the mutant T7 RNA polymerase F644Y or L665P/F667Y at 37° C. for 1 hour. Then, to remove the unreacted dye terminator remained in the reaction product, the transcription product was purified by gel filtration using Sephadex G-50 column (Pharmacia Biotec), and the purification product was evaporated to dryness using a centrifugal evaporator.

The above 5-carboxy-X-rhodamine-labeled 3'-deoxycytidine-5'-triphosphate is a compound represented by the following chemical formula:

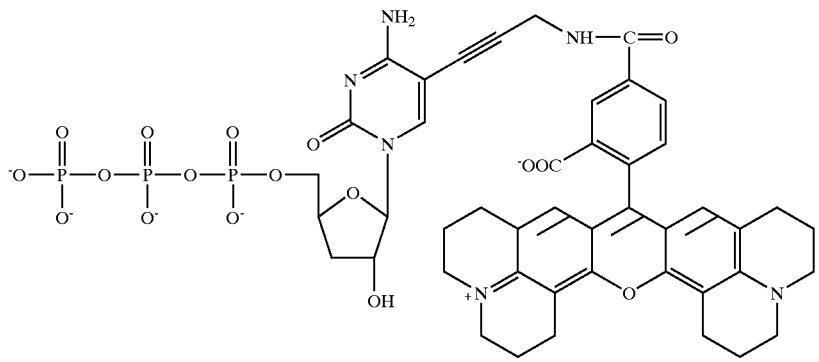

Figure 13:
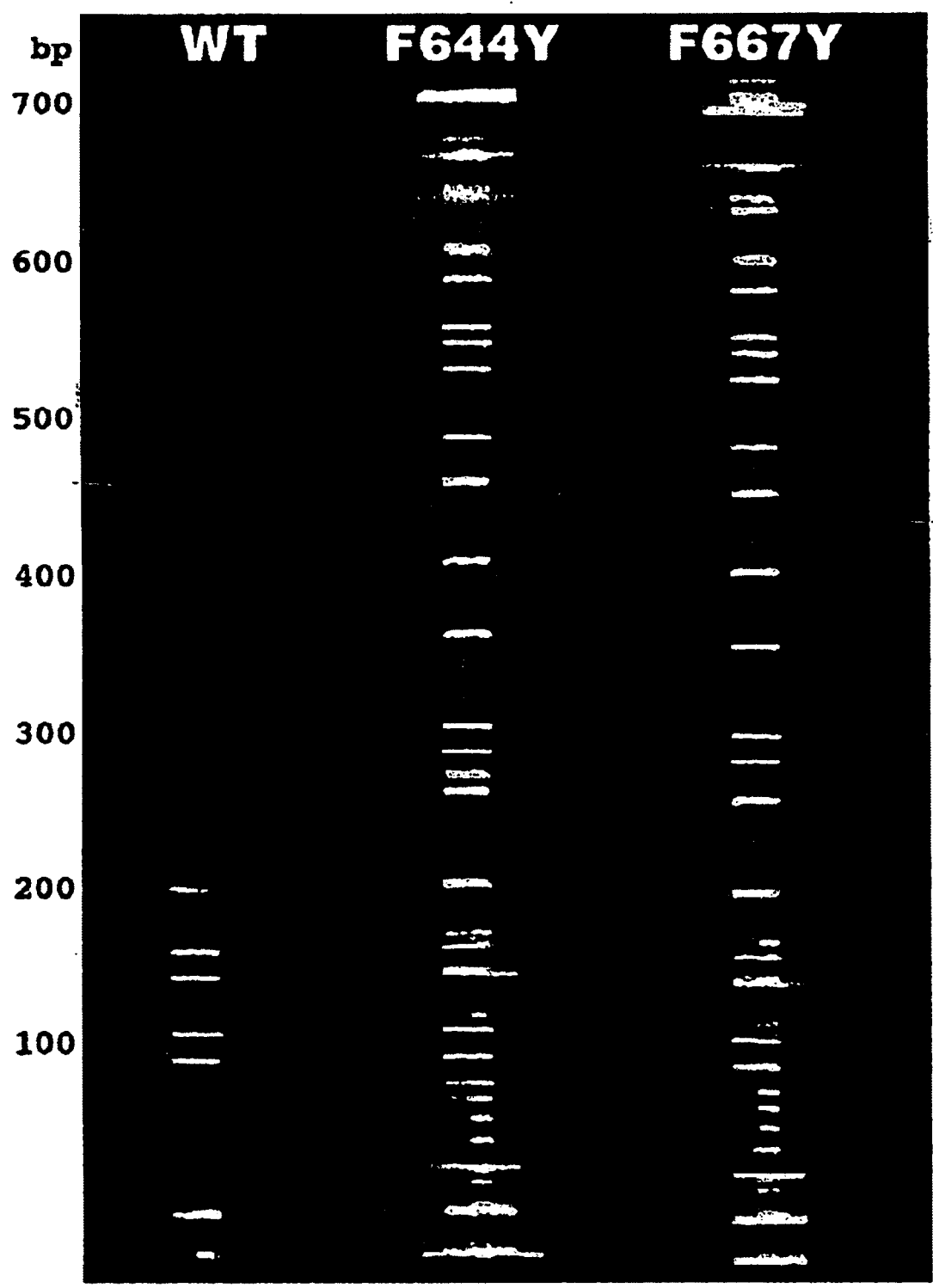
FIG. 13 demonstrates improvement of incorporation rate of dye terminator by mutant T7 RNA polyerases. The results of wild type T7 RNA polymerase (WT), mutant T7 RNA polymerase F644Y (F644Y), and mutant T7 RNA polymerase L665P/F667Y (F667Y) are shown.

The dried reaction product was dissolved in 6 μl of formamide/EDTA/Blue dextran loading buffer according to the instruction manual Ver. 1.0 of ABI PRISM 377 DNA Sequencing System available from Perkin-Elmer Japan, and 2 μl of the solution was analyzed by ABI 377 DNA Sequencer and an analysis program using denatured gel for sequencing analysis which contained 6M urea/4% Long Ranger™ acrylamide solution (FMC). The results are shown in FIG. 13 as a gel image. It was found that the mutant T7 RNA polymerase F644Y could afford a sequence ladder 3 times longer than that afforded by the wild type T7 RNA polymerase, and a transcription product of about 700 bases was also confirmed.

Figure 14:
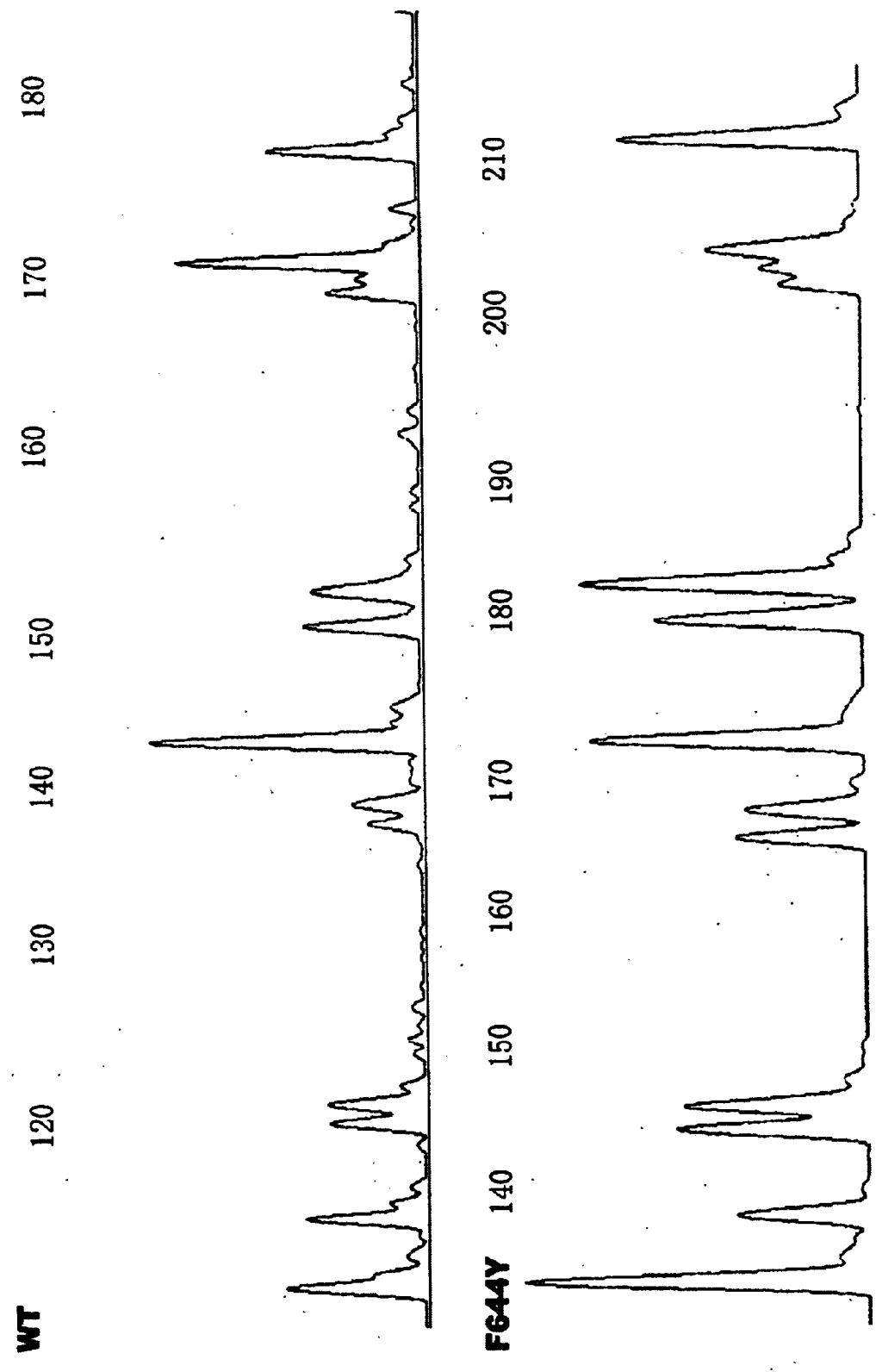
FIG. 14 demonstrates improvement of incorporation rate of dye terminator by mutant T7 RNA polymerase F644Y. The results of wild type T7 RNA polymerase (WT), and mutant T7 RNA polymerase F644Y (F644Y) are indicated as an electropherogram.
Figure 15:
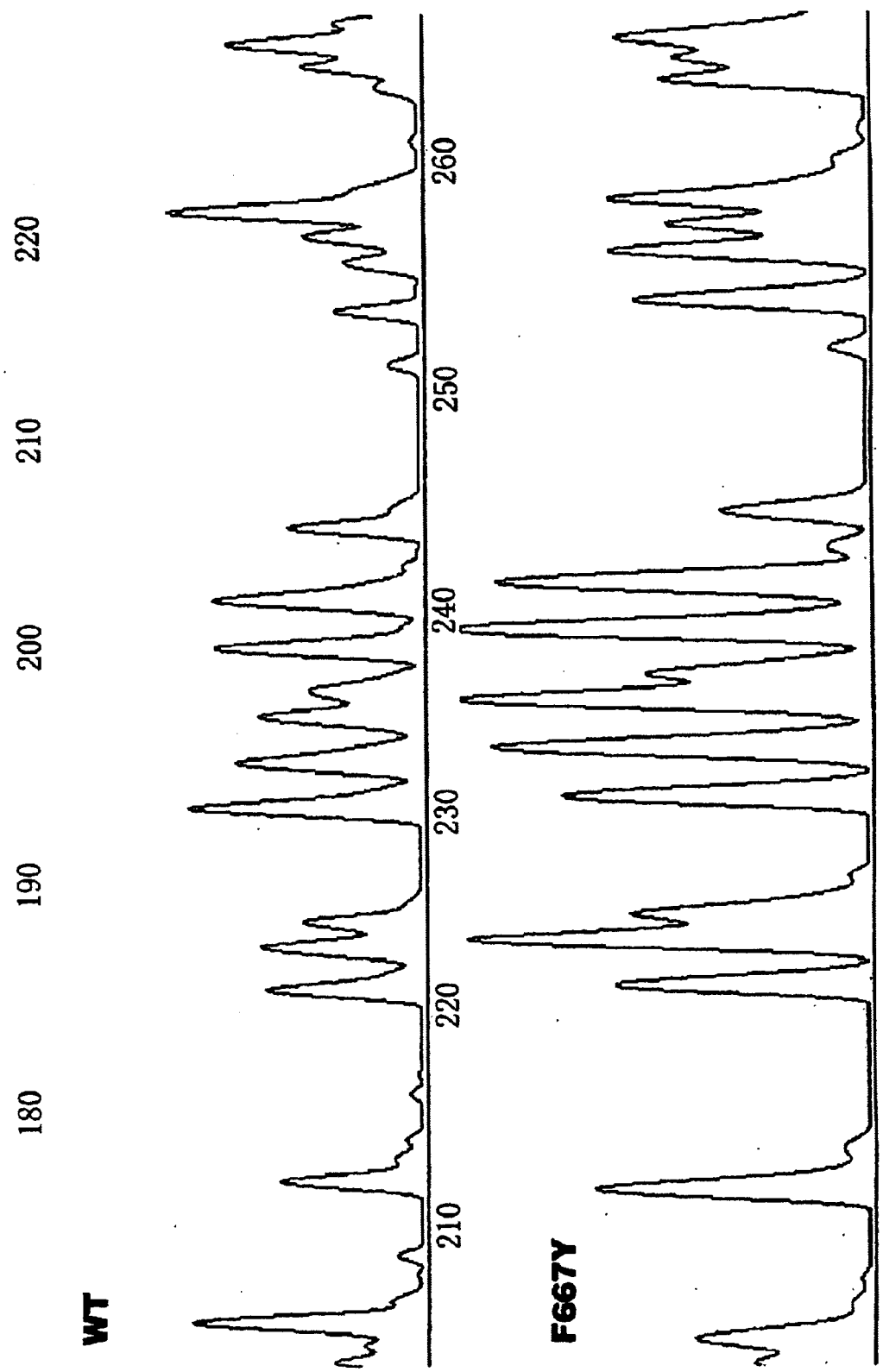
FIG. 15 demonstrates improvement of incorporation rate of dye terminator by mutant T7 RNA polymerase L665P/F667Y. The results of wild type T7 RNA polymerase (WT), and mutant T7 RNA polymerase L665P/F667Y (F667Y) are indicated as an electropherogram.
Figure 16A:
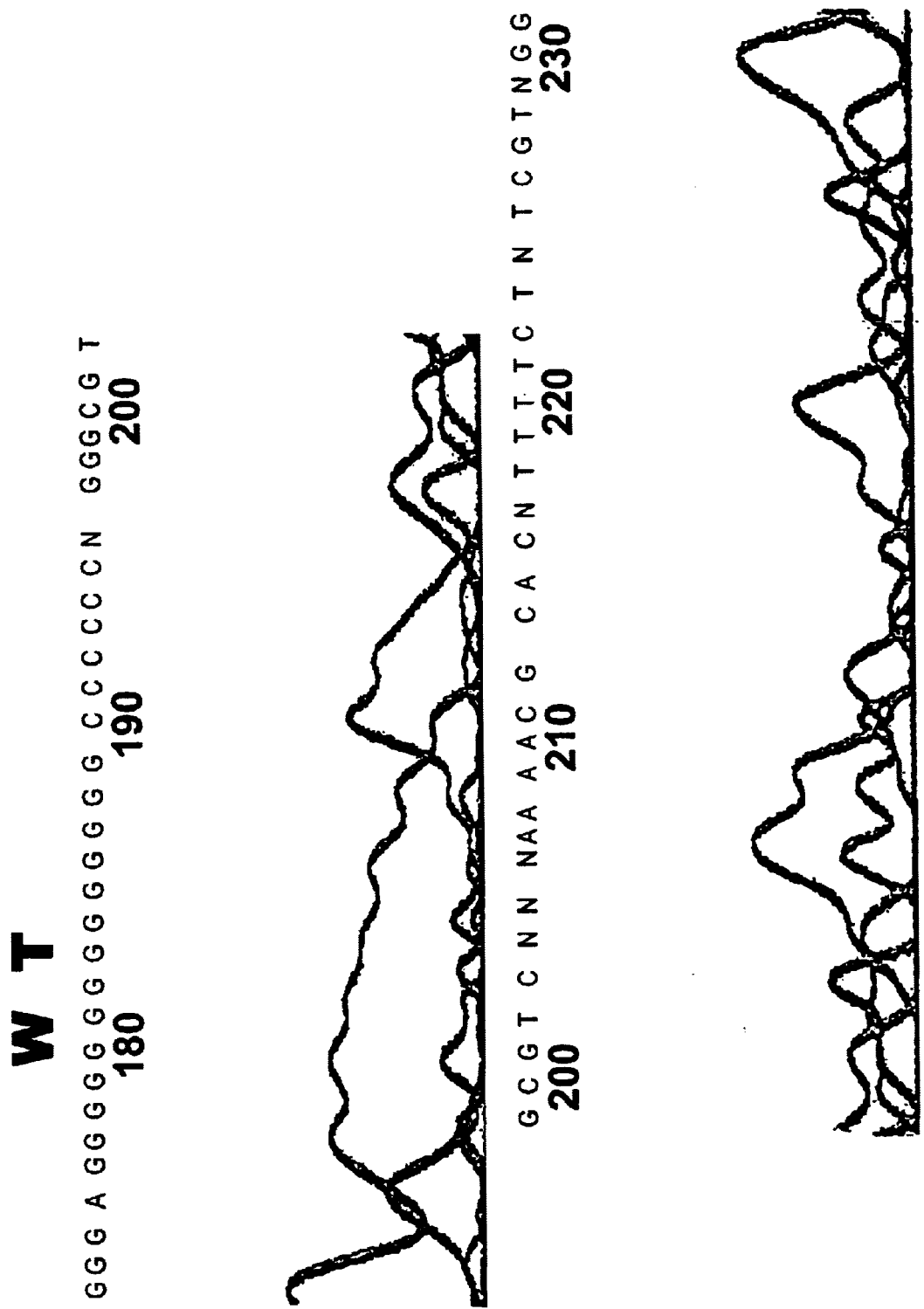
FIGS. 16A–16C show an example of sequencing reaction. The reaction was performed by using wild type T7 RNA polymerase (WT) (SEQ ID NOs:17–18)(FIG. 16A), mutant T7 RNA polymerase F644Y (F644Y) (SEQ ID NOs: 19–20) (FIG. 16B), or a mutant T7 RNA polymerase L665P/F667Y (F667Y) (SEQ ID NOs:21–22)(FIG. 16C). Sequencing patterns of the same area are shown, and it can be observed that the sequencing could not be correctly performed in the wild type T7RNA polymerase (WT) (top), because the base call did not correctly function, and interval of bases became too narrow (representations of the bases overlap).
Figure 16B:
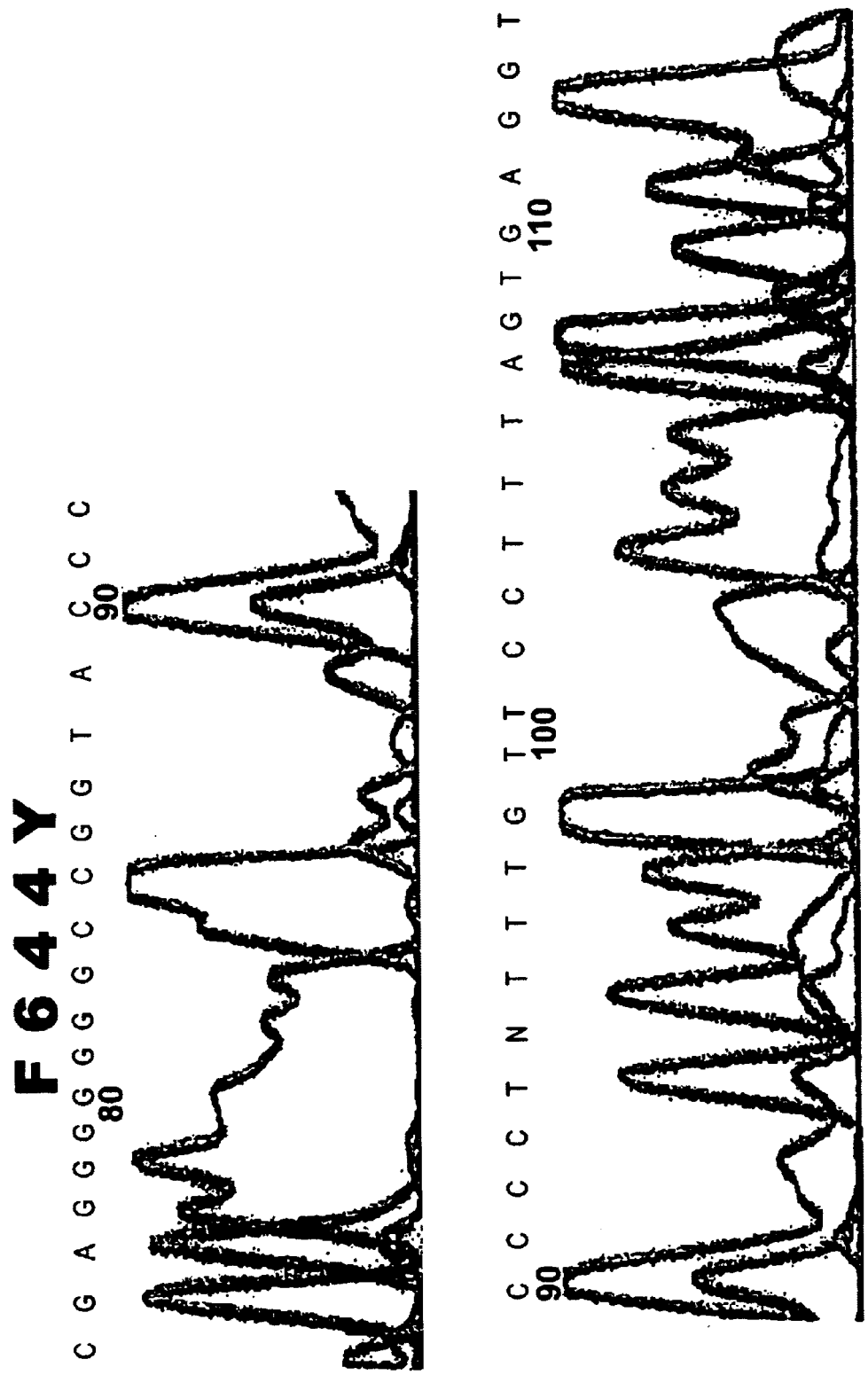
Figure 16C:
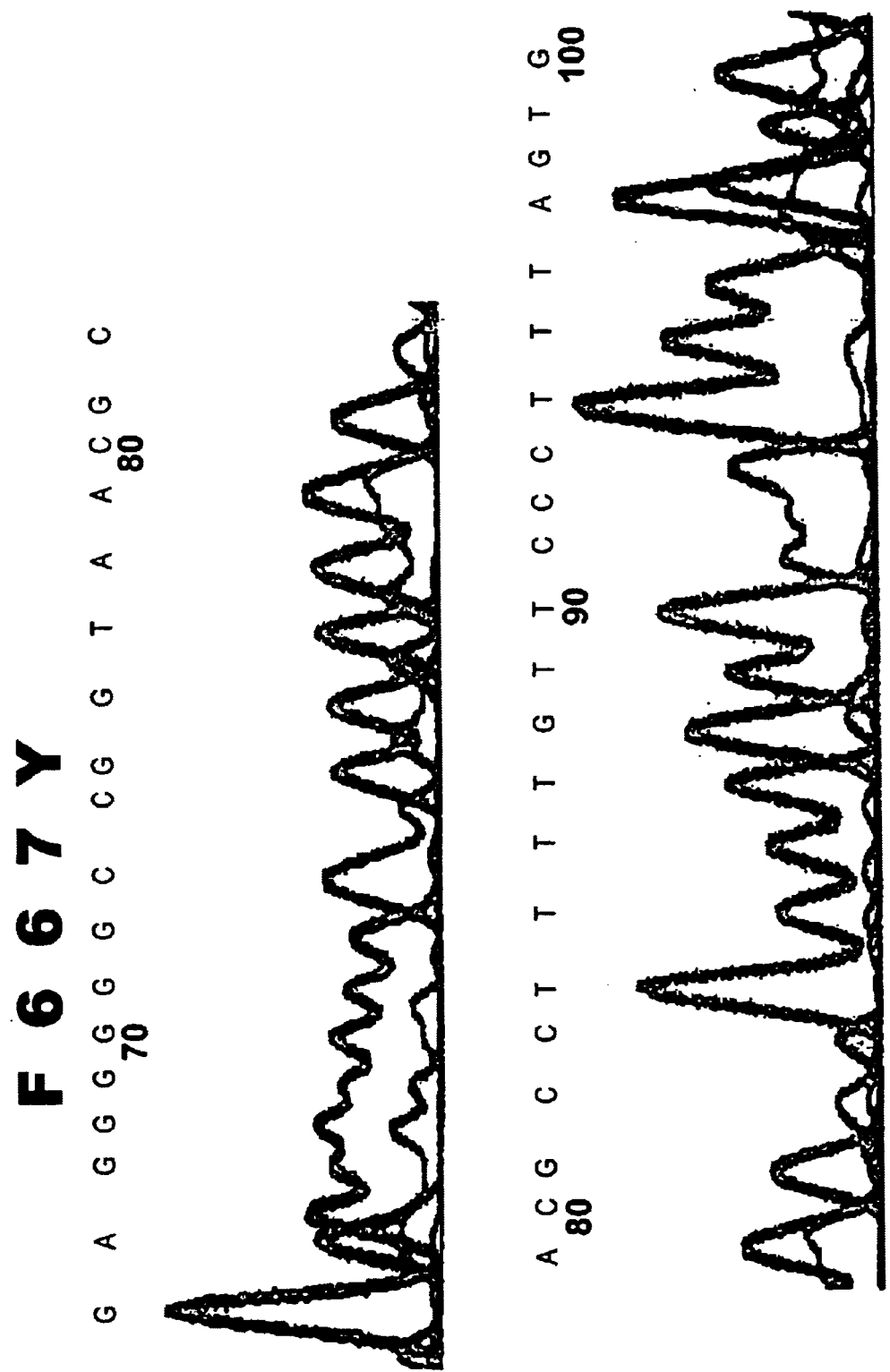

The peak intensities of the sequence ladders obtained by using F644Y and L665P/F667Y are shown in FIG. 14 and FIG. 15 with the peak intensity obtained by using wild type T7 RNA polymerase. From this comparison, it was confirmed that altitude of the peaks for the mutant enzymes showed less fluctuation in comparison with the wild type, and the peak showed stronger signals. This indicates that the mutation of F644Y or L665P/F667Y improved the incorporation efficiency for 3'-dCTP derivatives for this case, and that transcription reaction by these mutant T7 RNA polymerases exhibits ladder extension characteristics comparable to the data productivity of the conventional methods for determining nucleotide sequence using a DNA polymerase.

Example 5

Example of Sequencing Reaction by the Dye Terminator Method Utilizing Mutant T7 RNA Polymerase Sequencing reaction by the dye terminator method was performed utilizing the purified mutant T7 RNA polymerases F644Y and L665P/F667Y, and the wild type T7 RNA polymerase as follows for comparison.

For the in vitro transcription reaction, the method of Melton, D. A. (1984, Nucleic Acids Res., 12:7035–7056) exemplified in Example 4 was used. More specifically, the reaction was performed in a total reaction volume of 10 μl containing a plasmid vector pBluescriptKS (+) having T7 promoter linearized by the reaction with a restriction endonuclease PvuII or ScaI as a template, 5-carboxyrhodamine 6G-labeled 3'-deoxyadenosine-5'-triphosphate, 5-carboxyrhodamine 110-labeled 3'-deoxyguanosine-5'-triphosphate, 5-carboxy-X-rhodamine-labeled 3'-deoxycytidine-5'-triphosphate, and 5-carboxytetramethylrhodamine-labeled 3'-deoxyuridine-5'triphosphate, which were dye terminators prepared according to the method described in WO96/14434 as derivatives of 3'-DNTP, 500 μM of GTP and UTP, 250 μM of ATP and CTP, 8 mM of MgCl$_2$, 2 mM of spermidine-(HCl)$_3$, 5 mM of DTT, 40 mM of Tris/HCl pH 8.0 (BRL, Gibco) and 25 units of wild type T7 RNA polymerase (BRL, Gibco or Nippon Gene) or the mutant T7 RNA polymerase F644Y at 37° C. for 1 hour. Then, to remove the unreacted dye terminators remained in the reaction product, the transcription product was purified by gel filtration using Sephadex G-50 column (Pharmacia Biotec), and the purification product was evaporated to dryness using a centrifugal evaporator.

The above 5-carboxy-X-rhodamine-labeled 3'deoxycytidine-5'-triphosphate is the same compound as used in. Example 4. 5-Carboxyrhodamine 6G-labeled 3'-deoxyadenone-5'-triphosphate, 5-carboxyrhodamine 110-labeled 3'-deoxyguanosine-5'-triphosphate, and 5-carboxytetramethylrhodamine-labeled 3'-deoxyuridine-5'-triphosphate are the compounds represented by the following chemical formulae:

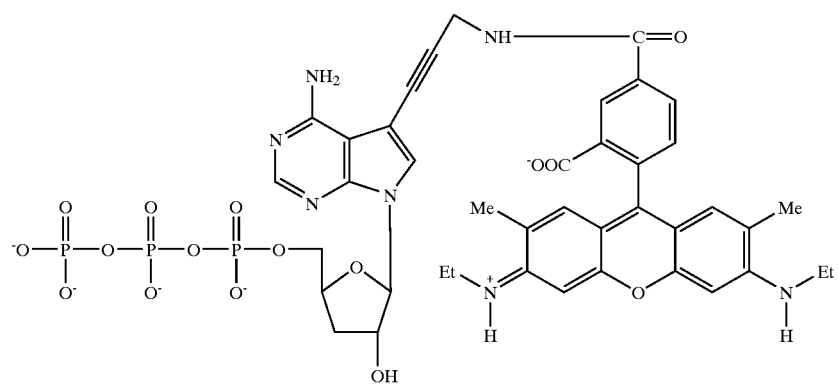

5-Carboxyrhodamine 6G-labeled 3'-deoxyadenone-5'-triphosphate

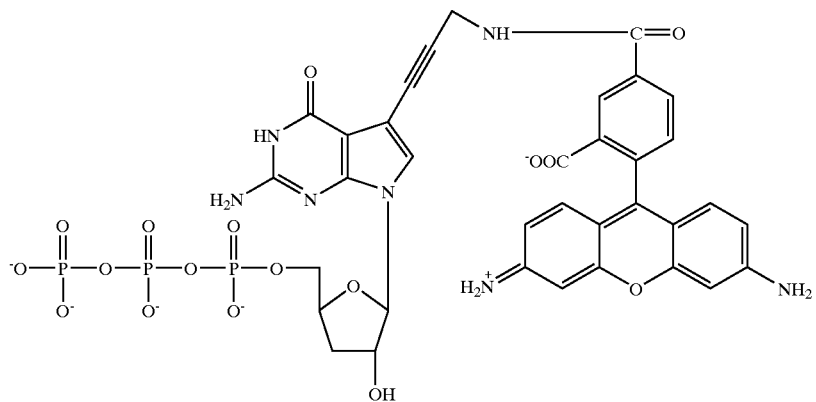

5-Carboxyrhodamine 110-labeled 3'-deoxyguanosine-5'-triphosphate

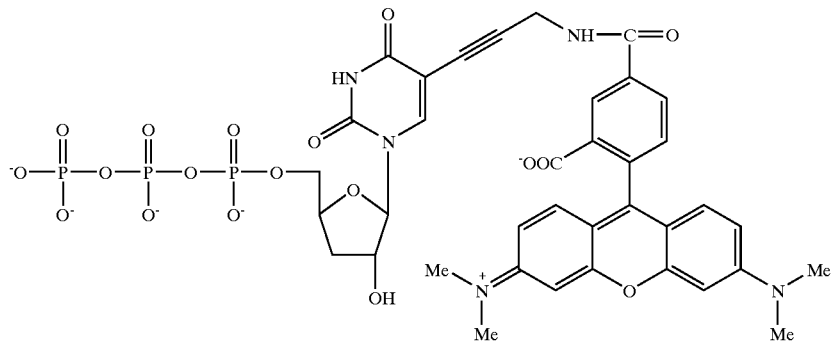

5-Carboxytetramethylrhodamine-labeled 3'-deoxyuridine-5'-triphosphate

The dried reaction product was dissolved in 6 μl of formamide/EDTA/Blue dextran loading buffer according to the instruction manual Ver. 1.0 of ABI PRISM 377 DNA Sequencing System available from Perkin-Elmer Japan, and 2 μl of the solution was analyzed by ABI 377 DNA Sequencer and an analysis program using denatured gel for sequencing analysis which contained 6M urea/4% Long Ranger™ acrylamide solution (FMC). As a result, it was found that the mutant T7 RNA polymerases F644Y and L665P/F667Y could afford higher peak intensity with less fluctuation in comparison with the wild type T7 RNA polymerase, and their sequence reading was possible. When the wild type T7 RNA polymerase was used, its sequence reading was almost impossible.

Example 6

Figure 17:
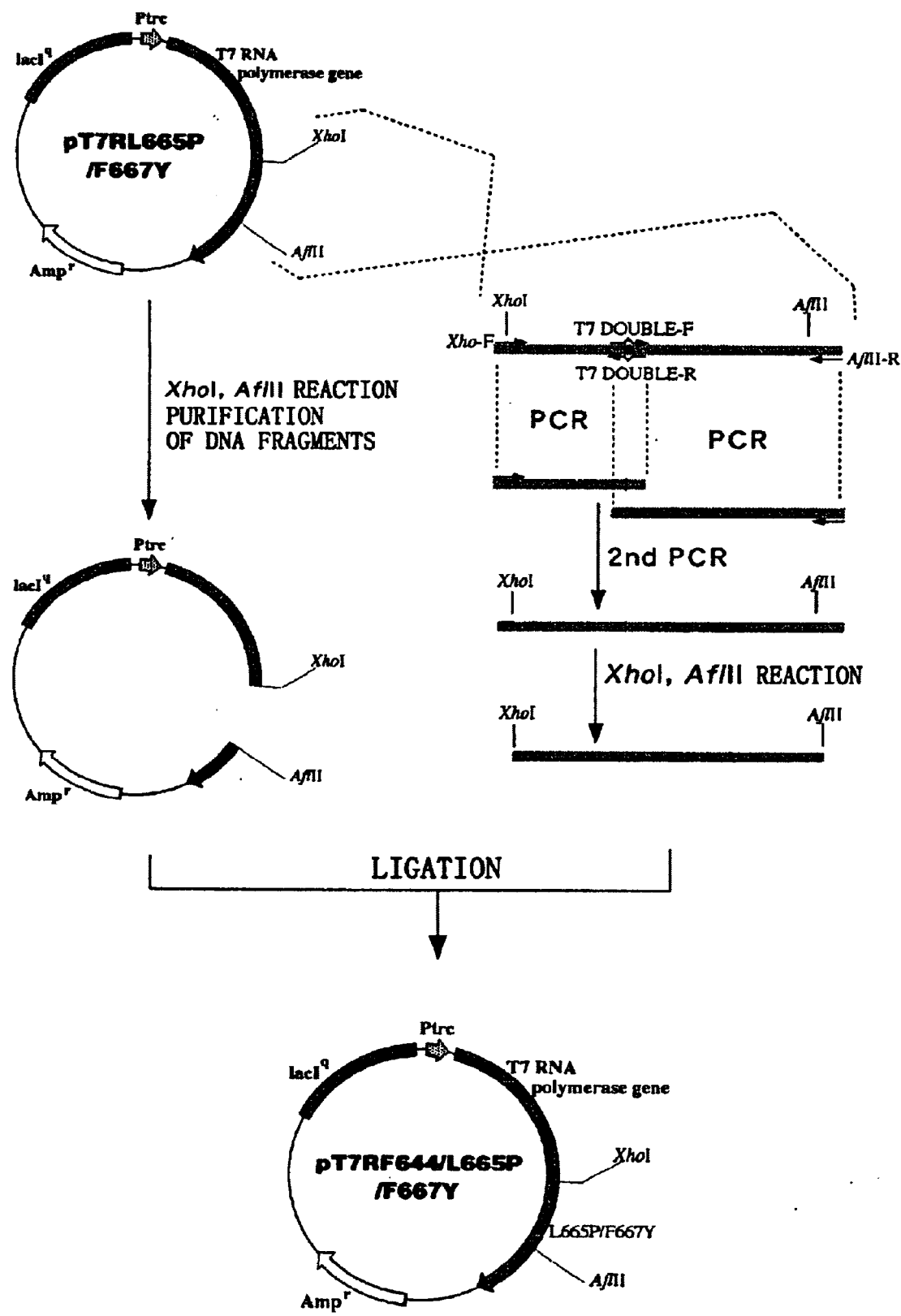
FIG. 17 shows a construction map of pT7R F644Y/L665P/F667Y, a plasmid expressing a mutant T7RNA polymerase F644Y/L665P/F667Y.
Figure 18A:
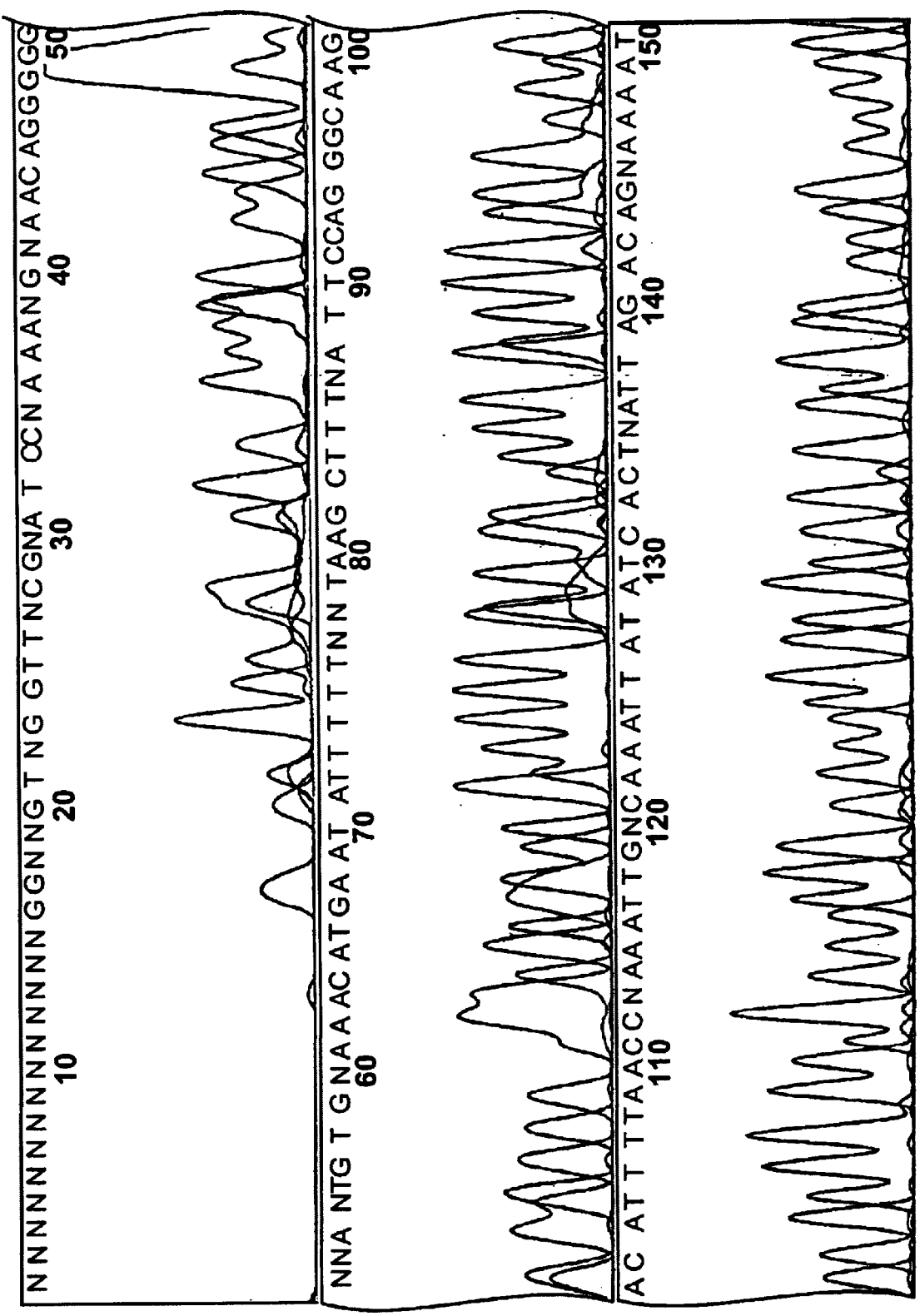
FIGS. 18A–18D demonstrate improvement of incorporation rate of dye terminator by mutant T7 RNA polymerase F644Y/L665P/F667Y (SEQ ID NO:23) as an electropherogram.
Figure 18B:
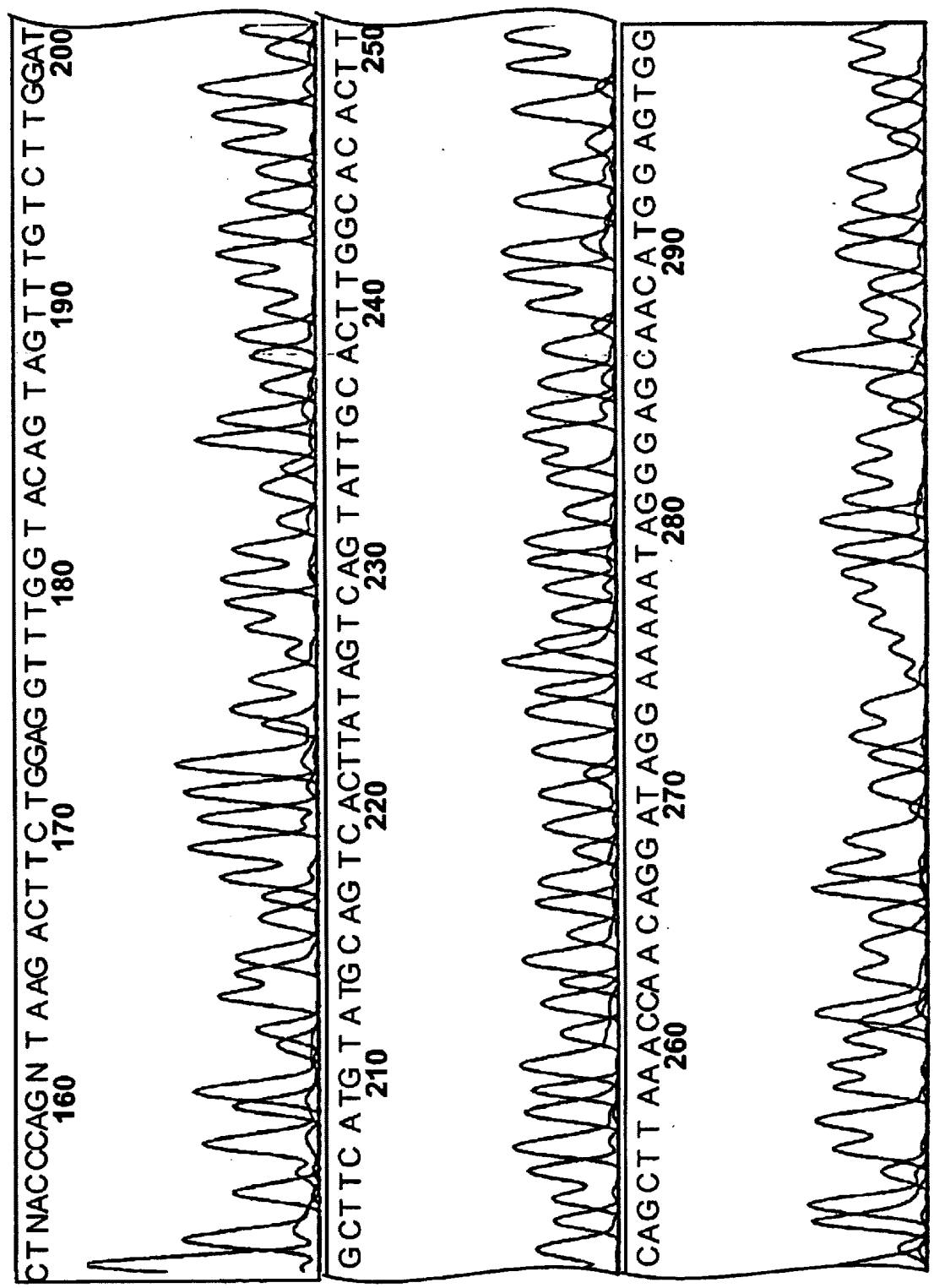
Figure 18C:
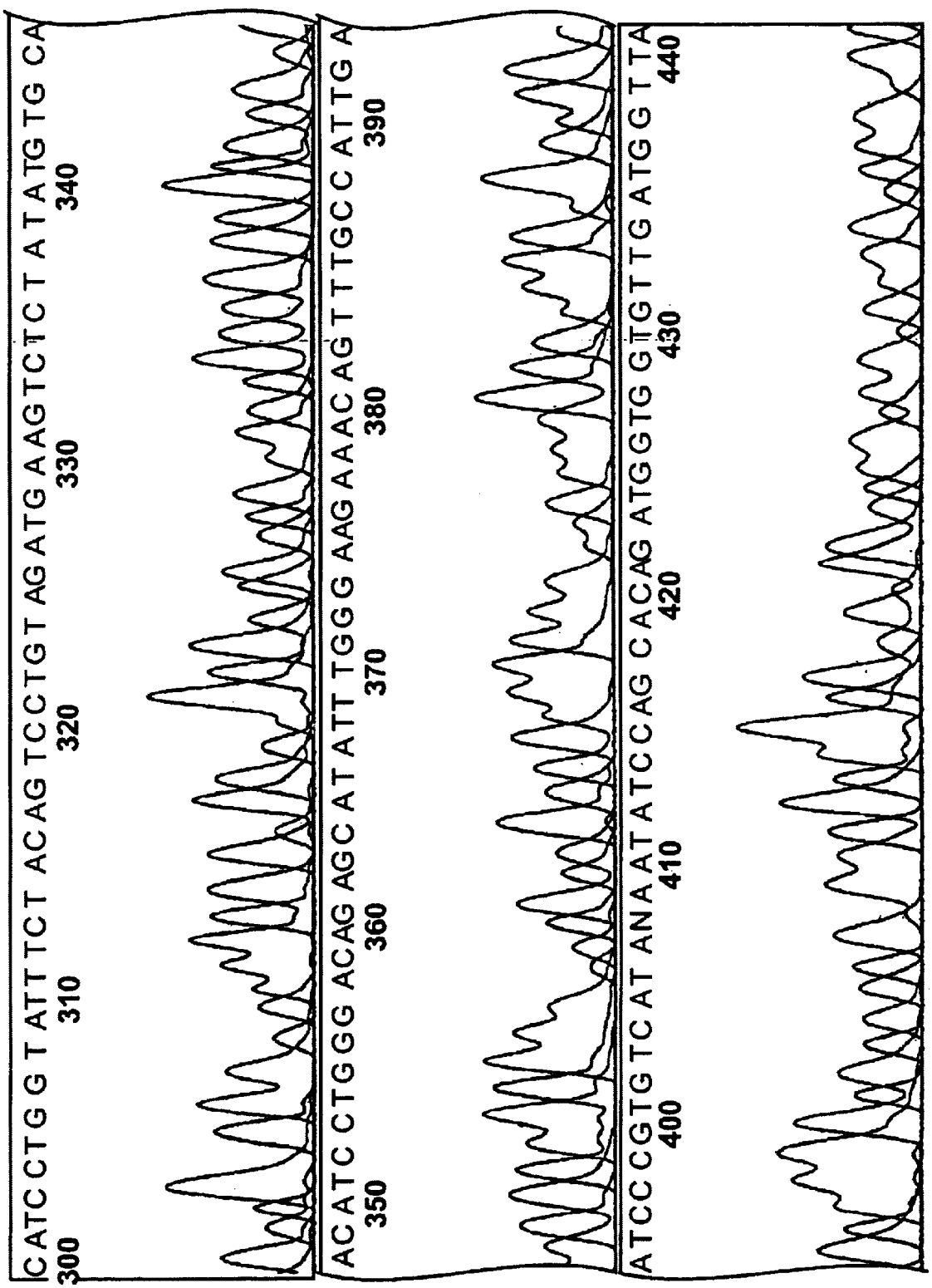
Figure 18D:
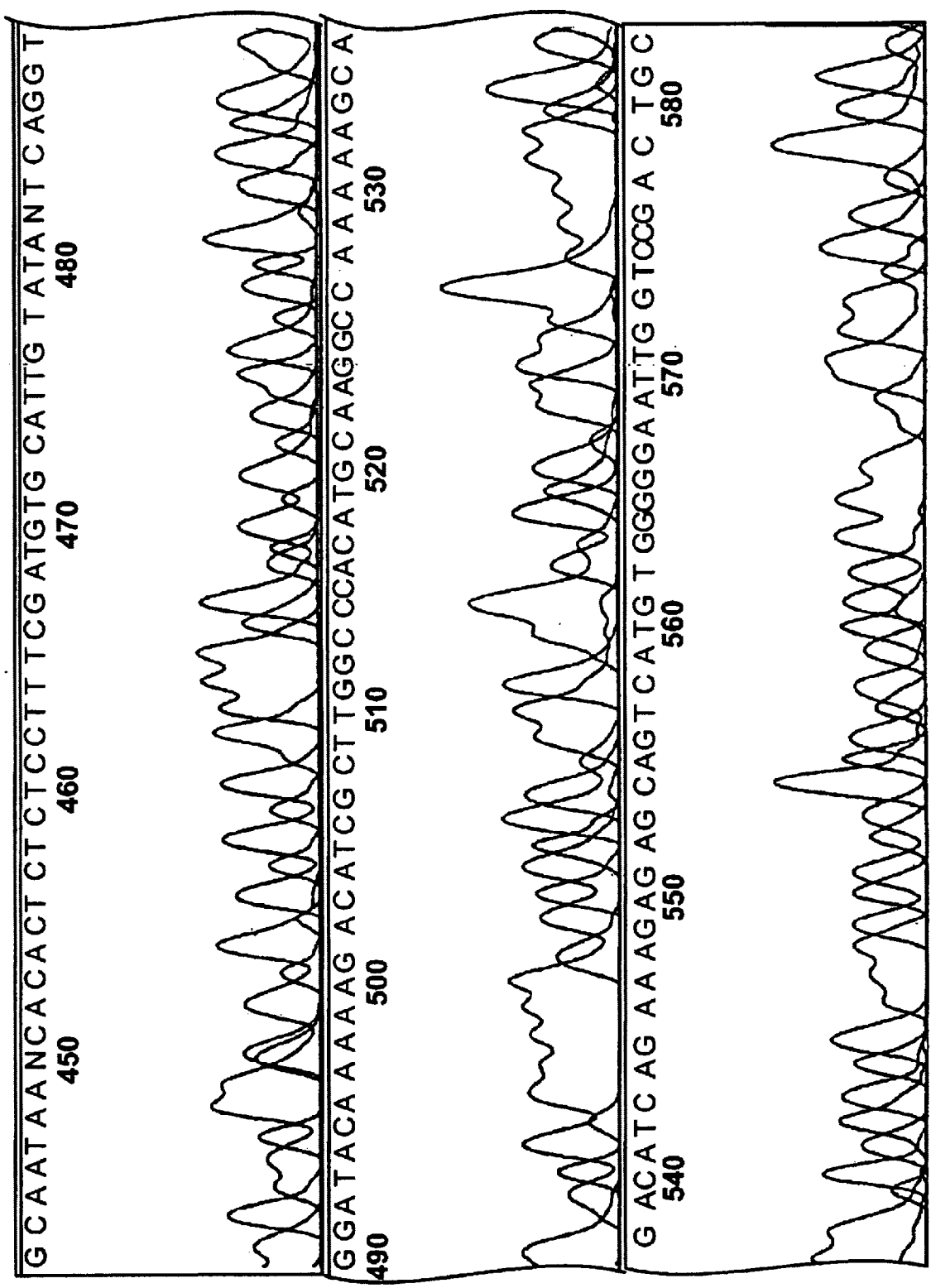

Construction of Expression Plasmid for Producing Mutant T7 RNA Polymerase F644Y/L665P/F667Y (see FIG. 17)

Construction of the mutant T7 RNA polymerase F644Y/L665P/F667Y was performed based on PCR, as in the construction method of the expression plasmid for producing the mutant T7 RNA polymerase L665P/F667Y previously constructed (see Example 2), as follows.

PCR was performed by using the expression plasmid producing the mutant T7 RNA polymerase L665P/F667Y as template together with a primer pair of the primer Xho-F and the primer T7-DOUBLE-R (21-mer: 5'-CTCTTTGGACCCGTAAGCCAG-3' (SEQ ID NO:36)) or a primer pair of the primer T7-DOUBLE-F (29-mer: 5'-TTACGGGTCCAAAGAGTACGGCTTCCGTC-3' (SEQ ID NO:37)) and the primer AflII-R. The PCR products were directly used as templates and determined for DNA sequences to confirm the sequences of the primers T7-DOUBLE-R and T7-DOUBLE-F. Each of the products was subjected to electrophoresis on 2% agarose gel to purify DNA fragment of the intended size. The purified two kinds of DNA fragments were mixed, and used as template for PCR using the primers XhoF and AflIIR. After confirming that the amplified DNA fragment was the desired fragments by restriction mapping and DNA sequencing, the fragment was digested with restriction endonucleases XhoI and AflII, and the resulting fragment was ligated to the plasmid pT7RL665P/F667Y preliminarily treated with restriction endonucleases XhoI and AflII by using T4 DNAligase. This reaction product was transformed into E. coli DH5α, and several colonies of the cells grown on an agar plate containing antibiotic ampicillin were obtained. Some of these colonies were selected and cultured, and plasmid DNA was extracted from the cultured cells. The nucleotide sequence of the plasmid DNA was sequenced to confirm that the desired mutation was introduced, and thus an expression plasmid pT7RF644Y/L665P/F667Y for producing the mutant T7 RNA polymerase F644Y/L665P/F667Y was finally constructed (see FIG. 17). For the production of the mutant T7 RNA polymerase F644Y/L665P/F667Y from this plasmid, expression could be induced by adding IPTG to cultured E. coli cells harboring the plasmid, like the production of the wild type T7 RNA polymerase.

Example 7

Purification of Mutant T7 RNA Polymerase F644Y/L665P/F667Y

The mutant T7 RNA polymerase F644Y/L665P/F667Y could be purified by the same method as in Example 3. In a typical example, 1,000,000 units of the mutant T7 RNA polymerase F644Y/L665P/F667Y protein was purified from 1 liter of culture medium. The obtained RNA polymerase was detected substantially as a single band, and RNase was not detected in this specimen by SDS-polyacrylamide gel electrophoresis.

Example 8

Improvement of Incorporation Rate of 3'-dNTP Derivatives

Ribonucleotide (NTP) and 3'-deoxynucleotide (3'-dNTP) incorporation rates of the mutant T7 RNA polymerase purified in Example 7 were measured as follows.

pBluescript(KS+) plasmid (Stratagene) linearized by reaction with a restriction endonuclease, PvuII, was used as a template for the transcription reaction, and 250 µM each of ATP, CTP, GTP, and UTP, 2 mM of spermidine-$(HCl)_3$, 5 mM of DTT, 40 mM Tris/HCl pH 8.0, 0.1 µl of [$\alpha$-$^{32}$P] UTP (3000 Ci/mmole), and 25 units of the mutant T7 RNA polymerase F644Y/L665P/F667Y were also used for the reaction. For two kinds of reaction mixture (with or without 3'-dATP, final concentration was 100 µM), the reaction was performed at 37° C. for 60 minutes. The whole reaction mixture was spotted on DE81 paper (Whatman), washed three times with phosphate buffer, and dried. The DE81 paper was placed into a scintillation vial, and radioactivity was measured using a scintillation counter (Beckman) for each reaction. Degree of inhibition of the [$\alpha$-$^{32}$P] UTP incorporation was calculated by comparing the values obtained with and without 3'-dATP based on the measured radioactivity. The relative activity obtained from calculated inhibition degree and defined as a relative value to the inhibition degree of the wild type T7 RNA polymerase normalized to 1.000 was shown in Table 1.

The inhibition degree was calculated by using the wild type T7 RNA polymerase, T7 RNA polymerase F644Y, L665P/F667Y obtained in Example 3, mutant T7 RNA polymerase F644Y/L665P, F782Y, F733Y, F646Y or Y639F constructed and purified in the same manner as in Examples 2 and 3 for the reaction instead of the above F644Y/L665P/F667Y mutant, and relative activities are shown in Table 1.

In the results of Table 1, a larger value indicates that the corresponding mutant enzyme has a mutation making 3'-dATP incorporation easier in a higher degree. For example, it is meant that the mutant T7 RNA polymerase F644Y/L665P/F667Y is 5.58 times more likely to incorporate 3I-dATP in comparison with the wild type enzyme. It is demonstrated that the F644Y/L665P/F667Y mutant was the mutant enzyme exhibiting the least bias for the 3'-dATP incorporation among the mutant enzymes prepared.

TABLE 1

| Mutation site | Relative activity of RNA polymerase for 3'-dATP |
|---|---|
| F644Y | 5.130 |
| F644Y/L665P | 5.130 |
| L665P/F667Y | 4.711 |
| F644Y/L665P/F667Y | 5.580 |
| F782Y | 1.173 |
| F733Y | 1.075 |
| F646Y | 0.459 |
| IY639F | 0.930 |
| Wild type | 1.000 |

Example 9

Example of sequencing reaction utilizing mutant T7 RNA polymerase F644Y/L665P/F667Y A template used as a template for sequencing reaction was prepared by PCR as follows.

As the template for PCR, human thyroid-stimulating hormone (hTSH-β) cDNA subcloned into a plasmid derived from BS750 having T7 promoter was used. By using this plasmid 100 µg having hTSH-β with L220 primer (5'-TAA CAA TTT CAC ACA GGA AAC A-3' (SEQ ID NO:38)) and 1211 primer (5'-ACG TTG TAA AAC GAC GGC CAG T-3' (SEQ ID NO:39)) existing at both sides of the cloning site, PCR reaction was performed in a reaction volume of 20 µl (1 cycle of 94° C. for 2 minutes, 30 cycles of 94° C. for 1 minute, 55° C. for 1 minute, and 72° C. for 1.5 minutes, followed by 72° C. for 5 minutes). The T7 promoter existed in the downstream of 1211 primer of the PCR product obtained from the above PCR reaction.

The transcriptional sequencing reaction was performed by the method of Melton, D. A, [Nucleic Acids Res., 12: 7035–7056 (1984)].

1 µl (about 10 ng) of the above PCR product was used for the sequencing reaction. The reaction was performed in a total reaction volume of 10 µl containing the same dye terminators as used in Example 5, 4 µM R6G-3'-dATP [5-carboxyrhodamine 6G-labeled 3'-deoxyadenosine-5-triphosphate (n=4)], 4 µM R110-3'-dGTP [5-carboxyrhodamine 110-labeled 3'-deoxyguanosine-5-triphosphate (n=4)], 80 µM XR-3'-dCTP [5-carboxy-X-rhodamine-labeled 3''deoxycytidine-5-triphosphate (n=4)], 20 µM TMR-3'-dUTP [5-carboxytetramethylrhodamine-labeled 3'-deoxyuridine-5-triphosphate (n=4)], 500 µM UTP, 250 µM ATP, 200 µM CTP, 500 µM GTP, 2 mM spermidine-$(HCl)_3$, 5 mM DTT, 40 mM Tris/HCl pH 8.0 (BRL, Gibco) and 25 units of the mutant T7 RNA polymerase F644Y/L665P/F667Y at 37° C. for 1 hour.

Then, to remove the unreacted dye terminator remaining in the reaction product, the transcription product was purified by gel filtration using Sephadex G-50 column (Pharmacia Biotec), and the purification product was evaporated to dryness using a centrifugal evaporator.

The dried reaction product was dissolved in 6 µl of formamide/EDTA/Blue dextran loading buffer according to the instruction manual Ver. 1.0 of ABI PRISM 377 DNA Sequencing System available from Perkin-Elmer Japan, and 2 µl of the solution was analyzed by ABI 377 DNA Sequencer and an analysis program (Sequencing Analysis Ver. 3.0) using denatured gel for sequencing analysis which contained 6M urea/4% Long Ranger™ acrylamide solution (FMC) to afford an electropherogram. The results are shown in FIG. 18. Excellent sequencing analysis was possible as is demonstrated.

What is claimed is:

1. An RNA polymerase which is an RNA polymerase from T7 phage, and has tyrosine at amino acid residue 644 and/or 667 of SEQ ID NO:2.

2. An RNA polymerase comprising an RNA polymerase of claim 1 with a further substitution, insertion, or deletion of an amino acid other than the amino acid residues 644 and/or 667 of SEQ ID NO:2, and wherein the further substitution, insertion, or deletion does not substantially affect the RNA polymerase activity.

3. An RNA polymerase consisting of a wild type T7 RNA polymerase provided that the 644th amino acid residue of SEQ ID NO:2 of the wild type T7 RNA polymerase, phenylalanine, has been replaced with tyrosine.

4. An RNA polymerase consisting of a wild type T7 RNA polymerase provided that the 667th amino acid residue, phenylalanine, of SEQ ID NO:2 of the wild type T7 RNA polymerase has been replaced with tyrosine.

5. An RNA polymerase comprising an RNA polymerase of claim 3 with a further mutation wherein the 665th amino acid residue, leucine, of SEQ ID NO:2 of the wild type T7 RNA polymerase has been replaced with proline.

6. An RNA polymerase consisting of a wild type T7 RNA polymerase provided that the 644th amino acid residue, phenylalanine, of SEQ ID NO:2 of the wild type T7 RNA polymerase has been replaced with tyrosine, and the 667th amino acid residue, phenylalanine, of SEQ ID NO:2 of the wild type T7 RNA polymerase has been replaced with tyrosine.

7. An RNA polymerase comprising an RNA polymerase of claim 6 with a further mutation wherein the 665th amino acid residue, leucine, of SEQ ID NO:2 of the wild type T7 RNA polymerase has been replaced with proline.

8. An RNA polymerase which is an RNA polymerase from T3 phage, and has tyrosine at amino acid residue 645 or 668 of SEQ ID NO:4.

9. An RNA polymerase comprising an RNA polymerase of claim 8 with a further mutation wherein the RNA polymerase from T3 phage has a further substitution, insertion, or deletion of an amino acid other than the amino acid residues 645 and 668 of SEQ ID NO:4, and wherein the further substitution, insertion, or deletion does not substantially affect the RNA polymerase activity.

10. An RNA polymerase which is an RNA polymerase from K11 phage, and has tyrosine at one or more amino acid residues 664–69 and 6690 of SEQ ID NO:5.

11. An RNA polymerase comprising an RNA polymerase of claim 10 with a further mutation wherein the RNA polymerase from K11 phage has a further substitution, insertion, or deletion of an amino acid other than the amino acid residues 664–669 and 690 of SEQ ID NO:5, and wherein the further substitution, insertion, or deletion does not substantially affect the RNA polymerase activity.

12. An RNA polymerase which is RNA polymerase from SP6 phage, and has tyrosine at one or more amino acid residues 633–638 and 670 of SEQ ID NO:6.

13. An RNA polymerase comprising an RNA polymerase of claim 12 with a further mutation wherein the RNA polymerase from SP6 phage has a further substitution, insertion, or deletion of an amino acid other than the amino acid residues 633–638 and 670 of SEQ ID NO:6, and wherein the further substitution, insertion, or deletion does not substantially affect the RNA polymerase activity.

* * * * *